(12) United States Patent
Burdach et al.

(10) Patent No.: US 8,530,155 B2
(45) Date of Patent: Sep. 10, 2013

(54) METHODS FOR DIAGNOSIS OF COMMON ACUTE LYMPHOBLASTIC LEUKEMIA BY DETERMINING THE LEVEL OF GENE EXPRESSION

(75) Inventors: Stefan Burdach, München (DE); Günther Richter, München (DE)

(73) Assignee: Stefan Burdach, Munich (DE)

( * ) Notice: Subject to any disclaimer, the term of this patent is extended or adjusted under 35 U.S.C. 154(b) by 206 days.

(21) Appl. No.: 12/377,863

(22) PCT Filed: Aug. 17, 2007

(86) PCT No.: PCT/EP2007/007297
§ 371 (c)(1),
(2), (4) Date: Feb. 18, 2009

(87) PCT Pub. No.: WO2008/019872
PCT Pub. Date: Feb. 21, 2008

(65) Prior Publication Data
US 2010/0055686 A1 Mar. 4, 2010

(30) Foreign Application Priority Data
Aug. 18, 2006 (EP) .................................... 06017264

(51) Int. Cl.
*C12Q 1/68* (2006.01)

(52) U.S. Cl.
USPC .......................................................... 435/6.1

(58) Field of Classification Search
None
See application file for complete search history.

(56) References Cited

FOREIGN PATENT DOCUMENTS

| WO | WO 2006/048270 | 5/2006 |
|---|---|---|
| WO | WO 2006/086043 | 8/2006 |

OTHER PUBLICATIONS

Affymetrix Inc (The Affymetrix GeneChip HG-U133A; 2002).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Lichtinghagen et al (European Urology, 2002, 42:398-406).*
Haferlach et al (Clinical Observations, Interventions, and Therapeutic Trials; Aug. 15, 2005, 106(4): 1189-1198).*
Richter et al (Blood, ASH Annual Meeting Abstracts, 2005, 106, Abstract 4352).*
Tockman et al (Cancer Res., 1992, 52:2711s-2718s).*
"Affymetrix GeneChip Human Genome U133 Array Set HG-U133A", GEO Platform GPL96 (Mar. 11, 2002).
Haferlach, Torsten et al., "Global Approach to the Diagnosis of Leukemia Using Gene Expression Profiling", Blood, vol. 106 (4), pp. 1189-1198 (Aug. 2005).
MacKenzie, J. et al., "Screening for Herpes Virus Genomes in Common Acute Lymphoblastic Leukemia", Leukemia, vol. 15 (3), pp. 415-421 (Mar. 2001).
Richter, Gunter et al., "Transcriptome Analysis of Pediatric cALL Versus Normal Fetal B Cells Reveals a Novel Signature of the Malignant Phenotype", Blood (ASH Annual Meeting Abstracts), vol. 106, Abstract 4352 (2005).

* cited by examiner

*Primary Examiner* — Sean Aeder
(74) *Attorney, Agent, or Firm* — Chalin A. Smith; Smith Patent Consulting

(57) ABSTRACT

The present invention refers to a method and a kit for diagnosing pediatric common acute leukemia by distinguishing between normal and common acute lymphoblastic leukemic (cALL) cells, wherein the method comprises the step of determining the gene expression of specific genes (markers) referring to this disease and the step of determining whether these genes are up-regulated or down-regulated. The method for determining the gene expression levels can apply hybridization techniques or PCR methods or combinations thereof. The present invention provides new gene markers, which have not been reported in context with cALL and are suitable for the diagnosis of this disease. In addition, the present invention refers to utilizing these targets for the development of targeted therapies employing RNA- and DNA-interference, antibodies, aptamers, anticalins and other small molecules.

17 Claims, 74 Drawing Sheets

FIG. 9

Table 1

| uniqid | Gene Symbol | Gene ID | Score(d) | Fold Change | q-value (%) |
|---|---|---|---|---|---|
| 219686_at | STK32B | NM_018401.1 | 5,21258795 | 70,50159 | 0,16349815 |
| 203821_at | DTR | NM_001945.1 | 4,58196056 | 26,14573 | 0,16349815 |
| 206548_at | FLJ23556 | NM_024880.1 | 4,51016439 | 22,43302 | 0,16349815 |
| 207030_s_at | CSRP2 | NM_001321.1 | 4,42194787 | 32,12154 | 0,16349815 |
| 214455_at | HIST1H2BC | NM_003526.1 | 4,08410483 | 13,74617 | 0,16349815 |
| 204083_s_at | TPM2 | NM_003289.1 | 3,80317072 | 12,16817 | 0,16349815 |
| 38037_at | DTR | M60278 | 3,73341094 | 15,75834 | 0,16349815 |
| 201329_s_at | ETS2 | NM_005239.1 | 3,63741689 | 13,10507 | 0,16349815 |
| 202481_at | DHRS3 | NM_004753.1 | 3,54350956 | 9,08517 | 0,16349815 |
| 222303_at | --- | AV700891 | 3,38335076 | 12,76201 | 0,16349815 |
| 216035_x_at | TCF7L2 | AV721430 | 3,38229053 | 6,89967 | 0,16349815 |
| 212013_at | D2S448 | D86983.1 | 3,36264562 | 8,49028 | 0,16349815 |
| 211341_at | POU4F1 | L20433.1 | 3,35467618 | 36,79822 | 0,16349815 |
| 203373_at | SOCS2 | NM_003877.1 | 3,31104953 | 8,22452 | 0,16349815 |
| 208893_s_at | DUSP6 | BC005047.1 | 3,29663499 | 27,24485 | 0,16349815 |
| 202242_at | TM4SF2 | NM_004615.1 | 3,26806143 | 12,25609 | 0,16349815 |
| 215597_x_at | MYST4 | AU143799 | 3,26763189 | 6,86309 | 0,16349815 |
| 203325_s_at | COL5A1 | AI130969 | 3,22968817 | 10,06737 | 0,16349815 |
| 221349_at | VPREB1 | NM_007128.1 | 3,17175847 | 29,65737 | 0,16349815 |
| 203372_s_at | SOCS2 | AB004903.1 | 3,16955259 | 8,798 | 0,16349815 |
| 201565_s_at | ID2 | NM_002166.1 | 3,12376982 | 12,91039 | 0,16349815 |
| 215743_at | NMT2 | AL134489 | 3,1176101 | 5,72186 | 0,16349815 |
| 218051_s_at | FLJ12442 | NM_022908.1 | 3,05909223 | 5,98974 | 0,16349815 |
| 204011_at | SPRY2 | NM_005842.1 | 3,02096517 | 10,09141 | 0,16349815 |
| 209025_s_at | SYNCRIP | AF037448.1 | 3,01562031 | 5,24967 | 0,16349815 |
| 201830_s_at | NET1 | NM_005863.1 | 2,99849305 | 9,67614 | 0,16349815 |
| 218311_at | MAP4K3 | NM_003618.1 | 2,97258701 | 5,53905 | 0,16349815 |
| 211052_s_at | TBCD | BC006364.1 | 2,93936985 | 9,84326 | 0,16349815 |
| 218402_s_at | HPS4 | NM_022081.1 | 2,93527602 | 6,88468 | 0,16349815 |
| 201170_s_at | BHLHB2 | NM_003670.1 | 2,90396696 | 8,17656 | 0,16349815 |
| 208890_s_at | PLXNB2 | BC004542.1 | 2,87652685 | 9,1662 | 0,16349815 |
| 218880_at | FOSL2 | NM_024530.1 | 2,87082903 | 17,10764 | 0,16349815 |
| 215398_at | HRPT2 | AF038194.1 | 2,83312103 | 5,52282 | 0,16349815 |
| 204759_at | CHC1L | NM_001268.1 | 2,81620248 | 5,60794 | 0,16349815 |

FIG. 9 (Continued)

TABLE 1 (Continued)

| | | | | | |
|---|---|---|---|---|---|
| 201566_x_at | ID2 | D13891.1 | 2,77550424 | 7,02998 | 0,16349815 |
| 209568_s_at | RGL1 | AF186779.1 | 2,77416962 | 7,1704 | 0,16349815 |
| 205290_s_at | BMP2 | NM_001200.1 | 2,77089326 | 14,76706 | 0,16349815 |
| 214623_at | SHFM3P1 | AA845710 | 2,74311404 | 5,27094 | 0,16349815 |
| 220359_s_at | ARPP-21 | NM_016300.1 | 2,72887773 | 22,4658 | 0,16349815 |
| 215218_s_at | C19orf14 | AC004144 | 2,72185346 | 4,33475 | 0,16349815 |
| 216511_s_at | TCF7L2 | AJ270770 | 2,70431774 | 4,82314 | 0,16349815 |
| 220918_at | C21orf96 | NM_025143.1 | 2,7010981 | 5,86336 | 0,16349815 |
| 211066_x_at | PCDHGA3 | BC006439.1 | 2,69566326 | 5,46935 | 0,16349815 |
| 214696_at | MGC14376 | AF070569.1 | 2,685678 | 7,80167 | 0,16349815 |
| 201401_s_at | ADRBK1 | NM_001619.2 | 2,68551594 | 6,12232 | 0,16349815 |
| 220085_at | HELLS | NM_018063.1 | 2,62632619 | 4,7809 | 0,16349815 |
| 207697_x_at | LILRB2 | NM_005874.1 | 2,62124408 | 3,99063 | 0,16349815 |
| 213827_at | SNX26 | AL137579.1 | 2,61659514 | 4,48069 | 0,16349815 |
| 218856_at | TNFRSF21 | NM_016629.1 | 2,59998917 | 8,10701 | 0,16349815 |
| 212012_at | D2S448 | BF342851 | 2,59972845 | 5,26138 | 0,16349815 |
| 214761_at | ZNF423 | AW149417 | 2,59825698 | 6,10268 | 0,16349815 |
| 218589_at | P2RY5 | NM_005767.1 | 2,59798335 | 7,70067 | 0,16349815 |
| 216766_at | PRKCE | AK025152.1 | 2,57824036 | 3,88585 | 0,16349815 |
| 219493_at | SHCBP1 | NM_024745.1 | 2,56130388 | 5,29014 | 0,16349815 |
| 209210_s_at | PLEKHC1 | Z24725.1 | 2,55950934 | 14,11969 | 0,16349815 |
| 208891_at | DUSP6 | BC003143.1 | 2,55507866 | 8,10323 | 0,16349815 |
| 212759_s_at | TCF7L2 | AI703074 | 2,54503968 | 6,00555 | 0,16349815 |
| 215223_s_at | SOD2 | W46388 | 2,53570374 | 7,56057 | 0,16349815 |
| 220448_at | KCNK12 | NM_022055.1 | 2,52151072 | 23,4441 | 0,16349815 |
| 207705_s_at | KIAA0980 | NM_025176.1 | 2,51969499 | 6,56891 | 0,16349815 |
| 209035_at | MDK | M69148.1 | 2,5184133 | 14,23192 | 0,16349815 |
| 202392_s_at | PISD | NM_014338.1 | 2,49570169 | 3,78572 | 0,16349815 |
| 213008_at | FLJ10719 | BG403615 | 2,49261192 | 3,88768 | 0,16349815 |
| 221840_at | PTPRE | AA775177 | 2,47980234 | 5,58391 | 0,16349815 |
| 205135_s_at | NUFIP1 | NM_012345.1 | 2,46539741 | 3,78909 | 0,16349815 |
| 209079_x_at | PCDHGA3 | AF152318.1 | 2,45452854 | 5,80181 | 0,16349815 |
| 215028_at | SEMA6A | AB002438.1 | 2,45082987 | 12,36692 | 0,16349815 |
| 203350_at | AP1G1 | NM_001128.1 | 2,44797136 | 4,99958 | 0,16349815 |
| 211101_x_at | LILRA2 | U82276.1 | 2,4401662 | 5,80157 | 0,16349815 |
| 201416_at | SOX4 | BG528420 | 2,42537008 | 5,18605 | 0,16349815 |
| 202519_at | MONDOA | NM_014938.1 | 2,4234139 | 3,95918 | 0,16349815 |
| 205983_at | DPEP1 | NM_004413.1 | 2,41992701 | 7,98064 | 0,16349815 |
| 201418_s_at | SOX4 | NM_003107.1 | 2,41664283 | 4,8183 | 0,16349815 |
| 217534_at | --- | AA845825 | 2,4155383 | 3,80221 | 0,16349815 |
| 220728_at | --- | NM_025120.1 | 2,41540187 | 4,18975 | 0,16349815 |

FIG. 9 (Continued)

TABLE 1 (Continued)

| | | | | | |
|---|---|---|---|---|---|
| 204109_s_at | NFYA | NM_002505.2 | 2,40928668 | 3,75718 | 0,16349815 |
| 204822_at | TTK | NM_003318.1 | 2,40884455 | 3,20765 | 0,16349815 |
| 34726_at | CACNB3 | U07139 | 2,39114999 | 3,76677 | 0,16349815 |
| 211924_s_at | PLAUR | AY029180.1 | 2,37317631 | 4,86998 | 0,16349815 |
| 212761_at | TCF7L2 | AI949687 | 2,37043268 | 4,76268 | 0,16349815 |
| 201543_s_at | SARA1 | NM_020150.1 | 2,35966738 | 3,73338 | 0,27903683 |
| 201920_at | SLC20A1 | NM_005415.2 | 2,35109617 | 3,55435 | 0,27903683 |
| 212124_at | RAI17 | AF070622.1 | 2,34721001 | 3,53563 | 0,27903683 |
| 209711_at | SLC35D1 | AB044343.1 | 2,34595683 | 4,99377 | 0,27903683 |
| 201389_at | ITGA5 | NM_002205.1 | 2,3355619 | 3,50848 | 0,27903683 |
| 204790_at | SMAD7 | NM_005904.1 | 2,33482974 | 5,87241 | 0,27903683 |
| 215836_s_at | PCDHGC3 | AK026188.1 | 2,33174823 | 5,84045 | 0,27903683 |
| 212558_at | SPRY1 | BF508662 | 2,32753345 | 5,6767 | 0,27903683 |
| 205330_at | MN1 | NM_002430.1 | 2,32135263 | 5,26912 | 0,27903683 |
| 204825_at | MELK | NM_014791.1 | 2,31649015 | 3,7591 | 0,27903683 |
| 213668_s_at | SOX4 | AI989477 | 2,30644493 | 4,638 | 0,27903683 |
| 202933_s_at | YES1 | NM_005433.1 | 2,30007241 | 5,73371 | 0,27903683 |
| 208892_s_at | DUSP6 | BC003143.1 | 2,29732557 | 5,10926 | 0,27903683 |
| 222217_s_at | SLC27A3 | BC003654.1 | 2,29049135 | 4,60827 | 0,27903683 |
| 2028_s_at | E2F1 | NM_004172.1 | 2,28092046 | 3,46024 | 0,27903683 |
| 212812_at | --- | AI700633 | 2,27772145 | 5,76166 | 0,27903683 |
| 222101_s_at | DCHS1 | BF222893 | 2,26568903 | 8,91926 | 0,27903683 |
| 212142_at | MCM4 | AI936566 | 2,26558842 | 3,00975 | 0,27903683 |
| 213280_at | GARNL4 | AK000478.1 | 2,26540277 | 4,57819 | 0,27903683 |
| 212959_s_at | MGC4170 | AK001821.1 | 2,26288788 | 4,87606 | 0,4885859 |
| 212762_s_at | TCF7L2 | AI375916 | 2,2586835 | 4,357 | 0,4885859 |
| 212509_s_at | FLJ46603 | BF968134 | 2,24625951 | 5,24114 | 0,4885859 |
| 201324_at | EMP1 | NM_001423.1 | 2,24014738 | 9,25391 | 0,4885859 |
| 201195_s_at | SLC7A5 | AB018009.1 | 2,23017035 | 4,94429 | 0,4885859 |
| 219753_at | STAG3 | NM_012447.1 | 2,22022804 | 11,484 | 0,4885859 |
| 220137_at | FLJ20674 | NM_019086.1 | 2,21898693 | 3,18852 | 0,4885859 |
| 219863_at | HERC5 | NM_016323.1 | 2,21665716 | 3,5046 | 0,4885859 |
| 202039_at | MYO18A /// TIAF1 | NM_004740.1 | 2,21124134 | 4,33512 | 0,4885859 |
| 213931_at | ID2 | AI819238 | 2,21068765 | 8,21485 | 0,4885859 |
| 214290_s_at | HIST2H2AA | AI313324 | 2,21063641 | 4,40511 | 0,4885859 |
| 201890_at | RRM2 | BE966236 | 2,20936349 | 3,10905 | 0,4885859 |
| 202555_s_at | MYLK | NM_005965.1 | 2,19508672 | 7,66304 | 0,4885859 |
| 205289_at | BMP2 | AA583044 | 2,19362389 | 7,88597 | 0,4885859 |
| 212489_at | COL5A1 | AI983428 | 2,18941515 | 7,83748 | 0,4885859 |

FIG. 9 (Continued)

TABLE 1 (Continued)

| | | | | | |
|---|---|---|---|---|---|
| 220691_at | TMEM23 | NM_014114.1 | 2,1893909 | 3,27208 | 0,4885859 |
| 204900_x_at | SAP30 | NM_003864.1 | 2,18823434 | 5,06262 | 0,4885859 |
| 215177_s_at | ITGA6 | AV733308 | 2,18621756 | 19,49684 | 0,4885859 |
| 209053_s_at | WHSC1 | BE793789 | 2,17496971 | 3,78534 | 0,64064579 |
| 213792_s_at | --- | AA485908 | 2,16990117 | 5,42146 | 0,64064579 |
| 215201_at | REPS1 | AW166925 | 2,15820255 | 4,49086 | 0,64064579 |
| 202087_s_at | CTSL | NM_001912.1 | 2,15381767 | 4,79533 | 0,64064579 |
| 204999_s_at | ATF5 | BC005174.1 | 2,1469704 | 3,24081 | 0,64064579 |
| 213135_at | TIAM1 | U90902.1 | 2,13194559 | 3,60627 | 0,64064579 |
| 214581_x_at | TNFRSF21 | BE568134 | 2,12511119 | 5,01442 | 0,64064579 |
| 215577_at | UBE2E1 | AU146791 | 2,12424382 | 3,65715 | 0,64064579 |
| 201656_at | ITGA6 | NM_000210.1 | 2,12281338 | 13,6282 | 0,64064579 |
| 208370_s_at | DSCR1 | NM_004414.2 | 2,11954175 | 6,09355 | 0,64064579 |
| 213605_s_at | FLJ40092 | AL049987.1 | 2,11053388 | 3,76917 | 0,64064579 |
| 212478_at | FLJ13910 | H65865 | 2,1089567 | 4,06505 | 0,64064579 |
| 221821_s_at | FLJ20436 | AK022732.1 | 2,10681261 | 3,52389 | 0,64064579 |
| 203066_at | GALNAC4S-6ST | NM_014863.1 | 2,10301859 | 5,92611 | 0,64064579 |
| 222371_at | --- | AI732802 | 2,09683904 | 3,729 | 0,64064579 |
| 212520_s_at | SMARCA4 | AI684141 | 2,09551675 | 4,18882 | 0,64064579 |
| 215268_at | KIAA0754 | AW663712 | 2,09386516 | 3,25299 | 0,64064579 |
| 218613_at | PSD3 | NM_018422.1 | 2,09312934 | 3,39306 | 0,64064579 |
| 209365_s_at | ECM1 | U65932.1 | 2,09143038 | 5,38046 | 0,64064579 |
| 207857_at | LILRA2 | NM_006866.1 | 2,08669888 | 3,59777 | 0,64064579 |
| 204805_s_at | H1FX | NM_006026.1 | 2,0854445 | 4,4188 | 0,64064579 |
| 208015_at | SMAD1 | NM_015583.1 | 2,08493212 | 6,13181 | 0,64064579 |
| 221992_at | LOC283970 | AI925734 | 2,08198561 | 3,21319 | 0,8509783 |
| 211126_s_at | CSRP2 | U46006.1 | 2,07235363 | 3,39878 | 0,8509783 |
| 203853_s_at | GAB2 | NM_012296.1 | 2,07055061 | 3,1386 | 0,8509783 |
| 209122_at | ADFP | BC005127.1 | 2,06922632 | 5,75449 | 0,8509783 |
| 214059_at | IFI44 | BE049439 | 2,06634126 | 4,67301 | 0,8509783 |
| 213056_at | FRMD4B | AU145019 | 2,03971017 | 4,03616 | 0,8509783 |
| 211430_s_at | IGHG1 | M87789.1 | 2,03969731 | 10,21196 | 0,8509783 |
| 207735_at | RNF125 | NM_017831.1 | 2,03075014 | 4,14014 | 0,8509783 |
| 220450_at | --- | NM_024914.1 | 2,0298278 | 4,2061 | 0,8509783 |
| 219978_s_at | NUSAP1 | NM_018454.1 | 2,02823859 | 3,8101 | 0,8509783 |
| 201328_at | ETS2 | AL575509 | 2,02729409 | 5,23557 | 0,8509783 |
| 201976_s_at | MYO10 | NM_012334.1 | 2,01954182 | 8,4435 | 0,8509783 |
| 201663_s_at | SMC4L1 | NM_005496.1 | 2,01659256 | 3,49192 | 0,8509783 |
| 212303_x_at | KHSRP | BG026366 | 2,01636695 | 3,09446 | 0,8509783 |

FIG. 9 (Continued)

TABLE 1 (Continued)

| 204159_at | CDKN2C | NM_001262.1 | 2,00569025 | 3,40054 | 0,8509783 |
|---|---|---|---|---|---|
| 219499_at | SEC61A2 | NM_018144.1 | 2,00464873 | 3,15278 | 0,8509783 |
| 201939_at | PLK2 | NM_006622.1 | 1,99568293 | 4,50617 | 0,8509783 |
| 201337_s_at | VAMP3 | NM_004781.2 | 1,98683779 | 3,84507 | 1,08824365 |
| 211031_s_at | CYLN2 | BC006259.1 | 1,98574282 | 3,47162 | 1,08824365 |
| 202910_s_at | CD97 | NM_001784.1 | 1,98498791 | 5,52486 | 1,08824365 |
| 216997_x_at | TLE4 | AL358975 | 1,97741214 | 5,23686 | 1,08824365 |
| 218091_at | HRB | AI989512 | 1,97492422 | 3,70233 | 1,08824365 |
| 209197_at | SYT11 | AA626780 | 1,96899305 | 3,47662 | 1,08824365 |
| 213718_at | RBM4 | BE222257 | 1,96846098 | 3,09314 | 1,08824365 |
| 211102_s_at | LILRA2 | U82277.1 | 1,96671467 | 3,7441 | 1,08824365 |
| 219470_x_at | CCNJ | NM_019084.1 | 1,96627943 | 4,20271 | 1,08824365 |
| 1405_I_at | CCL5 | M21121 | 1,96484529 | 3,7647 | 1,08824365 |
| 215750_at | KIAA1659 | AB051446.1 | 1,95600069 | 3,28089 | 1,08824365 |
| 202779_s_at | UBE2S | NM_014501.1 | 1,95096401 | 4,64 | 1,08824365 |
| 203349_s_at | ETV5 | NM_004454.1 | 1,95024314 | 6,35641 | 1,08824365 |
| 208886_at | H1F0 | BC000145.1 | 1,94926438 | 9,05862 | 1,08824365 |
| 209815_at | PTCH | BG054916 | 1,9465153 | 6,36288 | 1,08824365 |
| 221832_s_at | LUZP1 | AV741657 | 1,94422439 | 3,5622 | 1,08824365 |
| 207746_at | POLQ | NM_014125.1 | 1,93615366 | 3,02734 | 1,08824365 |
| 216813_at | --- | AL512728.1 | 1,93463053 | 5,94022 | 1,08824365 |
| 211100_x_at | LILRA2 | U82278.1 | 1,93332365 | 3,53692 | 1,08824365 |
| 38671_at | PLXND1 | AB014520 | 1,92399321 | 3,05031 | 1,08824365 |
| 212384_at | BAT1 | AI282485 | 1,92392735 | 4,74883 | 1,08824365 |
| 218192_at | IHPK2 | NM_016291.1 | 1,9210127 | 3,61466 | 1,08824365 |
| 202668_at | EFNB2 | BF001670 | 1,91974651 | 7,38806 | 1,08824365 |
| 202672_s_at | ATF3 | NM_001674.1 | 1,91913135 | 3,9507 | 1,08824365 |
| 202870_s_at | CDC20 | NM_004295.1 | 1,91541597 | 3,01741 | 1,08824365 |
| 210993_s_at | SMAD1 | U54826.1 | 1,91489774 | 9,64458 | 1,08824365 |
| 203355_s_at | PSD3 | NM_015310.1 | 1,91266138 | 4,31181 | 1,08824365 |
| 218883_s_at | MLF1IP | NM_024629.1 | 1,91145614 | 3,0125 | 1,08824365 |
| 214505_s_at | FHL1 | AF220153.1 | 1,91062398 | 4,32745 | 1,08824365 |
| 207100_s_at | VAMP1 | NM_016830.1 | 1,90855738 | 3,77302 | 1,08824365 |
| 202725_at | POLR2A | NM_000937.1 | 1,90831782 | 3,48432 | 1,08824365 |
| 204887_s_at | PLK4 | NM_014264.1 | 1,90405359 | 3,57836 | 1,35179328 |
| 204520_x_at | BRD1 | NM_014577.1 | 1,90295575 | 3,17884 | 1,35179328 |
| 214657_s_at | TncRNA | AU134977 | 1,89876531 | 4,36117 | 1,35179328 |
| 218663_at | HCAP-G | NM_022346.1 | 1,89393699 | 4,22761 | 1,35179328 |
| 204108_at | NFYA | AL031778 | 1,89170875 | 3,03947 | 1,35179328 |
| 202669_s_at | EFNB2 | U16797.1 | 1,88812353 | 9,61446 | 1,35179328 |

FIG. 9 (Continued)

TABLE 1 (Continued)

| | | | | | |
|---|---|---|---|---|---|
| 219218_at | KIAA1447 | NM_024696.1 | 1,88604486 | 4,27567 | 1,35179328 |
| 211789_s_at | MONDOA | AF312918.1 | 1,88590447 | 11,78537 | 1,35179328 |
| 214472_at | HIST1H3D | NM_003530.1 | 1,88533128 | 6,09618 | 1,35179328 |
| 218585_s_at | RAMP | NM_016448.1 | 1,8841071 | 3,06034 | 1,35179328 |
| 202464_s_at | PFKFB3 | NM_004566.1 | 1,88067802 | 6,73415 | 1,35179328 |
| 215078_at | SOD2 | AL050388.1 | 1,87020398 | 4,53284 | 1,35179328 |
| 204998_s_at | ATF5 | NM_012068.2 | 1,86916003 | 3,69229 | 1,35179328 |
| 222023_at | AKAP13 | AK022014.1 | 1,86668064 | 3,39792 | 1,35179328 |
| 221747_at | TNS | AL046979 | 1,86477105 | 6,85933 | 1,35179328 |
| 202708_s_at | HIST2H2BE | NM_003528.1 | 1,86288092 | 4,22124 | 1,35179328 |
| 209398_at | HIST1H1C | BC002649.1 | 1,85900797 | 4,12314 | 1,35179328 |
| 202095_s_at | BIRC5 | NM_001168.1 | 1,8505345 | 3,22225 | 1,35179328 |
| 204076_at | ENTPD4 | AB002390.11 | 1,84953656 | 3,15943 | 1,35179328 |
| 54037_at | HPS4 | AL041451 | 1,84170888 | 3,99984 | 1,55270497 |
| 204182_s_at | ZNF297B | NM_014007.1 | 1,83835493 | 3,3581 | 1,55270497 |
| 206020_at | SOCS6 | NM_016387.1 | 1,82851337 | 3,29183 | 1,55270497 |
| 222180_at | YES1 | AU147889 | 1,82541551 | 4,63073 | 1,55270497 |
| 214453_s_at | IFI44 | NM_006417.1 | 1,82413467 | 6,23792 | 1,55270497 |
| 207571_x_at | C1orf38 | NM_004848.1 | 1,82363784 | 3,03877 | 1,55270497 |
| 215460_x_at | BRD1 | AL080149.1 | 1,80972344 | 3,04487 | 1,55270497 |
| 201694_s_at | EGR1 | NM_001964.1 | 1,80868355 | 4,44565 | 1,55270497 |
| 213558_at | --- | AB011131.1 | 1,80802989 | 5,72335 | 1,55270497 |
| 215375_x_at | --- | AK023938.1 | 1,805556 | 4,71206 | 1,55270497 |
| 221477_s_at | --- | BF575213 | 1,80529163 | 3,8391 | 1,55270497 |
| 217022_s_at | MGC27165 | S55735.1 | 1,80383405 | 15,37978 | 1,55270497 |
| 209712_at | SLC35D1 | AI769637 | 1,79935516 | 3,37821 | 1,55270497 |
| 210693_at | SPPL2B | BC001788.1 | 1,79701465 | 10,02951 | 1,55270497 |
| 218280_x_at | HIST2H2AA | NM_003516.1 | 1,79338159 | 3,72958 | 1,55270497 |
| 209524_at | HDGFRP3 | NM_016073.1 | 1,78870901 | 6,416 | 1,76597027 |
| 201739_at | SGK | NM_005627.1 | 1,78641926 | 6,0991 | 1,76597027 |
| 203335_at | PHYH | NM_006214.1 | 1,77961388 | 4,56718 | 1,76597027 |
| 202912_at | ADM | NM_001124.1 | 1,77949199 | 4,99498 | 1,76597027 |
| 201829_at | NET1 | AW263232 | 1,77014588 | 3,23043 | 1,76597027 |
| 206940_s_at | POU4F1 | NM_006237.1 | 1,76732008 | 4,89163 | 1,76597027 |
| 214469_at | HIST1H2AE | NM_021052.1 | 1,76245441 | 3,57202 | 1,76597027 |
| 218386_x_at | USP16 | NM_006447.1 | 1,76229432 | 3,06194 | 1,76597027 |
| 213539_at | CD3D | NM_000732.1 | 1,75927104 | 3,03553 | 1,76597027 |
| 210146_x_at | ILT8 /// LILRB2 | AF004231.1 | 1,75848337 | 3,31824 | 1,76597027 |
| 217957_at | GTL3 | NM_013242.1 | 1,75744344 | 3,60621 | 1,76597027 |
| 201681_s_at | DLG5 | AB011155.1 | 1,75682132 | 4,92237 | 1,76597027 |

FIG. 9 (Continued)

TABLE 1 (Continued)

| | | | | | |
|---|---|---|---|---|---|
| 210517_s_at | AKAP12 | AB003476.1 | 1,75428321 | 14,99032 | 1,76597027 |
| 217682_at | PRO0149 | AW503390 | 1,75249893 | 3,20128 | 1,76597027 |
| 208776_at | PSMD11 | BF432873 | 1,75041419 | 3,13414 | 1,76597027 |
| 202580_x_at | FOXM1 | NM_021953.1 | 1,73094724 | 3,72407 | 2,14596689 |
| 214500_at | H2AFY | AF044286.1 | 1,72442037 | 3,75 | 2,14596689 |
| 218662_s_at | HCAP-G | NM_022346.1 | 1,72366417 | 3,30653 | 2,14596689 |
| 212488_at | COL5A1 | N30339 | 1,72147496 | 5,84906 | 2,14596689 |
| 212722_s_at | PTDSR | AK021780.1 | 1,71458803 | 3,43337 | 2,14596689 |
| 218988_at | SLC35E3 | NM_018656.1 | 1,71128356 | 6,28596 | 2,14596689 |
| 206145_at | RHAG | NM_000324.1 | 1,71095519 | 3,04186 | 2,14596689 |
| 201379_s_at | TPD52L2 | NM_003288.1 | 1,70804391 | 3,84491 | 2,14596689 |
| 201540_at | FHL1 | NM_001449.1 | 1,69863393 | 4,26494 | 2,14596689 |
| 205495_s_at | GNLY | NM_006433.2 | 1,69731775 | 3,41689 | 2,14596689 |
| 221773_at | ELK3 | AW575374 | 1,69684215 | 3,59797 | 2,14596689 |
| 205950_s_at | CA1 | NM_001738.1 | 1,68123466 | 6,47394 | 2,14596689 |
| 209087_x_at | MCAM | AF089868.1 | 1,6758921 | 6,73668 | 2,14596689 |
| 212602_at | WDFY3 | AI806395 | 1,67582076 | 3,23426 | 2,14596689 |
| 208930_s_at | ILF3 | BG032366 | 1,67485431 | 3,26901 | 2,14596689 |
| 219918_s_at | ASPM | NM_018123.1 | 1,66056067 | 3,11732 | 2,42250628 |
| 204141_at | TUBB | NM_001069.1 | 1,65837655 | 4,7651 | 2,42250628 |
| 202411_at | IFI27 | NM_005532.1 | 1,65153352 | 11,49501 | 2,42250628 |
| 214583_at | RSC1A1 | AI268381 | 1,63585692 | 3,02207 | 2,42250628 |
| 206937_at | SPTA1 | NM_003126.1 | 1,63359681 | 4,57277 | 2,42250628 |
| 215083_at | PSPC1 | AL049263.1 | 1,6324919 | 4,84915 | 2,42250628 |
| 215589_at | SMURF1 | AK024937.1 | 1,62967202 | 3,09069 | 2,42250628 |
| 38487_at | STAB1 | D87433 | 1,62169393 | 8,53185 | 2,75970495 |
| 220319_s_at | MYLIP | NM_013262.2 | 1,61927198 | 3,74045 | 2,75970495 |
| 218392_x_at | SFXN1 | NM_022754.1 | 1,61921899 | 3,44388 | 2,75970495 |
| 219359_at | FLJ22635 | NM_025092.1 | 1,61718632 | 3,22532 | 2,75970495 |
| 204872_at | TLE4 | NM_007005.1 | 1,61485833 | 3,52492 | 2,75970495 |
| 207980_s_at | CITED2 | NM_006079.1 | 1,60727387 | 3,09635 | 2,75970495 |
| 204438_at | MRC1 | NM_002438.1 | 1,59782488 | 3,95348 | 2,75970495 |
| 212099_at | RHOB | AI263909 | 1,5964639 | 3,38787 | 2,75970495 |
| 203910_at | PARG1 | NM_004815.1 | 1,57857818 | 6,36818 | 2,75970495 |
| 217226_s_at | PRRX1 /// BA108L7.2 | M95929.1 | 1,57552764 | 3,05544 | 2,75970495 |
| 201469_s_at | SHC1 | AI809967 | 1,57523716 | 3,12874 | 2,75970495 |
| 212192_at | KCTD12 | AI718937 | 1,57098197 | 3,80658 | 3,16448023 |
| 209185_s_at | IRS2 | AF073310.1 | 1,55342869 | 3,65866 | 3,16448023 |
| 221748_s_at | TNS | AL046979 | 1,54925369 | 7,63775 | 3,16448023 |

FIG. 9 (Continued)

TABLE 1 (Continued)

| | | | | | |
|---|---|---|---|---|---|
| 203348_s_at | ETV5 | BF060791 | 1,54108903 | 5,05351 | 3,16448023 |
| 206115_at | EGR3 | NM_004430.1 | 1,52117846 | 3,54604 | 3,16448023 |
| 206574_s_at | PTP4A3 | NM_007079.1 | 1,51483044 | 6,38472 | 3,57650927 |
| 202768_at | FOSB | NM_006732.1 | 1,51248489 | 5,76215 | 3,57650927 |
| 36564_at | IBRDC3 | W27419 | 1,50389157 | 3,00358 | 3,57650927 |
| 202908_at | WFS1 | NM_006005.2 | 1,50239785 | 3,13176 | 3,57650927 |
| 219672_at | ERAF | NM_016633.1 | 1,49729743 | 4,59565 | 3,57650927 |
| 202946_s_at | BTBD3 | NM_014962.1 | 1,49531456 | 3,3429 | 3,57650927 |
| 202704_at | TOB1 | AA675892 | 1,49401249 | 3,13365 | 3,57650927 |
| 210299_s_at | FHL1 | AF063002.1 | 1,47593973 | 3,67265 | 3,57650927 |
| 212977_at | CMKOR1 | AI817041 | 1,46058552 | 4,25899 | 3,97317271 |
| 209184_s_at | IRS2 | BF700086 | 1,45794708 | 3,45032 | 3,97317271 |
| 200762_at | DPYSL2 | NM_001386.1 | 1,45445879 | 3,95155 | 3,97317271 |
| 201631_s_at | IER3 | NM_003897.1 | 1,45141631 | 3,80768 | 3,97317271 |
| 205928_at | ZNF443 | NM_005815.1 | 1,43261223 | 3,79283 | 3,97317271 |
| 206724_at | CBX4 | NM_003655.1 | 1,42481346 | 5,22392 | 3,97317271 |
| 201693_s_at | EGR1 | NM_001964.1 | 1,42272131 | 3,45593 | 3,97317271 |
| 205592_at | SLC4A1 | X77737.1 | 1,4211057 | 5,00478 | 3,97317271 |
| 203334_at | DHX8 | NM_004941.1 | 1,41968053 | 3,87406 | 4,35529744 |
| 204066_s_at | CENTG2 | NM_014914.1 | 1,40481153 | 7,59542 | 4,35529744 |
| 212606_at | WDFY3 | AL536319 | 1,38506776 | 3,22317 | 4,35529744 |
| 204914_s_at | SOX11 | AW157202 | 1,37018937 | 16,38105 | 4,74543 |
| 203305_at | F13A1 | NM_000129.2 | 1,36687396 | 3,51935 | 4,74543 |
| 203411_s_at | LMNA | NM_005572.1 | 1,3654064 | 3,38725 | 4,74543 |
| 212181_s_at | NUDT4 | AF191654.2 | 1,36436702 | 3,20227 | 4,74543 |
| 209258_s_at | CSPG6 | AI373676 | 1,3642486 | 3,23332 | 4,74543 |
| 203358_s_at | EZH2 | NM_004456.1 | 1,35584058 | 3,01552 | 4,74543 |
| 207788_s_at | SCAM-1 | NM_005775.1 | 1,33639245 | 3,43555 | 5,24904647 |
| 205220_at | GPR109B | NM_006018.1 | 1,33557629 | 3,94163 | 5,24904647 |
| 215137_at | KIAA0508 | H92070 | 1,3202648 | 3,7195 | 5,24904647 |
| 218625_at | NRN1 | NM_016588.1 | 1,2994504 | 6,54293 | 5,24904647 |
| 220230_s_at | CYB5R2 | NM_016229 | 1,28399362 | 5,49083 | 5,80662657 |
| 200671_s_at | SPTBN1 | N92501 | 1,27721548 | 3,14696 | 5,80662657 |
| 208963_x_at | FADS1 | BG165833 | 1,27440786 | 3,07085 | 5,80662657 |
| 202932_at | YES1 | NM_005433.1 | 1,26445601 | 5,34493 | 5,80662657 |
| 206834_at | HBD | NM_000519.2 | 1,26426354 | 6,44562 | 5,80662657 |
| 212070_at | GPR56 | AL554008 | 1,26108421 | 3,5986 | 5,80662657 |
| 209781_s_at | KHDRBS3 | AF069681.1 | 1,21578364 | 3,75588 | 6,32547517 |
| 221704_s_at | FLJ12750 | BC005882.1 | -1,3654518 | 0,3296 | 5,24904647 |
| 205633_s_at | ALAS1 | NM_000688.1 | -1,4888568 | 0,29478 | 3,16448023 |

FIG. 9 (Continued)

TABLE 1 (Continued)

| | | | | | |
|---|---|---|---|---|---|
| 209480_at | --- | M16276.1 | -1,4921578 | 0,3125 | 3,16448023 |
| 203414_at | MMD | NM_012329.1 | -1,5631444 | 0,28737 | 2,42250628 |
| 203984_s_at | CASP9 | U60521.1 | -1,6627554 | 0,27598 | 1,76597027 |
| 218329_at | PRDM4 | NM_012406.2 | -1,666414 | 0,33124 | 1,76597027 |
| 213831_at | HLA-DQA1 | X00452.1 | -1,6995307 | 0,23025 | 1,55270497 |
| 203749_s_at | RARA | AI806984 | -1,7060512 | 0,32448 | 1,55270497 |
| 202742_s_at | PRKACB | NM_002731.1 | -1,7133449 | 0,312 | 1,55270497 |
| 203143_s_at | KIAA0040 | T79953 | -1,7216633 | 0,30441 | 1,35179328 |
| 202902_s_at | CTSS | NM_004079.1 | -1,7369801 | 0,3008 | 1,35179328 |
| 220306_at | FAM46C | NM_017709.1 | -1,7428841 | 0,33252 | 1,35179328 |
| 203642_s_at | COBLL1 | NM_014900.1 | -1,7505207 | 0,33304 | 1,35179328 |
| 213238_at | ATP10D | AI478147 | -1,7525652 | 0,32668 | 1,35179328 |
| 219228_at | ZNF331 | NM_018555.2 | -1,7554736 | 0,24314 | 1,35179328 |
| 204638_at | ACP5 | NM_001611.2 | -1,7673032 | 0,32697 | 1,08824365 |
| 205027_s_at | MAP3K8 | NM_005204.1 | -1,784629 | 0,27792 | 1,08824365 |
| 210379_s_at | TLK1 | AF162666.1 | -1,784715 | 0,33144 | 1,08824365 |
| 205081_at | CRIP1 | NM_001311.1 | -1,7864215 | 0,32258 | 1,08824365 |
| 213035_at | ANKRD28 | AI081194 | -1,7972045 | 0,31463 | 1,08824365 |
| 204205_at | APOBEC3G | NM_021822.1 | -1,8014431 | 0,3131 | 1,08824365 |
| 207002_s_at | PLAGL1 | NM_002656.1 | -1,8086903 | 0,32223 | 0,8509783 |
| 209829_at | C6orf32 | AB002384.1 | -1,811653 | 0,24595 | 0,8509783 |
| 212632_at | STX7 | N32035 | -1,8163577 | 0,29354 | 0,8509783 |
| 211796_s_at | TRB@ | AF043179.1 | -1,8239565 | 0,33049 | 0,8509783 |
| 209307_at | --- | AB014540.1 | -1,8449986 | 0,32813 | 0,8509783 |
| 208268_at | ADAM28 | NM_021777.1 | -1,8641373 | 0,27561 | 0,8509783 |
| 209281_s_at | ATP2B1 | M95541.1 | -1,8668447 | 0,3082 | 0,8509783 |
| 204917_s_at | MLLT3 | AV756536 | -1,8714698 | 0,32788 | 0,8509783 |
| 215925_s_at | CD72 | AF283777.2 | -1,876355 | 0,31183 | 0,8509783 |
| 213572_s_at | SERPINB1 | AI554300 | -1,8858731 | 0,31755 | 0,64064579 |
| 204419_x_at | HBG2 | NM_000184.1 | -1,8873938 | 0,32231 | 0,64064579 |
| 202719_s_at | TES | BC001451.1 | -1,8877355 | 0,32827 | 0,64064579 |
| 209191_at | MGC4083 | BC002654.1 | -1,8911168 | 0,32367 | 0,64064579 |
| 206177_s_at | ARG1 | NM_000045.2 | -1,8916181 | 0,21548 | 0,64064579 |
| 211105_s_at | NFATC1 | U80918.1 | -1,8979026 | 0,333 | 0,64064579 |
| 208195_at | TTN | NM_003319.1 | -1,9110792 | 0,30285 | 0,64064579 |
| 214437_s_at | SHMT2 | NM_005412.1 | -1,9184258 | 0,29918 | 0,64064579 |
| 213515_x_at | HBG2 | AI133353 | -1,9189866 | 0,30354 | 0,64064579 |
| 222001_x_at | --- | AI160126 | -1,9254462 | 0,30345 | 0,64064579 |
| 209681_at | SLC19A2 | AF153330.1 | -1,9421324 | 0,24407 | 0,64064579 |
| 205603_s_at | DIAPH2 | NM_007309.1 | -1,94722 | 0,29084 | 0,64064579 |
| 204362_at | SCAP2 | NM_003930.1 | -1,948626 | 0,30068 | 0,64064579 |

FIG. 9 (Continued)

TABLE 1 (Continued)

| | | | | | |
|---|---|---|---|---|---|
| 217235_x_at | --- | D84140.1 | -1,9490856 | 0,31277 | 0,64064579 |
| 210981_s_at | GRK6 | AF040751.1 | -1,950177 | 0,31474 | 0,64064579 |
| 218718_at | PDGFC | NM_016205.1 | -1,9566146 | 0,26637 | 0,64064579 |
| 208998_at | UCP2 | U94592.1 | -1,9578147 | 0,28349 | 0,4885859 |
| 209789_at | CORO2B | AB010098.1 | -1,9682015 | 0,3121 | 0,4885859 |
| 216899_s_at | SCAP2 | AC003999 | -1,9689761 | 0,29432 | 0,4885859 |
| 212459_x_at | SUCLG2 | BF593940 | -1,9783696 | 0,26121 | 0,4885859 |
| 211352_s_at | NCOA3 | U80737.1 | -1,9818656 | 0,24285 | 0,4885859 |
| 201012_at | ANXA1 | NM_000700.1 | -1,9855325 | 0,23595 | 0,4885859 |
| 206060_s_at | PTPN22 | NM_015967.1 | -1,9922691 | 0,28793 | 0,4885859 |
| 201859_at | PRG1 | NM_002727.1 | -1,9953881 | 0,30177 | 0,4885859 |
| 44790_s_at | C13orf18 | AI129310 | -1,9955085 | 0,29409 | 0,4885859 |
| 203378_at | PCF11 | AB020631.1 | -1,9970385 | 0,30001 | 0,4885859 |
| 201413_at | HSD17B4 | NM_000414.1 | -1,9992847 | 0,27511 | 0,4885859 |
| 217168_s_at | HERPUD1 | AF217990.1 | -2,003728 | 0,27162 | 0,4885859 |
| 211597_s_at | HOP | AB059408.1 | -2,0084257 | 0,29664 | 0,4885859 |
| 205859_at | LY86 | NM_004271.1 | -2,0118558 | 0,29371 | 0,4885859 |
| 215772_x_at | SUCLG2 | AL050226.1 | -2,0201646 | 0,26009 | 0,4885859 |
| 214467_at | GPR65 | NM_003608.1 | -2,0266205 | 0,27061 | 0,27903683 |
| 221474_at | MRLC2 | U26162.1 | -2,0266882 | 0,29955 | 0,27903683 |
| 203802_x_at | WBSCR20A | NM_018044.1 | -2,0287375 | 0,29376 | 0,27903683 |
| 212829_at | --- | BE878277 | -2,0293478 | 0,31467 | 0,27903683 |
| 213142_x_at | LOC54103 | AV700415 | -2,0342101 | 0,29254 | 0,27903683 |
| 219551_at | EAF2 | NM_018456.1 | -2,0361755 | 0,28278 | 0,27903683 |
| 217963_s_at | NGFRAP1 | NM_014380.1 | -2,0370976 | 0,29659 | 0,27903683 |
| 201425_at | ALDH2 | NM_000690.1 | -2,046114 | 0,2559 | 0,27903683 |
| 212098_at | LOC151162 | AL134724 | -2,0544595 | 0,31834 | 0,27903683 |
| 201034_at | ADD3 | BE545756 | -2,0590684 | 0,32388 | 0,27903683 |
| 212256_at | GALNT10 | BE906572 | -2,0643555 | 0,2748 | 0,27903683 |
| 203640_at | MBNL2 | BE328496 | -2,0675352 | 0,2547 | 0,27903683 |
| 212956_at | KIAA0882 | AI348094 | -2,0678262 | 0,21488 | 0,27903683 |
| 212631_at | STX7 | AI566082 | -2,0729795 | 0,26395 | 0,27903683 |
| 205863_at | S100A12 | NM_005621.1 | -2,0757198 | 0,25534 | 0,27903683 |
| 209412_at | TMEM1 | U61500.1 | -2,0808939 | 0,24971 | 0,27903683 |
| 209318_x_at | PLAGL1 | U72621.3 | -2,0949641 | 0,27742 | 0,27903683 |
| 203394_s_at | HES1 | BE973687 | -2,1064128 | 0,18569 | 0,27903683 |
| 220933_s_at | ZCCHC6 | NM_024617.1 | -2,1091149 | 0,27198 | 0,27903683 |
| 216510_x_at | IGHG1 | AB035175 | -2,1171898 | 0,22967 | 0,16349815 |
| 201753_s_at | ADD3 | NM_019903.1 | -2,1173592 | 0,29813 | 0,16349815 |
| 202741_at | PRKACB | AA130247 | -2,119044 | 0,2506 | 0,16349815 |

FIG. 9 (Continued)

TABLE 1 (Continued)

| | | | | | |
|---|---|---|---|---|---|
| 213603_s_at | RAC2 | BE138888 | -2,1220993 | 0,30202 | 0,16349815 |
| 218870_at | ARHGAP15 | NM_018460.1 | -2,1371511 | 0,3103 | 0,16349815 |
| 206207_at | CLC | NM_001828.3 | -2,1519798 | 0,24909 | 0,16349815 |
| 212589_at | RRAS2 | AI753792 | -2,1523792 | 0,25268 | 0,16349815 |
| 213975_s_at | LYZ /// LILRB1 | AV711904 | -2,153662 | 0,24428 | 0,16349815 |
| 217157_x_at | --- | AF103530.1 | -2,1559669 | 0,28377 | 0,16349815 |
| 213106_at | ATP8A1 | AI769688 | -2,1620319 | 0,31012 | 0,16349815 |
| 202720_at | TES | NM_015641.1 | -2,1678434 | 0,32101 | 0,16349815 |
| 201689_s_at | TPD52 | BE974098 | -2,1696461 | 0,2365 | 0,16349815 |
| 213309_at | PLCL2 | AL117515.1 | -2,1754973 | 0,30871 | 0,16349815 |
| 217179_x_at | LOC96610 | X79782.1 | -2,1810245 | 0,27386 | 0,16349815 |
| 203765_at | GCA | NM_012198.1 | -2,1970141 | 0,26356 | 0,16349815 |
| 222150_s_at | LOC54103 | AK026747.1 | -2,2022667 | 0,26712 | 0,16349815 |
| 218628_at | CGI-116 | NM_016053.1 | -2,2027508 | 0,24487 | 0,16349815 |
| 216218_s_at | PLCL2 | AK023546.1 | -2,2030387 | 0,25073 | 0,16349815 |
| 201302_at | ANXA4 | NM_001153.2 | -2,21127 | 0,23787 | 0,16349815 |
| 205632_s_at | PIP5K1B | NM_003558.1 | -2,215701 | 0,19355 | 0,16349815 |
| 34210_at | CDW52 | N90866 | -2,2231508 | 0,26397 | 0,16349815 |
| 207700_s_at | NCOA3 | NM_006534.1 | -2,2282672 | 0,29974 | 0,16349815 |
| 203923_s_at | CYBB | NM_000397.2 | -2,2336068 | 0,23537 | 0,16349815 |
| 205419_at | EBI2 | NM_004951.1 | -2,2362291 | 0,24116 | 0,16349815 |
| 203791_at | DMXL1 | NM_005509.2 | -2,2406239 | 0,22286 | 0,16349815 |
| 208456_s_at | RRAS2 | NM_012250.1 | -2,2429072 | 0,21214 | 0,16349815 |
| 201752_s_at | ADD3 | AI763123 | -2,2435235 | 0,27009 | 0,16349815 |
| 205804_s_at | T3JAM | NM_025228.1 | -2,2510239 | 0,24583 | 0,16349815 |
| 205882_x_at | ADD3 | AI818488 | -2,2563882 | 0,28313 | 0,16349815 |
| 212311_at | KIAA0746 | AA522514 | -2,2634404 | 0,26205 | 0,16349815 |
| 217995_at | SQRDL | NM_021199.1 | -2,2670103 | 0,25799 | 0,16349815 |
| 214916_x_at | MGC27165 /// IGH@ /// IGHG1 | BG340548 | -2,2767861 | 0,25068 | 0,16349815 |
| 202295_s_at | CTSH | NM_004390.1 | -2,276994 | 0,2628 | 0,16349815 |
| 201690_s_at | TPD52 | AA524023 | -2,2863886 | 0,23328 | 0,16349815 |
| 200965_s_at | ABLIM1 | NM_006720.1 | -2,2877354 | 0,27327 | 0,16349815 |
| 204057_at | --- | AI073984 | -2,2925265 | 0,24952 | 0,16349815 |
| 208438_s_at | FGR | NM_005248.1 | -2,2947732 | 0,24907 | 0,16349815 |
| 211635_x_at | --- | M24670.1 | -2,2993118 | 0,23681 | 0,16349815 |
| 205306_x_at | KMO | AI074145 | -2,3036797 | 0,24522 | 0,16349815 |
| 213702_x_at | ASAH1 | AI934569 | -2,3041594 | 0,3024 | 0,16349815 |
| 205659_at | HDAC9 | NM_014707.1 | -2,3182874 | 0,25308 | 0,16349815 |

FIG. 9 (Continued)

TABLE 1 (Continued)

| | | | | | |
|---|---|---|---|---|---|
| 204207_s_at | RNGTT | NM_003800.1 | -2,3223278 | 0,30649 | 0,16349815 |
| 202863_at | SP100 | NM_003113.1 | -2,3343796 | 0,28192 | 0,16349815 |
| 209761_s_at | SP110 | AA969194 | -2,3350711 | 0,27456 | 0,16349815 |
| 204174_at | ALOX5AP | NM_001629.1 | -2,3406345 | 0,25479 | 0,16349815 |
| 209451_at | TANK | U59863.1 | -2,3443608 | 0,17613 | 0,16349815 |
| 221004_s_at | ITM2C | NM_030926.1 | -2,3496129 | 0,25651 | 0,16349815 |
| 209765_at | ADAM19 | Y13786.2 | -2,3522539 | 0,25969 | 0,16349815 |
| 219054_at | FLJ14054 | NM_024563.1 | -2,3542854 | 0,262 | 0,16349815 |
| 207819_s_at | ABCB4 | NM_000443.2 | -2,3584146 | 0,19566 | 0,16349815 |
| 201462_at | SCRN1 | NM_014766.1 | -2,3810645 | 0,22571 | 0,16349815 |
| 204072_s_at | 13CDNA73 | NM_023037.1 | -2,3830142 | 0,20255 | 0,16349815 |
| 214836_x_at | --- | BG536224 | -2,3888604 | 0,21891 | 0,16349815 |
| 213888_s_at | T3JAM | AL022398 | -2,4151228 | 0,20028 | 0,16349815 |
| 201779_s_at | RNF13 | AF070558.1 | -2,42964 | 0,2666 | 0,16349815 |
| 219375_at | CEPT1 | NM_006090.1 | -2,4393229 | 0,26203 | 0,16349815 |
| 217480_x_at | --- | M20812 | -2,4415209 | 0,289 | 0,16349815 |
| 204208_at | RNGTT | NM_003800.1 | -2,4554659 | 0,20138 | 0,16349815 |
| 216853_x_at | --- | AF234255.1 | -2,4763598 | 0,22685 | 0,16349815 |
| 204960_at | PTPRCAP | NM_005608.1 | -2,4864487 | 0,25732 | 0,16349815 |
| 208296_x_at | TNFAIP8 | NM_014350.1 | -2,488662 | 0,18674 | 0,16349815 |
| 204661_at | CDW52 | NM_001803.1 | -2,4927321 | 0,22283 | 0,16349815 |
| 209762_x_at | SP110 | AF280094.1 | -2,5006403 | 0,24801 | 0,16349815 |
| 221602_s_at | TOSO | AF057557.1 | -2,5065789 | 0,17979 | 0,16349815 |
| 216491_x_at | --- | U80139 | -2,5124667 | 0,1331 | 0,16349815 |
| 208012_x_at | SP110 | NM_004509 | -2,512864 | 0,23595 | 0,16349815 |
| 202478_at | TRIB2 | NM_021643.1 | -2,5156607 | 0,16963 | 0,16349815 |
| 215621_s_at | IGHD | BG340670 | -2,5173083 | 0,16271 | 0,16349815 |
| 56256_at | SIDT2 | AA150165 | -2,5362795 | 0,26971 | 0,16349815 |
| 202080_s_at | OIP106 | NM_014965.1 | -2,5447824 | 0,21781 | 0,16349815 |
| 210140_at | CST7 | AF031824.1 | -2,5486881 | 0,13466 | 0,16349815 |
| 211637_x_at | --- | L23516.1 | -2,5502577 | 0,15651 | 0,16349815 |
| 210279_at | GPR18 | AF261135.1 | -2,5533626 | 0,17306 | 0,16349815 |
| 219014_at | PLAC8 | NM_016619.1 | -2,5560972 | 0,23502 | 0,16349815 |
| 203021_at | SLPI | NM_003064.1 | -2,5608432 | 0,16206 | 0,16349815 |
| 216207_x_at | IGKV1D-13 | AW408194 | -2,5809492 | 0,21843 | 0,16349815 |
| 206726_at | PGDS | NM_014485.1 | -2,5812358 | 0,18141 | 0,16349815 |
| 214768_x_at | --- | BG540628 | -2,5841903 | 0,17799 | 0,16349815 |
| 201780_s_at | RNF13 | NM_007282.1 | -2,5842805 | 0,22616 | 0,16349815 |
| 202864_s_at | SP100 | AI695173 | -2,59353 | 0,22761 | 0,16349815 |
| 202732_at | PKIG | NM_007066.1 | -2,5972088 | 0,17704 | 0,16349815 |
| 219032_x_at | OPN3 | NM_014322.1 | -2,6018487 | 0,21027 | 0,16349815 |

FIG. 9 (Continued)

TABLE 1 (Continued)

| | | | | | |
|---|---|---|---|---|---|
| 217762_s_at | RAB31 | BE789881 | -2,6023214 | 0,17369 | 0,16349815 |
| 204004_at | PAWR | AI336206 | -2,6131395 | 0,16128 | 0,16349815 |
| 201494_at | PRCP | NM_005040.1 | -2,6216912 | 0,21878 | 0,16349815 |
| 202443_x_at | NOTCH2 | AA291203 | -2,6246233 | 0,24239 | 0,16349815 |
| 217764_s_at | RAB31 | AF183421. | -2,638059 | 0,1562 | 0,16349815 |
| 221601_s_at | TOSO | AI084226 | -2,6418038 | 0,19047 | 0,16349815 |
| 201858_s_at | PRG1 | J03223.1 | -2,6475718 | 0,14352 | 0,16349815 |
| 214084_x_at | NCF1 | AW072388 | -2,6533435 | 0,17866 | 0,16349815 |
| 200982_s_at | ANXA6 | NM_001155.2 | -2,6580372 | 0,14507 | 0,16349815 |
| 222285_at | IGHD | AW134608 | -2,6588476 | 0,1584 | 0,16349815 |
| 218100_s_at | ESRRBL1 | NM_018010.1 | -2,6595168 | 0,22597 | 0,16349815 |
| 208771_s_at | LTA4H | J02959.1 | -2,6626082 | 0,24546 | 0,16349815 |
| 207616_s_at | TANK | NM_004180.1 | -2,6654073 | 0,21818 | 0,16349815 |
| 215967_s_at | LY9 | AL582804 | -2,6907423 | 0,13833 | 0,16349815 |
| 201079_at | SYNGR2 | NM_004710.1 | -2,6969455 | 0,20309 | 0,16349815 |
| 203037_s_at | MTSS1 | NM_014751.1 | -2,6992825 | 0,21008 | 0,16349815 |
| 219667_s_at | BANK1 | NM_017935.1 | -2,7113431 | 0,19171 | 0,16349815 |
| 204961_s_at | NCF1 | NM_000265.1 | -2,7250404 | 0,14094 | 0,16349815 |
| 211138_s_at | KMO | BC005297.1 | -2,7423324 | 0,19345 | 0,16349815 |
| 212377_s_at | NOTCH2 | AU158495 | -2,745543 | 0,1981 | 0,16349815 |
| 210754_s_at | LYN | M79321.1 | -2,746282 | 0,18446 | 0,16349815 |
| 204971_at | CSTA | NM_005213.1 | -2,7516336 | 0,12683 | 0,16349815 |
| 209422_at | C20orf104 | AL109965 | -2,7540805 | 0,1801 | 0,16349815 |
| 217227_x_at | IGLC2 /// IGLV@ | X93006.1 | -2,756869 | 0,1591 | 0,16349815 |
| 221059_s_at | COTL1 | NM_021615.1 | -2,7777783 | 0,20968 | 0,16349815 |
| 201301_s_at | ANXA4 | BC000182.1 | -2,7799471 | 0,15827 | 0,16349815 |
| 221671_x_at | IGKC | M63438.1 | -2,7806271 | 0,17098 | 0,16349815 |
| 201998_at | SIAT1 | AI743792 | -2,7910734 | 0,17692 | 0,16349815 |
| 210260_s_at | TNFAIP8 | BC005352.1 | -2,8004856 | 0,16996 | 0,16349815 |
| 202391_at | BASP1 | NM_006317.1 | -2,8128156 | 0,16876 | 0,16349815 |
| 209369_at | ANXA3 | M63310.1 | -2,8453182 | 0,08589 | 0,16349815 |
| 214615_at | P2RY10 | NM_014499.1 | -2,8498426 | 0,15433 | 0,16349815 |
| 217388_s_at | KYNU | D55639.1 | -2,8702074 | 0,13208 | 0,16349815 |
| 221766_s_at | FAM46A | AW246673 | -2,8809726 | 0,09713 | 0,16349815 |
| 202626_s_at | LYN | NM_002350.1 | -2,8896131 | 0,14905 | 0,16349815 |
| 211650_x_at | IGHG1 | L34164.1 | -2,8918172 | 0,11964 | 0,16349815 |
| 209138_x_at | --- | M87790.1 | -2,925698 | 0,17022 | 0,16349815 |
| 214370_at | --- | AW238654 | -2,927921 | 0,12845 | 0,16349815 |
| 205513_at | TCN1 | NM_001062.1 | -2,9345749 | 0,11333 | 0,16349815 |

FIG. 9 (Continued)

TABLE 1 (Continued)

| | | | | | |
|---|---|---|---|---|---|
| 220570_at | RETN | NM_020415.2 | -2,9949661 | 0,09347 | 0,16349815 |
| 214039_s_at | LAPTM4B | T15777 | -3,036504 | 0,10619 | 0,16349815 |
| 202625_at | --- | AI356412 | -3,0731516 | 0,15248 | 0,16349815 |
| 214669_x_at | --- | BG485135 | -3,0813668 | 0,128 | 0,16349815 |
| 214777_at | --- | BG482805 | -3,0954891 | 0,11394 | 0,16349815 |
| 212954_at | DYRK4 | AF263541.1 | -3,0967577 | 0,15107 | 0,16349815 |
| 209396_s_at | CHI3L1 | M80927.1 | -3,1224408 | 0,07257 | 0,16349815 |
| 213674_x_at | IGHD | AI858004 | -3,1397929 | 0,10861 | 0,16349815 |
| 217763_s_at | RAB31 | NM_006868.1 | -3,1696291 | 0,10958 | 0,16349815 |
| 205624_at | CPA3 | NM_001870.1 | -3,2180248 | 0,09458 | 0,16349815 |
| 213566_at | RNASE6 | NM_005615.1 | -3,2290877 | 0,10537 | 0,16349815 |
| 206310_at | SPINK2 | NM_021114.1 | -3,3054564 | 0,0973 | 0,16349815 |
| 207777_s_at | SP140 | NM_007237.1 | -3,3058881 | 0,13918 | 0,16349815 |
| 204192_at | CD37 | NM_001774.1 | -3,306082 | 0,13734 | 0,16349815 |
| 221239_s_at | SPAP1 | NM_030764.1 | -3,317938 | 0,09367 | 0,16349815 |
| 212314_at | KIAA0746 | AB018289.1 | -3,3374545 | 0,13973 | 0,16349815 |
| 221586_s_at | E2F5 | U31556.1 | -3,3758635 | 0,09388 | 0,16349815 |
| 216984_x_at | --- | D84143.1 | -3,4169833 | 0,10208 | 0,16349815 |
| 219073_s_at | OSBPL10 | NM_017784.1 | -3,4606223 | 0,09788 | 0,16349815 |
| 210889_s_at | FCGR2B | M31933.1 | -3,4615304 | 0,08966 | 0,16349815 |
| 211645_x_at | --- | M85256.1 | -3,4664742 | 0,10956 | 0,16349815 |
| 203535_at | S100A9 | NM_002965.2 | -3,4885043 | 0,0718 | 0,16349815 |
| 216401_x_at | --- | AJ408433 | -3,496782 | 0,08904 | 0,16349815 |
| 202917_s_at | S100A8 | NM_002964.2 | -3,5432659 | 0,08484 | 0,16349815 |
| 206111_at | RNASE2 | NM_002934.1 | -3,6073832 | 0,0523 | 0,16349815 |
| 205997_at | ADAM28 | NM_014265.1 | -3,6231814 | 0,08078 | 0,16349815 |
| 219574_at | --- | NM_017923.1 | -3,6989155 | 0,07598 | 0,16349815 |
| 205544_s_at | CR2 | NM_001877.1 | -3,7416193 | 0,05435 | 0,16349815 |
| 212768_s_at | OLFM4 | AL390736 | -3,7832467 | 0,04318 | 0,16349815 |
| 216576_x_at | --- | AF103529.1 | -3,9371736 | 0,07815 | 0,16349815 |
| 212531_at | LCN2 | NM_005564.1 | -3,9427128 | 0,02868 | 0,16349815 |
| 210538_s_at | BIRC3 | U37546.1 | -4,0159506 | 0,06331 | 0,16349815 |
| 215176_x_at | --- | AW404894 | -4,0997831 | 0,06927 | 0,16349815 |
| 218404_at | SNX10 | NM_013322.1 | -4,2513135 | 0,05678 | 0,16349815 |
| 207341_at | PRTN3 | M_002777.2 | -4,3467873 | 0,02684 | 0,16349815 |
| 206851_at | RNASE3 | NM_002935.1 | -4,4819571 | 0,03625 | 0,16349815 |
| 204351_at | S100P | NM_005980.1 | -4,583047 | 0,02574 | 0,16349815 |
| 214575_s_at | AZU1 | NM_001700.1 | -4,6144521 | 0,0225 | 0,16349815 |
| 206126_at | BLR1 | NM_001716.1 | -4,6945968 | 0,03407 | 0,16349815 |
| 210254_at | MS4A3 | L35848.1 | -4,7509342 | 0,02102 | 0,16349815 |

FIG. 9 (Continued)

TABLE 1 (Continued)

| | | | | | |
|---|---|---|---|---|---|
| 205653_at | CTSG | NM_001911.1 | -4,955247 | 0,02528 | 0,16349815 |
| 206676_at | CEACAM8 | M33326.1 | -5,0983693 | 0,01301 | 0,16349815 |
| 205557_at | BPI | NM_001725.1 | -5,4228754 | 0,01379 | 0,16349815 |
| 202018_s_at | LTF | NM_002343.1 | -5,6154039 | 0,01101 | 0,16349815 |
| 206871_at | ELA2 | NM_001972.1 | -5,9699202 | 0,00808 | 0,16349815 |
| 207269_at | DEFA4 | NM_001925.1 | -6,3686998 | 0,01044 | 0,16349815 |
| 210244_at | CAMP | U19970.1 | -6,626962 | 0,00773 | 0,16349815 |
| 205033_s_at | DEFA3 /// DEFA1 | NM_004084.2 | -7,1134725 | 0,01009 | 0,16349815 |

(END TABLE 1)

FIG. 10

Table 2

| uniqid | Gene Symbol | Gene ID | Score(d) | Fold Change | q-value (%) |
|---|---|---|---|---|---|
| 219686_at | STK32B | NM_018401.1 | 5,21258795 | 70,50159 | 0,16349815 |
| 203821_at | DTR | NM_001945.1 | 4,58196056 | 26,14573 | 0,16349815 |
| 206548_at | FLJ23556 | NM_024880.1 | 4,51016439 | 22,43302 | 0,16349815 |
| 207030_s_at | CSRP2 | NM_001321.1 | 4,42194787 | 32,12154 | 0,16349815 |
| 214455_at | HIST1H2BC | NM_003526.1 | 4,08410483 | 13,74617 | 0,16349815 |
| 204083_s_at | TPM2 | NM_003289.1 | 3,80317072 | 12,16817 | 0,16349815 |
| 38037_at | DTR | M60278 | 3,73341094 | 15,75834 | 0,16349815 |
| 201329_s_at | ETS2 | NM_005239.1 | 3,63741689 | 13,10507 | 0,16349815 |
| 202481_at | DHRS3 | NM_004753.1 | 3,54350956 | 9,08517 | 0,16349815 |
| 222303_at | --- | AV700891 | 3,38335076 | 12,76201 | 0,16349815 |
| 216035_x_at | TCF7L2 | AV721430 | 3,38229053 | 6,89967 | 0,16349815 |
| 212013_at | D2S448 | D86983.1 | 3,36264562 | 8,49028 | 0,16349815 |
| 211341_at | POU4F1 | L20433.1 | 3,35467618 | 36,79822 | 0,16349815 |
| 203373_at | SOCS2 | NM_003877.1 | 3,31104953 | 8,22452 | 0,16349815 |
| 208893_s_at | DUSP6 | NM_001946.1 | 3,29663499 | 27,24485 | 0,16349815 |
| 202242_at | TM4SF2 | NM_004615.1 | 3,26806143 | 12,25609 | 0,16349815 |
| 215597_x_at | MYST4 | AK021415 | 3,26763189 | 6,86309 | 0,16349815 |
| 203325_s_at | COL5A1 | NM_000093.1 | 3,22968817 | 10,06737 | 0,16349815 |
| 221349_at | VPREB1 | NM_007128.1 | 3,17175847 | 29,65737 | 0,16349815 |
| 203372_s_at | SOCS2 | NM_003877.1 | 3,16955259 | 8,798 | 0,16349815 |
| 201565_s_at | ID2 | NM_002166.1 | 3,12376982 | 12,91039 | 0,16349815 |
| 215743_at | NMT2 | AL134489 | 3,1176101 | 5,72186 | 0,16349815 |
| 218051_s_at | FLJ12442 | NM_022908.1 | 3,05909223 | 5,98974 | 0,16349815 |
| 204011_at | SPRY2 | NM_005842.1 | 3,02096517 | 10,09141 | 0,16349815 |
| 209025_s_at | SYNCRIP | AF037448.1 | 3,01562031 | 5,24967 | 0,16349815 |
| 201830_s_at | NET1 | NM_005863.1 | 2,99849305 | 9,67614 | 0,16349815 |
| 218311_at | MAP4K3 | NM_003618.1 | 2,97258701 | 5,53905 | 0,16349815 |
| 211052_s_at | TBCD | BC006364.1 | 2,93936985 | 9,84326 | 0,16349815 |
| 218402_s_at | HPS4 | NM_022081.1 | 2,93527602 | 6,88468 | 0,16349815 |
| 201170_s_at | BHLHB2 | NM_003670.1 | 2,90396696 | 8,17656 | 0,16349815 |
| 208890_s_at | PLXNB2 | BC004542.1 | 2,87652685 | 9,1662 | 0,16349815 |
| 218880_at | FOSL2 | NM_024530.1 | 2,87082903 | 17,10764 | 0,16349815 |
| 215398_at | HRPT2 | AF038194.1 | 2,83312103 | 5,52282 | 0,16349815 |
| 204759_at | CHC1L | NM_001268.1 | 2,81620248 | 5,60794 | 0,16349815 |
| 201566_x_at | ID2 | D13891.1 | 2,77550424 | 7,02998 | 0,16349815 |

FIG. 10 (Continued)

Table 2 (Continued)

| | | | | | |
|---|---|---|---|---|---|
| 209568_s_at | RGL1 | AF186779.1 | 2,77416962 | 7,1704 | 0,16349815 |
| 205290_s_at | BMP2 | NM_001200.1 | 2,77089326 | 14,76706 | 0,16349815 |
| 214623_at | SHFM3P1 | AA845710 | 2,74311404 | 5,27094 | 0,16349815 |
| 220359_s_at | ARPP-21 | NM_016300.1 | 2,72887773 | 22,4658 | 0,16349815 |
| 215218_s_at | C19orf14 | AC004144 | 2,72185346 | 4,33475 | 0,16349815 |
| 216511_s_at | TCF7L2 | AJ270770 | 2,70431774 | 4,82314 | 0,16349815 |
| 220918_at | C21orf96 | NM_025143.1 | 2,7010981 | 5,86336 | 0,16349815 |
| 211066_x_at | PCDHGA3 | BC006439.1 | 2,69566326 | 5,46935 | 0,16349815 |
| 214696_at | MGC14376 | AF070569.1 | 2,685678 | 7,80167 | 0,16349815 |
| 201401_s_at | ADRBK1 | NM_001619.2 | 2,68551594 | 6,12232 | 0,16349815 |
| 220085_at | HELLS | NM_018063.1 | 2,62632619 | 4,7809 | 0,16349815 |
| 207697_x_at | LILRB2 | NM_005874.1 | 2,62124408 | 3,99063 | 0,16349815 |
| 213827_at | SNX26 | AL137579.1 | 2,61659514 | 4,48069 | 0,16349815 |
| 218856_at | TNFRSF21 | NM_016629.1 | 2,59998917 | 8,10701 | 0,16349815 |
| 212012_at | D2S448 | BF342851 | 2,59972845 | 5,26138 | 0,16349815 |
| 214761_at | ZNF423 | AW149417 | 2,59825698 | 6,10268 | 0,16349815 |
| 218589_at | P2RY5 | NM_005767.1 | 2,59798335 | 7,70067 | 0,16349815 |
| 216766_at | PRKCE | AK025152.1 | 2,57824036 | 3,88585 | 0,16349815 |
| 219493_at | SHCBP1 | NM_024745.1 | 2,56130388 | 5,29014 | 0,16349815 |
| 209210_s_at | PLEKHC1 | Z24725.1 | 2,55950934 | 14,11969 | 0,16349815 |
| 208891_at | DUSP6 | BC003143.1 | 2,55507866 | 8,10323 | 0,16349815 |
| 212759_s_at | TCF7L2 | AI703074 | 2,54503968 | 6,00555 | 0,16349815 |
| 215223_s_at | SOD2 | W46388 | 2,53570374 | 7,56057 | 0,16349815 |
| 220448_at | KCNK12 | NM_022055.1 | 2,52151072 | 23,4441 | 0,16349815 |
| 207705_s_at | KIAA0980 | NM_025176.1 | 2,51969499 | 6,56891 | 0,16349815 |
| 209035_at | MDK | M69148.1 | 2,5184133 | 14,23192 | 0,16349815 |
| 202392_s_at | PISD | NM_014338.1 | 2,49570169 | 3,78572 | 0,16349815 |
| 213008_at | FLJ10719 | BG403615 | 2,49261192 | 3,88768 | 0,16349815 |
| 221840_at | PTPRE | AA775177 | 2,47980234 | 5,58391 | 0,16349815 |
| 205135_s_at | NUFIP1 | NM_012345.1 | 2,46539741 | 3,78909 | 0,16349815 |
| 209079_x_at | PCDHGA3 | AF152318.1 | 2,45452854 | 5,80181 | 0,16349815 |
| 215028_at | SEMA6A | AB002438.1 | 2,45082987 | 12,36692 | 0,16349815 |
| 203350_at | AP1G1 | NM_001128.1 | 2,44797136 | 4,99958 | 0,16349815 |
| 211101_x_at | LILRA2 | U82276.1 | 2,4401662 | 5,80157 | 0,16349815 |
| 201416_at | SOX4 | BG528420 | 2,42537008 | 5,18605 | 0,16349815 |
| 202519_at | MONDOA | NM_014938.1 | 2,4234139 | 3,95918 | 0,16349815 |
| 205983_at | DPEP1 | NM_004413.1 | 2,41992701 | 7,98064 | 0,16349815 |
| 201418_s_at | SOX4 | NM_003107.1 | 2,41664283 | 4,8183 | 0,16349815 |
| 217534_at | --- | AA845825 | 2,4155383 | 3,80221 | 0,16349815 |

FIG. 10 (Continued)

Table 2 (Continued)

| | | | | | |
|---|---|---|---|---|---|
| 220728_at | --- | NM_025120.1 | 2,41540187 | 4,18975 | 0,16349815 |
| 204109_s_at | NFYA | NM_002505.2 | 2,40928668 | 3,75718 | 0,16349815 |
| 204822_at | TTK | NM_003318.1 | 2,40884455 | 3,20765 | 0,16349815 |
| 34726_at | CACNB3 | U07139 | 2,39114999 | 3,76677 | 0,16349815 |
| 211924_s_at | PLAUR | AY029180.1 | 2,37317631 | 4,86998 | 0,16349815 |
| 212761_at | TCF7L2 | AI949687 | 2,37043268 | 4,76268 | 0,16349815 |

(END TABLE 2)

FIG. 11

Table 3

| uniqid | Gene Symbol | Gene ID | Score(d) | Fold Change | q-value (%) |
|---|---|---|---|---|---|
| 205033_s_at | DEFA3 /// DEFA1 | NM_004084.2 | -7,1134725 | 0,01009 | 0,16349815 |
| 202018_s_at | LTF | NM_002343.1 | -5,6154039 | 0,01101 | 0,16349815 |
| 206126_at | BLR1 | NM_001716.1 | -4,6945968 | 0,03407 | 0,16349815 |
| 218404_at | SNX10 | NM_013322.1 | -4,2513135 | 0,05678 | 0,16349815 |
| 215176_x_at | --- | AW404894 | -4,0997831 | 0,06927 | 0,16349815 |
| 216576_x_at | --- | AF103529.1 | -3,9371736 | 0,07815 | 0,16349815 |
| 219574_at | --- | NM_017923.1 | -3,6989155 | 0,07598 | 0,16349815 |
| 205997_at | ADAM28 | NM_021778.1 | -3,6231814 | 0,08078 | 0,16349815 |
| 202917_s_at | S100A8 | NM_002964.2 | -3,5432659 | 0,08484 | 0,16349815 |
| 216401_x_at | --- | AJ408433 | -3,496782 | 0,08904 | 0,16349815 |
| 211645_x_at | --- | M85256.1 | -3,4664742 | 0,10956 | 0,16349815 |
| 210889_s_at | FCGR2B | M31933.1 | -3,4615304 | 0,08966 | 0,16349815 |
| 219073_s_at | OSBPL10 | NM_017784.1 | -3,4606223 | 0,09788 | 0,16349815 |
| 216984_x_at | --- | D84143.1 | -3,4169833 | 0,10208 | 0,16349815 |
| 221586_s_at | E2F5 | U31556.1 | -3,3758635 | 0,09388 | 0,16349815 |
| 212314_at | KIAA0746 | AB018289.1 | -3,3374545 | 0,13973 | 0,16349815 |
| 221239_s_at | SPAP1 | NM_030764.1 | -3,317938 | 0,09367 | 0,16349815 |
| 204192_at | CD37 | NM_001774.1 | -3,306082 | 0,13734 | 0,16349815 |
| 207777_s_at | SP140 | NM_007237.1 | -3,3058881 | 0,13918 | 0,16349815 |
| 213566_at | RNASE6 | NM_005615.1 | -3,2290877 | 0,10537 | 0,16349815 |
| 213674_x_at | IGHD | AI858004 | -3,1397929 | 0,10861 | 0,16349815 |
| 212954_at | DYRK4 | AF263541.1 | -3,0967577 | 0,15107 | 0,16349815 |
| 214777_at | --- | BG482805 | -3,0954891 | 0,11394 | 0,16349815 |
| 214669_x_at | --- | BG485135 | -3,0813668 | 0,128 | 0,16349815 |
| 209138_x_at | --- | M87790.1 | -2,925698 | 0,17022 | 0,16349815 |
| 202626_s_at | LYN | NM_002350.1 | -2,8896131 | 0,14905 | 0,16349815 |
| 214615_at | P2RY10 | NM_014499.1 | -2,8498426 | 0,15433 | 0,16349815 |
| 202391_at | BASP1 | NM_006317.1 | -2,8128156 | 0,16876 | 0,16349815 |
| 210260_s_at | TNFAIP8 | BC005352.1 | -2,8004856 | 0,16996 | 0,16349815 |
| 221671_x_at | IGKC | M63438.1 | -2,7806271 | 0,17098 | 0,16349815 |
| 201301_s_at | ANXA4 | NM_001153.2 | -2,7799471 | 0,15827 | 0,16349815 |
| 221059_s_at | COTL1 | NM_021615.1 | -2,7777783 | 0,20968 | 0,16349815 |
| 210754_s_at | LYN | M79321.1 | -2,746282 | 0,18446 | 0,16349815 |
| 212377_s_at | NOTCH2 | AU158495 | -2,745543 | 0,1981 | 0,16349815 |
| 211138_s_at | KMO | BC005297.1 | -2,7423324 | 0,19345 | 0,16349815 |
| 204961_s_at | NCF1 | NM_000265.1 | -2,7250404 | 0,14094 | 0,16349815 |
| 219667_s_at | BANK1 | NM_017935.1 | -2,7113431 | 0,19171 | 0,16349815 |

FIG. 11 (Continued)

Table 3 (Continued)

| | | | | | |
|---|---|---|---|---|---|
| 203037_s_at | MTSS1 | NM_014751.1 | -2,6992825 | 0,21008 | 0,16349815 |
| 201079_at | SYNGR2 | NM_004710.1 | -2,6969455 | 0,20309 | 0,16349815 |
| 215967_s_at | LY9 | AL582804 | -2,6907423 | 0,13833 | 0,16349815 |
| 207616_s_at | TANK | NM_004180.1 | -2,6654073 | 0,21818 | 0,16349815 |
| 208771_s_at | LTA4H | J02959.1 | -2,6626082 | 0,24546 | 0,16349815 |
| 218100_s_at | ESRRBL1 | NM_018010.1 | -2,6595168 | 0,22597 | 0,16349815 |
| 222285_at | IGHD | AW134608 | -2,6588476 | 0,1584 | 0,16349815 |
| 200982_s_at | ANXA6 | NM_001155.2 | -2,6580372 | 0,14507 | 0,16349815 |
| 214084_x_at | NCF1 | AW072388 | -2,6533435 | 0,17866 | 0,16349815 |
| 221601_s_at | TOSO | NM_005449.1 | -2,6418038 | 0,19047 | 0,16349815 |
| 202443_x_at | NOTCH2 | NM_024408.1 | -2,6246233 | 0,24239 | 0,16349815 |
| 201494_at | PRCP | NM_005040.1 | -2,6216912 | 0,21878 | 0,16349815 |
| 204004_at | PAWR | NM_002583.1 | -2,6131395 | 0,16128 | 0,16349815 |
| 217762_s_at | RAB31 | AF183421.1 | -2,6023214 | 0,17369 | 0,16349815 |
| 219032_x_at | OPN3 | NM_014322.1 | -2,6018487 | 0,21027 | 0,16349815 |
| 202732_at | PKIG | NM_007066.1 | -2,5972088 | 0,17704 | 0,16349815 |
| 202864_s_at | SP100 | NM_017626.1 | -2,59353 | 0,22761 | 0,16349815 |
| 201780_s_at | RNF13 | NM_007282.1 | -2,5842805 | 0,22616 | 0,16349815 |
| 214768_x_at | --- | BG540628 | -2,5841903 | 0,17799 | 0,16349815 |
| 206726_at | PGDS | NM_014485.1 | -2,5812358 | 0,18141 | 0,16349815 |
| 219014_at | PLAC8 | NM_016619.1 | -2,5560972 | 0,23502 | 0,16349815 |
| 202080_s_at | OIP106 | NM_014965.1 | -2,5447824 | 0,21781 | 0,16349815 |
| 56256_at | SIDT2 | AA150165 | -2,5362795 | 0,26971 | 0,16349815 |
| 215621_s_at | IGHD | BG340670 | -2,5173083 | 0,16271 | 0,16349815 |
| 202478_at | TRIB2 | NM_021643.1 | -2,5156607 | 0,16963 | 0,16349815 |
| 208012_x_at | SP110 | NM_004509.1 | -2,512864 | 0,23595 | 0,16349815 |
| 221602_s_at | TOSO | NM_005449.1 | -2,5065789 | 0,17979 | 0,16349815 |
| 209762_x_at | SP110 | AF280094.1 | -2,5006403 | 0,24801 | 0,16349815 |
| 204661_at | CDW52 | NM_001803.1 | -2,4927321 | 0,22283 | 0,16349815 |
| 208296_x_at | TNFAIP8 | NM_014350.1 | -2,488662 | 0,18674 | 0,16349815 |
| 204960_at | PTPRCAP | NM_005608.1 | -2,4864487 | 0,25732 | 0,16349815 |
| 216853_x_at | --- | AF234255.1 | -2,4763598 | 0,22685 | 0,16349815 |
| 217480_x_at | --- | M20812 | -2,4415209 | 0,289 | 0,16349815 |
| 219375_at | CEPT1 | NM_006090.1 | -2,4393229 | 0,26203 | 0,16349815 |
| 201779_s_at | RNF13 | NM_007282.1 | -2,42964 | 0,2666 | 0,16349815 |
| 213888_s_at | T3JAM | AL022398 | -2,4151228 | 0,20028 | 0,16349815 |
| 214836_x_at | --- | BG536224 | -2,3888604 | 0,21891 | 0,16349815 |
| 204072_s_at | 13CDNA73 | NM_023037.1 | -2,3830142 | 0,20255 | 0,16349815 |
| 201462_at | SCRN1 | NM_014766.1 | -2,3810645 | 0,22571 | 0,16349815 |

FIG. 11 (Continued)

Table 3 (Continued)

| | | | | | |
|---|---|---|---|---|---|
| 207819_s_at | ABCB4 | NM_000443.2 | -2,3584146 | 0,19566 | 0,16349815 |
| 219054_at | FLJ14054 | NM_024563.1 | -2,3542854 | 0,262 | 0,16349815 |
| 209765_at | ADAM19 | AF311317.1 | -2,3522539 | 0,25969 | 0,16349815 |
| 221004_s_at | ITM2C | NM_030926.1 | -2,3496129 | 0,25651 | 0,16349815 |
| 209451_at | TANK | U59863.1 | -2,3443608 | 0,17613 | 0,16349815 |
| 204174_at | ALOX5AP | NM_001629.1 | -2,3406345 | 0,25479 | 0,16349815 |
| 209761_s_at | SP110 | AF280094.1 | -2,3350711 | 0,27456 | 0,16349815 |
| 204207_s_at | RNGTT | NM_003800.1 | -2,3223278 | 0,30649 | 0,16349815 |
| 205659_at | HDAC9 | NM_014707.1 | -2,3182874 | 0,25308 | 0,16349815 |
| 213702_x_at | ASAH1 | AI934569 | -2,3041594 | 0,3024 | 0,16349815 |
| 208438_s_at | FGR | NM_005248.1 | -2,2947732 | 0,24907 | 0,16349815 |
| 204057_at | --- | NM_002163.1 | -2,2925265 | 0,24952 | 0,16349815 |
| 200965_s_at | ABLIM1 | NM_006720.1 | -2,2877354 | 0,27327 | 0,16349815 |
| 201690_s_at | TPD52 | NM_005079.1 | -2,2863886 | 0,23328 | 0,16349815 |
| 217995_at | SQRDL | NM_021199.1 | -2,2670103 | 0,25799 | 0,16349815 |
| 212311_at | KIAA0746 | AA522514 | -2,2634404 | 0,26205 | 0,16349815 |
| 205882_x_at | ADD3 | AI818488 | -2,2563882 | 0,28313 | 0,16349815 |
| 205804_s_at | T3JAM | NM_025228.1 | -2,2510239 | 0,24583 | 0,16349815 |
| 201752_s_at | ADD3 | AI763123 | -2,2435235 | 0,27009 | 0,16349815 |
| 203791_at | DMXL1 | NM_005509.2 | -2,2406239 | 0,22286 | 0,16349815 |
| 203923_s_at | CYBB | NM_000397.2 | -2,2336068 | 0,23537 | 0,16349815 |
| 207700_s_at | NCOA3 | NM_006534.1 | -2,2282672 | 0,29974 | 0,16349815 |
| 34210_at | CDW52 | N90866 | -2,2231508 | 0,26397 | 0,16349815 |
| 201302_at | ANXA4 | NM_001153.2 | -2,21127 | 0,23787 | 0,16349815 |
| 216218_s_at | PLCL2 | AK023546.1 | -2,2030387 | 0,25073 | 0,16349815 |
| 218628_at | CGI-116 | NM_016053.1 | -2,2027508 | 0,24487 | 0,16349815 |
| 222150_s_at | LOC54103 | AK026747.1 | -2,2022667 | 0,26712 | 0,16349815 |
| 213309_at | PLCL2 | AL117515.1 | -2,1754973 | 0,30871 | 0,16349815 |
| 201689_s_at | TPD52 | BE974098 | -2,1696461 | 0,2365 | 0,16349815 |
| 202720_at | TES | NM_015641.1 | -2,1678434 | 0,32101 | 0,16349815 |
| 213106_at | ATP8A1 | AI769688 | -2,1620319 | 0,31012 | 0,16349815 |
| 217157_x_at | --- | AF103530.1 | -2,1559669 | 0,28377 | 0,16349815 |
| 212589_at | RRAS2 | AI753792 | -2,1523792 | 0,25268 | 0,16349815 |
| 218870_at | ARHGAP15 | NM_018460.1 | -2,1371511 | 0,3103 | 0,16349815 |
| 213603_s_at | RAC2 | BE138888 | -2,1220993 | 0,30202 | 0,16349815 |
| 201753_s_at | ADD3 | NM_019903.1 | -2,1173592 | 0,29813 | 0,16349815 |

(END TABLE 3)

FIG. 12

Table 4

| uniqid | Gene Symbol | name | ALL score | CB score | FC |
|---|---|---|---|---|---|
| 219686_at | STK32B | NM_018401.1 | 0,4242 | -1,5908 | 70,9882695 |
| 207030_s_at | CSRP2 | NM_001321.1 | 0,1447 | -0,5425 | 32,2457143 |
| 221349_at | VPREB1 | NM_007128.1 | 0,1045 | -0,392 | 29,6625629 |
| 208893_s_at | DUSP6 | NM_001946.1 | 0,0707 | -0,2651 | 27,1559162 |
| 203821_at | DTR | NM_001945.1 | 0,0865 | -0,3243 | 26,1738909 |
| 206548_at | FLJ23556 | NM_024880.1 | 0,0327 | -0,1228 | 22,5268438 |
| 214455_at | HIST1H2BC | NM_003526.1 | 0,1423 | -0,5335 | 13,7694382 |
| 204083_s_at | TPM2 | NM_003289.1 | 0,0058 | -0,0219 | 12,1776525 |
| 203325_s_at | COL5A1 | NM_000093.1 | 0,0313 | -0,1175 | 10,084284 |
| 211052_s_at | TBCD | BC006364.1 | 0,0022 | -0,0083 | 9,83609529 |
| 210448_s_at | P2RX5 | U49396.1 | -0,0435 | 0,163 | 0,07854471 |
| 216576_x_at | --- | AF103529.1 | -5,00E-04 | 0,0018 | 0,07809863 |
| 215176_x_at | --- | AW404894 | -0,0019 | 0,0073 | 0,06927678 |
| 218404_at | SNX10 | NM_013322.1 | -0,0296 | 0,1109 | 0,05674722 |
| 211644_x_at | IGKC | L14458.1 | -0,0484 | 0,1816 | 0,0556034 |
| 219452_at | DPEP2 | NM_022355.1 | -0,1045 | 0,3918 | 0,0542648 |
| 217977_at | SEPX1 | NM_016332.1 | -0,0031 | 0,0116 | 0,04559871 |
| 207384_at | PGLYRP1 | NM_005091.1 | -0,1649 | 0,6183 | 0,03653387 |
| 206851_at | RNASE3 | NM_002935.1 | -0,1312 | 0,4919 | 0,03622586 |
| 212531_at | LCN2 | NM_005564.1 | -0,0384 | 0,1441 | 0,02867131 |
| 207341_at | PRTN3 | NM_002777.2 | -0,015 | 0,0561 | 0,02684477 |
| 204351_at | S100P | NM_005980.1 | -0,0326 | 0,1224 | 0,02572385 |
| 205653_at | CTSG | NM_001911.1 | -0,0776 | 0,2911 | 0,0252826 |
| 214575_s_at | AZU1 | NM_001700.1 | -0,08 | 0,3 | 0,02249415 |
| 209395_at | CHI3L1 | NM_001276.1 | -0,0099 | 0,037 | 0,02200074 |
| 210254_at | MS4A3 | L35848.1 | -0,0564 | 0,2114 | 0,02102025 |
| 205557_at | BPI | NM_00172 | -0,174 | 0,6524 | 0,01380253 |
| 206676_at | CEACAM8 | NM_001816.1 | -0,1382 | 0,5181 | 0,01299119 |
| 202018_s_at | LTF | NM_002343.1 | -0,1455 | 0,5457 | 0,01101475 |
| 207269_at | DEFA4 | NM_001925.1 | -0,2072 | 0,7768 | 0,01044478 |
| 205033_s_at | DEFA3 /// DEFA1 | NM_004084.2 | -0,2722 | 1,0206 | 0,01009246 |
| 210244_at | CAMP | NM_004345.1 | -0,229 | 0,8589 | 0,00772014 |

FIG. 13

Table 5

| uniqid | Gene Symbol | Gene ID | Score(d) | Fold Change | q-value(%) |
|---|---|---|---|---|---|
| 213915_at | NKG7 | NM_005601.1 | 5,983131802 | 124,150007 | 0 |
| 212070_at | GPR56 | AL554008 | 5,739369152 | 96,31876425 | 0 |
| 219686_at | STK32B | NM_018401.1 | 5,454733947 | 88,29485679 | 0 |
| 204083_s_at | TPM2 | NM_003289.1 | 7,200517477 | 86,39400661 | 0 |
| 201656_at | ITGA6 | NM_000210.1 | 3,608963608 | 76,5955602 | 0,721504945 |
| 203821_at | HBEGF | NM_001945.1 | 6,384807438 | 67,51199789 | 0 |
| 208890_s_at | PLXNB2 | BC004542.1 | 4,723458081 | 42,4230754 | 0 |
| 211052_s_at | TBCD | BC006364.1 | 5,078070178 | 42,32600172 | 0 |
| 208893_s_at | DUSP6 | BC005047.1 | 3,668620364 | 40,75741958 | 0,574428937 |
| 222303_at | --- | AV700891 | 5,607926355 | 39,47834421 | 0 |
| 218051_s_at | NT5DC2 | NM_022908.1 | 5,931742375 | 37,88107509 | 0 |
| 215051_x_at | AIF1 | BF213829 | 3,986705796 | 36,62061856 | 0 |
| 208886_at | H1F0 | BC000145.1 | 3,236993093 | 34,54685137 | 1,216217619 |
| 213008_at | KIAA1794 | BG403615 | 6,844755801 | 34,24587987 | 0 |
| 220085_at | HELLS | NM_018063.1 | 6,306362713 | 33,69950883 | 0 |
| 212606_at | WDFY3 | AL536319 | 3,913291969 | 33,59538743 | 0,574428937 |
| 203373_at | SOCS2 | NM_003877.1 | 6,086071587 | 32,40530691 | 0 |
| 221349_at | VPREB1 | NM_007128.1 | 2,919595744 | 30,35636275 | 2,333617556 |
| 201105_at | LGALS1 | NM_002305.2 | 2,000548683 | 29,05019909 | 9,119266299 |
| 1405_i_at | CCL5 | M21121 | 3,572308786 | 28,7544829 | 0,721504945 |
| 204011_at | SPRY2 | NM_005842.1 | 4,151904859 | 27,57823469 | 0 |
| 220448_at | KCNK12 | NM_022055.1 | 2,165265603 | 24,49071557 | 7,422396375 |
| 207030_s_at | CSRP2 | NM_001321.1 | 4,170425856 | 23,41569907 | 0 |
| 211430_s_at | F7 /// IFI6 | M87789.1 | 2,801684221 | 22,53581408 | 2,718389616 |
| 202252_at | RAB13 | NM_002870.1 | 5,022411022 | 21,569539 | 0 |
| 212759_s_at | TCF7L2 | AI703074 | 4,232483654 | 20,71478135 | 0 |
| 201329_s_at | ETS2 | NM_005239.1 | 4,642379647 | 19,72629023 | 0 |
| 205290_s_at | BMP2 | NM_001200.1 | 2,432352904 | 18,92029269 | 5,173320847 |
| 212013_at | PXDN | D86983.1 | 4,651305773 | 18,79800022 | 0 |
| 219271_at | GALNT14 | NM_024572.1 | 3,202420565 | 18,07477934 | 1,216217619 |
| 207857_at | LILRA2 | NM_006866.1 | 5,078628645 | 17,85786323 | 0 |
| 218880_at | FOSL2 | N36408 | 3,019966043 | 16,80214403 | 1,954862874 |
| 218663_at | NCAPG | NM_022346.1 | 3,20921463 | 16,37236334 | 1,216217619 |
| 212192_at | KCTD12 | AI718937 | 3,148964887 | 15,94727296 | 1,598563708 |
| 204766_s_at | NUDT1 | NM_002452.1 | 2,258252744 | 15,70500226 | 6,612290746 |
| 218988_at | SLC35E3 | NM_018656.1 | 3,006706294 | 15,2126039 | 1,954862874 |
| 205289_at | BMP2 | AA583044 | 2,367688524 | 14,79522791 | 5,173320847 |
| 38487_at | STAB1 | D87433 | 1,948270193 | 14,7561568 | 10,2192819 |
| 202870_s_at | PBX2 | NM_004295.1 | 4,777666737 | 14,69099951 | 0 |
| 201890_at | RRM2 | BE966236 | 5,080539509 | 14,67701978 | 0 |
| 209035_at | MDK | M69148.1 | 2,178551175 | 14,66174425 | 7,422396375 |

FIG. 13 (Continued)

Table 5 (Continued)

| | | | | | |
|---|---|---|---|---|---|
| 206548_at | FLJ23556 | NM_024880.1 | 4,002681585 | 14,62013825 | 0 |
| 201830_s_at | NET1 | NM_005863.1 | 3,636988379 | 14,57815138 | 0,721504945 |
| 201163_s_at | IGFBP7 | NM_001553.1 | 2,570274335 | 14,45371539 | 4,006449217 |
| 218589_at | P2RY5 | NM_005767.1 | 3,658924745 | 13,77491391 | 0,574428937 |
| 213908_at | WHDC1L1 | AI824078 | 3,249840603 | 13,61408258 | 1,051771293 |
| 215028_at | SEMA6A | AB002438.1 | 1,987152031 | 13,53852796 | 9,119266299 |
| 210146_x_at | LILRB2 /// LILRA6 | AF004231.1 | 4,153943073 | 13,51456254 | 0 |
| 202668_at | EFNB2 | BF001670 | 2,259457058 | 13,4693878 | 6,612290746 |
| 202806_at | TCEB1 | NM_005488.1 | 2,271898452 | 13,43690355 | 6,612290746 |
| 219654_at | PTPLA | NM_014241.1 | 4,415114166 | 13,27933936 | 0 |
| 214761_at | ZNF423 | AW149417 | 4,35349946 | 12,79913318 | 0 |
| 207697_x_at | LILRB2 | NM_005874.1 | 5,306145354 | 12,48651815 | 0 |
| 210993_s_at | SMAD1 | U54826.1 | 2,237478475 | 12,46588042 | 6,612290746 |
| 221773_at | ELK3 | AW575374 | 3,761156067 | 12,44457389 | 0,574428937 |
| 219918_s_at | ASPM | NM_018123.1 | 3,061271108 | 12,33176437 | 1,75192403 |
| 201565_s_at | ID2 | NM_002166.1 | 3,184623624 | 11,87470956 | 1,216217619 |
| 218764_at | PRKCH | NM_024064.1 | 4,012156495 | 11,83596311 | 0 |
| 206631_at | PTGER2 | NM_000956.1 | 2,868054563 | 11,73038939 | 2,333617556 |
| 203092_at | TIMM44 | AF026030.1 | 3,598264443 | 11,18666861 | 0,721504945 |
| 210701_at | CFDP1 | D85939.1 | 5,108718952 | 10,58921091 | 0 |
| 200762_at | DPYSL2 | NM_001386.1 | 2,945034566 | 10,55281157 | 1,954862874 |
| 202933_s_at | YES1 | NM_005433.1 | 2,88225706 | 10,46933385 | 2,333617556 |
| 219493_at | SHCBP1 | NM_024745.1 | 4,015276247 | 10,24363503 | 0 |
| 214438_at | HLX1 | M60721.1 | 4,297231335 | 10,2208387 | 0 |
| 218694_at | ARMCX1 | NM_016608.1 | 3,479198234 | 10,20241666 | 0,721504945 |
| 206995_x_at | SCARF1 | NM_003693.1 | 3,511283307 | 10,18258091 | 0,721504945 |
| 201012_at | ANXA1 | NM_000700.1 | 3,26463788 | 10,11574527 | 1,051771293 |
| 209604_s_at | GATA3 | BC003070.1 | 2,297689881 | 10,04678305 | 5,899708453 |
| 204790_at | SMAD7 | NM_005904.1 | 3,382593636 | 10,03008031 | 0,875106583 |
| 203764_at | DLG7 | NM_014750.1 | 2,848868494 | 10,01062448 | 2,333617556 |
| 201324_at | EMP1 | NM_001423.1 | 2,091831079 | 9,899534965 | 8,1182283 |
| 201566_x_at | ID2 /// ID2B | D13891.1 | 3,350918063 | 9,781713339 | 0,875106583 |
| 202708_s_at | HIST2H2BE | NM_003528.1 | 3,253842238 | 9,767244894 | 1,051771293 |
| 211795_s_at | FYB | AF198052.1 | 1,944182043 | 9,760597911 | 10,2192819 |
| 37145_at | GNLY | M85276 | 2,134955658 | 9,638009193 | 7,422396375 |
| 204900_x_at | SAP30 | NM_003864.1 | 3,426061193 | 9,540411566 | 0,875106583 |
| 210613_s_at | SYNGR1 | BC000731.1 | 3,83409284 | 9,218022266 | 0,574428937 |
| 201218_at | CTBP2 /// LOC642909 | N23018 | 2,726252518 | 9,203683837 | 3,02553731 |
| 201416_at | SOX4 | BG528420 | 3,708730573 | 9,110733633 | 0,574428937 |
| 220918_at | C21orf96 | NM_025143.1 | 3,938806595 | 9,02561598 | 0,574428937 |

FIG. 13 (Continued)

Table 5 (Continued)

| 202481_at | DHRS3 | NM_004753.1 | 3,655855786 | 8,995747171 | 0,574428937 |
|---|---|---|---|---|---|
| 206233_at | B4GALT6 | AF097159.1 | 2,59584092 | 8,964632463 | 4,006449217 |
| 202095_s_at | BIRC5 | NM_001168.1 | 2,686597395 | 8,911889009 | 3,02553731 |
| 205349_at | GNA15 | NM_002068.1 | 3,858180547 | 8,819999674 | 0,574428937 |
| 213056_at | FRMD4B | AU145019 | 3,552363952 | 8,57684328 | 0,721504945 |
| 212812_at | SERINC5 | AI700633 | 2,980075336 | 8,461442105 | 1,954862874 |
| 204115_at | GNG11 | NM_004126.1 | 2,046315684 | 8,375602486 | 8,1182283 |
| 219555_s_at | CENPN | NM_018455.1 | 2,302986657 | 8,216888857 | 5,899708453 |
| 202555_s_at | MYLK | NM_005965.1 | 2,33253221 | 8,207890366 | 5,899708453 |
| 221523_s_at | RRAGD | AL138717 | 2,575342197 | 8,197200445 | 4,006449217 |
| 209210_s_at | PLEKHC1 | Z24725.1 | 1,925750957 | 8,184425219 | 10,2192819 |
| 201681_s_at | DLG5 | AB011155.1 | 2,639212698 | 8,089999366 | 3,550159167 |
| 221521_s_at | GINS2 | BC003186.1 | 2,314755451 | 8,034665274 | 5,899708453 |
| 203325_s_at | COL5A1 | AI130969 | 3,048891588 | 8,021418921 | 1,75192403 |
| 208808_s_at | HMGB2 | BC000903.1 | 4,97372363 | 7,847466779 | 0 |
| 54037_at | HPS4 | AL041451 | 3,253046683 | 7,788749486 | 1,051771293 |
| 222101_s_at | DCHS1 | BF222893 | 2,409558373 | 7,641019173 | 5,173320847 |
| 210387_at | HIST1H2BG | BC001131.1 | 2,087646121 | 7,594177253 | 8,1182283 |
| 204759_at | RCBTB2 | NM_001268.1 | 4,082095282 | 7,551287115 | 0 |
| 212124_at | ZMIZ1 | AF070622.1 | 4,759719341 | 7,528657666 | 0 |
| 219978_s_at | NUSAP1 | NM_018454.1 | 3,753419215 | 7,523428483 | 0,574428937 |
| 204529_s_at | TOX | AI961231 | 4,376095779 | 7,447642607 | 0 |
| 200985_s_at | CD59 | NM_000611.1 | 3,171590168 | 7,259381046 | 1,216217619 |
| 214623_at | SHFM3P1 | AA845710 | 3,30179762 | 7,249826626 | 1,051771293 |
| 206660_at | IGLL1 | NM_020070.1 | 2,409205741 | 7,096818107 | 5,173320847 |
| 202580_x_at | FOXM1 | NM_021953.1 | 2,41720965 | 7,087742051 | 5,173320847 |
| 212509_s_at | MXRA7 | BF968134 | 2,810997001 | 7,070053619 | 2,718389616 |
| 202039_at | TIAF1 /// MYO18A | NM_004740.1 | 3,566654253 | 7,068883848 | 0,721504945 |
| 202179_at | BLMH | NM_000386.1 | 4,170106728 | 7,029832648 | 0 |
| 204805_s_at | H1FX | NM_006026.1 | 3,225216211 | 6,945402717 | 1,216217619 |
| 209122_at | ADFP | BC005127.1 | 2,20026648 | 6,887767873 | 6,612290746 |
| 209892_at | FUT4 | AF305083.1 | 3,422068 | 6,884999929 | 0,875106583 |
| 203305_at | F13A1 | NM_000129.2 | 2,31102925 | 6,717435161 | 5,899708453 |
| 213792_s_at | --- | AA485908 | 2,621903856 | 6,659242854 | 3,550159167 |
| 201540_at | FHL1 | NM_001449.1 | 2,473027268 | 6,615965261 | 4,422944569 |
| 220952_s_at | PLEKHA5 | NM_019012.1 | 2,068592739 | 6,602981308 | 8,1182283 |
| 215111_s_at | TSC22D1 | AK027071.1 | 2,391751809 | 6,560720909 | 5,173320847 |
| 209576_at | GNAI1 | AL049933.1 | 3,461748661 | 6,508872462 | 0,721504945 |
| 209568_s_at | RGL1 | AF186779.1 | 2,907419053 | 6,489667644 | 2,333617556 |
| 201379_s_at | TPD52L2 | NM_003288.1 | 2,621685586 | 6,442005463 | 3,550159167 |
| 38671_at | PLXND1 | AB014520 | 3,760451024 | 6,432274002 | 0,574428937 |

FIG. 13 (Continued)

Table 5 (Continued)

| | | | | | |
|---|---|---|---|---|---|
| 217755_at | HN1 | NM_016185.1 | 2,731857049 | 6,426486006 | 3,02553731 |
| 202746_at | ITM2A | AL021786 | 2,156467923 | 6,38763448 | 7,422396375 |
| 213518_at | PRKCI | AI689429 | 3,477307331 | 6,357706906 | 0,721504945 |
| 211535_s_at | FGFR1 | M60485.1 | 2,483734822 | 6,262353706 | 4,422944569 |
| 222036_s_at | SLC12A4 | AI859865 | 4,741792307 | 6,230571831 | 0 |
| 209832_s_at | CDT1 | AF321125. | 3,868823166 | 6,201219617 | 0,574428937 |
| 203335_at | PHYH | NM_006214.1 | 2,369039882 | 6,187352285 | 5,173320847 |
| 212558_at | SPRY1 | BF508662 | 2,747430604 | 6,18381054 | 3,02553731 |
| 206940_s_at | POU4F1 | NM_006237.1 | 2,047887062 | 6,106751637 | 8,1182283 |
| 203675_at | NUCB2 | NM_005013.1 | 2,052092786 | 6,100500338 | 8,1182283 |
| 202503_s_at | KIAA0101 | NM_014736.1 | 4,107769405 | 5,983925286 | 0 |
| 204825_at | MELK | NM_014791.1 | 3,429861736 | 5,949448759 | 0,875106583 |
| 34726_at | CACNB3 | U07139 | 3,960057352 | 5,90400041 | 0,574428937 |
| 207011_s_at | PTK7 | NM_002821.1 | 3,418874099 | 5,88786939 | 0,875106583 |
| 209267_s_at | SLC39A8 | AB040120.1 | 2,646138891 | 5,887148682 | 3,550159167 |
| 201459_at | RUVBL2 | NM_006666.1 | 1,949475914 | 5,880000249 | 10,2192819 |
| 206020_at | SOCS6 | NM_016387.1 | 2,844536069 | 5,855999325 | 2,718389616 |
| 210835_s_at | CTBP2 | AF222711.1 | 2,815198504 | 5,809608712 | 2,718389616 |
| 219797_at | MGAT4A | NM_012214.1 | 2,504181751 | 5,715616734 | 4,422944569 |
| 214500_at | H2AFY | AF044286.1 | 2,418045419 | 5,619469497 | 5,173320847 |
| 201697_s_at | DNMT1 | NM_001379.1 | 4,196754044 | 5,576182816 | 0 |
| 203773_x_at | BLVRA | NM_000712.1 | 2,886381165 | 5,525060567 | 2,333617556 |
| 213827_at | SNX26 | AL137579.1 | 3,584509765 | 5,515311462 | 0,721504945 |
| 202672_s_at | ATF3 | M_001674.1 | 2,323316558 | 5,503896533 | 5,899708453 |
| 218280_x_at | HIST2H2AA3 /// HIST2H2AA4 | NM_003516.1 | 2,747073623 | 5,480582046 | 3,02553731 |
| 207735_at | RNF125 | NM_017831.1 | 2,76960702 | 5,41041302 | 2,718389616 |
| 202371_at | TCEAL4 | NM_024863.1 | 2,703610761 | 5,346815292 | 3,02553731 |
| 204822_at | TTK | NM_003318.1 | 3,224614137 | 5,342675008 | 1,216217619 |
| 222217_s_at | SLC27A3 | BC003654.1 | 2,940822482 | 5,330693062 | 1,954862874 |
| 207100_s_at | VAMP1 | NM_016830.1 | 2,709401114 | 5,276709735 | 3,02553731 |
| 218773_s_at | MSRB2 | NM_012228.1 | 2,459432384 | 5,268356043 | 4,422944569 |
| 202241_at | TRIB1 | NM_025195.1 | 2,140328173 | 5,237452889 | 7,422396375 |
| 221832_s_at | LUZP1 | AV741657 | 3,015017794 | 5,158660484 | 1,954862874 |
| 208636_at | ACTN1 | AI082078 | 2,107561549 | 5,130940841 | 8,1182283 |
| 208805_at | PSMA6 | BC002979.1 | 2,841548572 | 5,075487265 | 2,718389616 |
| 208680_at | PRDX1 | L19184.1 | 2,628487453 | 5,037622501 | 3,550159167 |
| 219218_at | BAHCC1 | NM_024696.1 | 2,070822638 | 5,026222911 | 8,1182283 |
| 221840_at | PTPRE | AA775177 | 2,733512649 | 4,994915226 | 3,02553731 |
| 214086_s_at | PARP2 | AK001980.1 | 2,696632561 | 4,959866078 | 3,02553731 |
| 214290_s_at | HIST2H2AA3 /// HIST2H2AA4 | AI313324 | 2,89224532 | 4,952286282 | 2,333617556 |

FIG. 13 (Continued)

Table 5 (Continued)

| | | | | | |
|---|---|---|---|---|---|
| 215836_s_at | PCDHGC3 /// PCDHGB4 | AK026188.1 | 2,204812905 | 4,939770173 | 6,612290746 |
| 214455_at | HIST1H2BG /// HIST1H2BC | NM_003526.1 | 2,668454949 | 4,935704356 | 3,550159167 |
| 218585_s_at | DTL | NM_016448.1 | 2,903493879 | 4,934099477 | 2,333617556 |
| 213539_at | CD3D | NM_000732.1 | 1,93494998 | 4,918500206 | 10,2192819 |
| 211126_s_at | CSRP2 | U46006.1 | 2,618183311 | 4,914902155 | 3,550159167 |
| 202910_s_at | CD97 | NM_001784.1 | 2,056780884 | 4,89902598 | 8,1182283 |
| 218883_s_at | MLF1IP | NM_024629.1 | 3,198821943 | 4,874551326 | 1,216217619 |
| 203362_s_at | MAD2L1 | NM_002358.2 | 2,717761973 | 4,874182246 | 3,02553731 |
| 201825_s_at | SCCPDH | AL572542 | 2,48719333 | 4,794146355 | 4,422944569 |
| 209365_s_at | ECM1 | U65932.1 | 1,928597706 | 4,763947611 | 10,2192819 |
| 201930_at | MCM6 | NM_005915.2 | 3,298598366 | 4,642985069 | 1,051771293 |
| 214617_at | PRF1 | AI445650 | 2,173035295 | 4,639661824 | 7,422396375 |
| 209464_at | AURKB | AB011446.1 | 3,067822685 | 4,634374671 | 1,75192403 |
| 59697_at | RAB15 | AA582932 | 3,685275879 | 4,632248394 | 0,574428937 |
| 209398_at | HIST1H1C | BC002649.1 | 2,241267866 | 4,577555171 | 6,612290746 |
| 215398_at | CDC73 | AF038194.1 | 2,891973089 | 4,568388186 | 2,333617556 |
| 202468_s_at | CTNNAL1 | NM_003798.1 | 2,467576672 | 4,506841789 | 4,422944569 |
| 221477_s_at | MGC5618 | BF575213 | 2,287404414 | 4,447434168 | 5,899708453 |
| 211474_s_at | SERPINB6 | BC004948.1 | 2,45378786 | 4,3650928 | 5,173320847 |
| 215213_at | NUP54 | AU146949 | 2,349559896 | 4,342778117 | 5,899708453 |
| 209357_at | CITED2 | AF109161.1 | 2,654501595 | 4,339657003 | 3,550159167 |
| 200696_s_at | GSN | NM_000177.1 | 2,529738803 | 4,321257736 | 4,422944569 |
| 203184_at | FBN2 | NM_001999.2 | 2,292780479 | 4,303803843 | 5,899708453 |
| 202615_at | GNAQ | BF222895 | 2,929621686 | 4,239329301 | 2,333617556 |
| 209129_at | TRIP6 | AF000974.1 | 1,906436048 | 4,191064073 | 10,2192819 |
| 202087_s_at | CTSL | NM_001912.1 | 2,038291939 | 4,190097043 | 9,119266299 |
| 203853_s_at | GAB2 | NM_012296.1 | 3,223973027 | 4,185872461 | 1,216217619 |
| 203633_at | CPT1A | BF001714 | 2,934977558 | 4,157015151 | 1,954862874 |
| 204026_s_at | ZWINT | NM_007057.1 | 2,988009913 | 4,125862182 | 1,954862874 |
| 202392_s_at | PISD | NM_014338.1 | 3,380354483 | 4,103801658 | 0,875106583 |
| 219938_s_at | PSTPIP2 | NM_024430.1 | 2,037594553 | 4,103039365 | 9,119266299 |
| 218627_at | DRAM | NM_018370.1 | 2,952344123 | 4,061502817 | 1,954862874 |
| 220855_at | CLTC | NM_014127.1 | 2,464406186 | 4,045945629 | 4,422944569 |
| 203355_s_at | PSD3 | NM_015310.1 | 2,023494082 | 4,036294033 | 9,119266299 |
| 202519_at | MLXIP | NM_014938.1 | 3,083220318 | 4,021770665 | 1,75192403 |
| 202107_s_at | MCM2 | NM_004526.1 | 2,82728704 | 4,014842939 | 2,718389616 |
| 203564_at | FANCG | NM_004629.1 | 3,435875483 | 3,96253796 | 0,875106583 |
| 201389_at | ITGA5 | NM_002205.1 | 2,675243258 | 3,949450634 | 3,550159167 |
| 219089_s_at | ZNF576 | NM_024327.1 | 3,173367322 | 3,930199268 | 1,216217619 |

FIG. 13 (Continued)

Table 5 (Continued)

| | | | | | |
|---|---|---|---|---|---|
| 209826_at | EGFL8 | AF020544.1 | 1,959956479 | 3,924922867 | 9,119266299 |
| 201666_at | TIMP1 | NM_003254.1 | 2,40050403 | 3,914048328 | 5,173320847 |
| 221434_s_at | C14orf156 | NM_031210.1 | 2,960861916 | 3,895932399 | 1,954862874 |
| 202212_at | PES1 | NM_014303.1 | 2,672076272 | 3,87503658 | 3,550159167 |
| 220137_at | FLJ20674 | NM_019086.1 | 2,415595915 | 3,873380628 | 5,173320847 |
| 205434_s_at | AAK1 /// LOC647217 | AW451954 | 2,63756639 | 3,866243756 | 3,550159167 |
| 204108_at | NFYA | AL031778 | 2,292853761 | 3,85792802 | 5,899708453 |
| 201090_x_at | K-ALPHA-1 | NM_006082.1 | 3,178182142 | 3,857671146 | 1,216217619 |
| 212136_at | ATP2B4 | AW517686 | 2,354673691 | 3,844190382 | 5,899708453 |
| 203744_at | HMGB3 | NM_005342.1 | 2,458720985 | 3,842861607 | 4,422944569 |
| 202705_at | CCNB2 | NM_004701.2 | 2,807004777 | 3,771006306 | 2,718389616 |
| 209711_at | SLC35D1 | N80922 | 2,129827579 | 3,746042629 | 7,422396375 |
| 221002_s_at | TSPAN14 | NM_030927.1 | 2,749907781 | 3,726714565 | 3,02553731 |
| 210046_s_at | IDH2 | U52144.1 | 2,849506997 | 3,717083718 | 2,333617556 |
| 213280_at | GARNL4 | AK000478.1 | 2,142065966 | 3,680741873 | 7,422396375 |
| 212990_at | SYNJ1 | AB020717.1 | 2,741610334 | 3,669090806 | 3,02553731 |
| 200853_at | H2AFZ | NM_002106.1 | 2,972556047 | 3,64259645 | 1,954862874 |
| 201970_s_at | NASP | NM_002482.1 | 2,494009218 | 3,630804808 | 4,422944569 |
| 207788_s_at | SORBS3 | NM_005775.1 | 2,169192485 | 3,629864727 | 7,422396375 |
| 213007_at | KIAA1794 | W74442 | 2,771340787 | 3,620800226 | 2,718389616 |
| 220728_at | --- | NM_025120.1 | 2,457266382 | 3,598645578 | 4,422944569 |
| 213228_at | PDE8B | AK023913.1 | 2,005784773 | 3,581576174 | 9,119266299 |
| 218966_at | MYO5C | NM_018728.1 | 2,175268389 | 3,55206998 | 7,422396375 |
| 203370_s_at | PDLIM7 | NM_005451.2 | 2,330860911 | 3,539393784 | 5,899708453 |
| 219863_at | HERC5 | NM_016323.1 | 2,889892057 | 3,538563005 | 2,333617556 |
| 202262_x_at | DDAH2 | NM_013974.1 | 2,575272525 | 3,508162113 | 4,006449217 |
| 209172_s_at | CENPF | U30872.1 | 2,149739469 | 3,477391498 | 7,422396375 |
| 204655_at | CCL5 | NM_002985.1 | 2,334111508 | 3,389183197 | 5,899708453 |
| 209276_s_at | GLRX | AF162769.1 | 3,00879487 | 3,385765558 | 1,954862874 |
| 216841_s_at | SOD2 | X15132.1 | 2,354559451 | 3,385523835 | 5,899708453 |
| 207746_at | POLQ | NM_014125.1 | 2,578588161 | 3,364067759 | 4,006449217 |
| 203097_s_at | RAPGEF2 | NM_014247.1 | 2,531746842 | 3,344109805 | 4,006449217 |
| 208740_at | SAP18 | BF593650 | 2,761663348 | 3,336289208 | 3,02553731 |
| 202345_s_at | FABP5 /// LOC728641 | NM_001444.1 | 2,622401142 | 3,325539986 | 3,550159167 |
| 222077_s_at | RACGAP1 | AU153848 | 2,236586414 | 3,299829014 | 6,612290746 |
| 203124_s_at | SLC11A2 | NM_000617.1 | 2,906328733 | 3,290779431 | 2,333617556 |
| 203148_s_at | TRIM14 | NM_014788.1 | 2,111898 | 3,278732094 | 8,1182283 |
| 219105_x_at | ORC6L | NM_014321.1 | 2,850606342 | 3,277613854 | 2,333617556 |
| 203149_at | PVRL2 | NM_002856.1 | 2,110681631 | 3,275825732 | 8,1182283 |
| 203688_at | PKD2 | NM_000297.1 | 2,201753703 | 3,273647998 | 6,612290746 |
| 2028_s_at | DBN1 | NM_004172.1 | 2,843707942 | 3,269363485 | 2,718389616 |

FIG. 13 (Continued)

Table 5 (Continued)

| | | | | | |
|---|---|---|---|---|---|
| 216026_s_at | POLE | AL080203.1 | 2,495874629 | 3,269278427 | 4,422944569 |
| 204887_s_at | PLK4 | NM_014264.1 | 2,028526278 | 3,257909981 | 9,119266299 |
| 221012_s_at | TRIM8 | NM_030912.1 | 2,506378607 | 3,246174015 | 4,422944569 |
| 206364_at | KIF14 | NM_014875.1 | 1,971999364 | 3,237609659 | 9,119266299 |
| 214501_s_at | TLR4 /// H2AFY | AF044286.1 | 2,784243923 | 3,234413748 | 2,718389616 |
| 203755_at | BUB1B | NM_001211.2 | 2,502957964 | 3,210501205 | 4,422944569 |
| 212239_at | PIK3R1 | AI680192 | 2,110156898 | 3,203161269 | 8,1182283 |
| 201063_at | RCN1 | NM_002901.1 | 3,023978072 | 3,194783078 | 1,75192403 |
| 211924_s_at | PLAUR | AY029180.1 | 1,904145543 | 3,187717952 | 10,2192819 |
| 37425_g_at | CCHCR1 | AB029343 | 2,652750656 | 3,176811543 | 3,550159167 |
| 200677_at | PTTG1IP | NM_004339.2 | 2,291083639 | 3,166618591 | 5,899708453 |
| 204173_at | MYL6B | NM_002475.1 | 2,654698952 | 3,163734381 | 3,550159167 |
| 218553_s_at | KCTD15 | NM_024076.1 | 1,922363831 | 3,14678352 | 10,2192819 |
| 202725_at | POLR2A | NM_000937.1 | 2,022248822 | 3,138288455 | 9,119266299 |
| 202378_s_at | LEPROT | NM_017526.1 | 2,161555163 | 3,123663794 | 7,422396375 |
| 202823_at | GCC2 | NM_005648.1 | 2,06206621 | 3,117938055 | 8,1182283 |
| 200616_s_at | KIAA0152 | BC000371.1 | 2,864085827 | 3,117386728 | 2,333617556 |
| 208923_at | CYFIP1 | BC005097.1 | 1,904946735 | 3,114763903 | 10,2192819 |
| 200980_s_at | PDHA1 | NM_000284.1 | 2,363000002 | 3,101084514 | 5,899708453 |
| 201121_s_at | PGRMC1 | NM_006667.2 | 2,880496497 | 3,084498311 | 2,333617556 |
| 201277_s_at | HNRPAB | NM_004499.1 | 2,246506861 | 3,067461948 | 6,612290746 |
| 218350_s_at | GMNN | NM_015895.1 | 2,197164168 | 3,06492592 | 6,612290746 |
| 200765_x_at | CTNNA1 | NM_001903.1 | 2,348866128 | 3,060687514 | 5,899708453 |
| 216565_x_at | LOC391020 | AL121994 | 1,967290077 | 3,041570713 | 9,119266299 |
| 203514_at | MAP3K3 | BF971923 | 2,109438899 | 3,029076135 | 8,1182283 |
| 210142_x_at | FLOT1 | AF117234.1 | 2,051595515 | 3,025050543 | 8,1182283 |
| 214728_x_at | SMARCA4 | AK026573.1 | 2,036094444 | 3,014378389 | 9,119266299 |
| 219253_at | FAM11B | NM_024121.1 | 2,28545127 | 3,006360449 | 5,899708453 |
| 204716_at | CCDC6 | NM_005436.1 | -2,36837259 | 0,333181653 | 4,006449217 |
| 207606_s_at | ARHGAP12 | NM_018287.1 | -2,21644727 | 0,333021144 | 5,173320847 |
| 211105_s_at | NFATC1 | U80918.1 | -2,05252541 | 0,332537314 | 7,422396375 |
| 217179_x_at | LOC96610 | X79782.1 | -2,38009064 | 0,332342387 | 4,006449217 |
| 202395_at | NSF | NM_006178.1 | -2,71945268 | 0,332296094 | 1,954862874 |
| 215284_at | SNX9 | AF070575.1 | -2,0907117 | 0,331839086 | 6,612290746 |
| 209762_x_at | SP110 | AF280094.1 | -2,83645015 | 0,331657687 | 1,598563708 |
| 208091_s_at | ECOP | NM_030796.1 | -2,80622844 | 0,330463158 | 1,598563708 |
| 220603_s_at | MCTP2 | NM_018349.1 | -2,43485179 | 0,328565709 | 3,550159167 |
| 206833_s_at | ACYP2 | NM_001108.1 | -2,01950637 | 0,326363617 | 7,422396375 |
| 212943_at | KIAA0528 | AB011100.2 | -2,0072437 | 0,325695715 | 8,1182283 |
| 206683_at | ZNF165 | NM_003447.1 | -1,88517056 | 0,325207135 | 10,2192819 |
| 203988_s_at | FUT8 | NM_004480.1 | -2,06077298 | 0,324050187 | 7,422396375 |

FIG. 13 (Continued)

Table 5 (Continued)

| | | | | | |
|---|---|---|---|---|---|
| 202255_s_at | SIPA1L1 | NM_015556.1 | -1,92291976 | 0,323730205 | 9,119266299 |
| 220132_s_at | CLEC2D | NM_013269.1 | -2,0191868 | 0,32321251 | 7,422396375 |
| 204638_at | ACP5 | NM_001611.2 | -2,1216822 | 0,321934934 | 6,612290746 |
| 203984_s_at | CASP9 | U60521.1 | -2,26426956 | 0,320243754 | 4,422944569 |
| 220368_s_at | SMEK1 | NM_017936.1 | -2,46595493 | 0,32001468 | 3,02553731 |
| 218197_s_at | OXR1 | NM_018002.1 | -1,88167679 | 0,319379226 | 10,2192819 |
| 200996_at | ACTR3 | NM_005721.2 | -2,65265876 | 0,319221995 | 2,333617556 |
| 205933_at | SETBP1 | NM_015559.1 | -1,97741058 | 0,319143379 | 8,1182283 |
| 203249_at | EZH1 | AB002386.1 | -2,03675942 | 0,314643512 | 7,422396375 |
| 203502_at | BPGM | NM_001724.1 | -2,3964601 | 0,314443534 | 3,550159167 |
| 211546_x_at | SNCA | L36674.1 | -2,43431008 | 0,312860017 | 3,550159167 |
| 217879_at | CDC27 | AL566824 | -2,93349929 | 0,312657199 | 1,051771293 |
| 201996_s_at | SPEN | AL524033 | -2,6443358 | 0,312655067 | 2,333617556 |
| 212985_at | --- | BF115739 | -2,04822762 | 0,312443657 | 7,422396375 |
| 218940_at | C14orf138 | NM_024558.1 | -2,56774942 | 0,312423899 | 2,718389616 |
| 213511_s_at | MTMR1 | AI167164 | -3,03583911 | 0,311333739 | 0,875106583 |
| 205316_at | SLC15A2 | BF223679 | -1,9180707 | 0,310949265 | 9,119266299 |
| 202719_s_at | TES | BC001451.1 | -1,97655382 | 0,310918178 | 8,1182283 |
| 215307_at | ZNF529 | AL109722.1 | -1,94777175 | 0,309946962 | 9,119266299 |
| 201151_s_at | MBNL1 | BF512200 | -2,32037498 | 0,307388525 | 4,006449217 |
| 214433_s_at | SELENBP1 | NM_003944.1 | -1,87773489 | 0,306022929 | 10,2192819 |
| 214712_at | SULT1A4 | AK023827.1 | -2,07102636 | 0,305547218 | 6,612290746 |
| 213878_at | LOC642732 /// LOC730793 | AI685944 | -2,35840672 | 0,302924703 | 4,006449217 |
| 207098_s_at | MFN1 | NM_017927.1 | -2,25783016 | 0,301400303 | 4,422944569 |
| 206296_x_at | MAP4K1 | NM_007181.1 | -2,04148993 | 0,299355065 | 7,422396375 |
| 218987_at | ATF7IP | NM_018179.1 | -3,3662149 | 0,299274683 | 0,426718639 |
| 203710_at | ITPR1 | NM_002222.1 | -2,53329133 | 0,295835608 | 2,718389616 |
| 202660_at | ITPR2 | AA834576 | -2,07113947 | 0,295326347 | 6,612290746 |
| 209750_at | NR1D2 | N32859 | -2,12522564 | 0,293567309 | 5,899708453 |
| 208753_s_at | NAP1L1 | BC002387.1 | -2,80038658 | 0,293448902 | 1,75192403 |
| 49485_at | PRDM4 | W22625 | -3,22466553 | 0,292578593 | 0,426718639 |
| 213186_at | DZIP3 | BG502305 | -2,016846 | 0,292177627 | 7,422396375 |
| 204156_at | KIAA0999 | AA044154 | -2,16277024 | 0,292052942 | 5,899708453 |
| 218819_at | INTS6 | NM_012141.1 | -2,50742083 | 0,291787843 | 3,02553731 |
| 200916_at | TAGLN2 | NM_003564.1 | -2,45897608 | 0,291538643 | 3,02553731 |
| 204882_at | ARHGAP25 | NM_014882.1 | -2,12344108 | 0,291277519 | 5,899708453 |
| 218319_at | PELI1 | NM_020651.2 | -2,08660031 | 0,289196008 | 6,612290746 |
| 221781_s_at | DNAJC10 | BG168666 | -2,56311855 | 0,289100058 | 2,718389616 |
| 210379_s_at | TLK1 | AF162666.1 | -2,11147917 | 0,287061198 | 6,612290746 |
| 212492_s_at | JMJD2B | AW237172 | -2,88605434 | 0,287025478 | 1,216217619 |

FIG. 13 (Continued)

Table 5 (Continued)

| 212098_at | LOC151162 | AL134724 | -3,26735074 | 0,286941307 | 0,426718639 |
|---|---|---|---|---|---|
| 201462_at | SCRN1 | NM_014766.1 | -2,13147908 | 0,286938547 | 5,899708453 |
| 215512_at | MARCH6 | AK000970.1 | -2,16544606 | 0,285156518 | 5,899708453 |
| 205804_s_at | TRAF3IP3 | NM_025228.1 | -2,15385949 | 0,284002869 | 5,899708453 |
| 200965_s_at | ABLIM1 | NM_006720.1 | -2,62169666 | 0,281916864 | 2,333617556 |
| 202391_at | BASP1 | NM_006317.1 | -2,23068749 | 0,281908046 | 5,173320847 |
| 204661_at | CD52 | NM_001803.1 | -2,32510411 | 0,281072903 | 4,006449217 |
| 205659_at | HDAC9 | NM_014707.1 | -2,62282323 | 0,277601868 | 2,333617556 |
| 209307_at | SWAP70 | AB014540.1 | -3,11149615 | 0,277277515 | 0,657936227 |
| 208178_x_at | TRIO | NM_007118.1 | -2,13353239 | 0,275450221 | 5,899708453 |
| 205081_at | CRIP1 /// GALK2 | NM_001311.1 | -1,90477262 | 0,275176686 | 9,119266299 |
| 56256_at | SIDT2 | AA150165 | -3,40332682 | 0,274066257 | 0,426718639 |
| 204057_at | IRF8 | AI073984 | -2,61068489 | 0,273766 | 2,718389616 |
| 221778_at | KIAA1718 | BE217882 | -3,38440536 | 0,273653091 | 0,426718639 |
| 37170_at | BMP2K | AB015331 | -2,05665348 | 0,272210151 | 7,422396375 |
| 215415_s_at | LYST | U70064.1 | -2,23706047 | 0,268008569 | 5,173320847 |
| 203394_s_at | HES1 | BE973687 | -2,10237847 | 0,266925957 | 6,612290746 |
| 207124_s_at | GNB5 | NM_006578.1 | -2,20944437 | 0,266642828 | 5,173320847 |
| 202864_s_at | CDC20 | AI695173 | -3,03564386 | 0,26606517 | 0,875106583 |
| 221704_s_at | VPS37B | BC005882.1 | -2,2418035 | 0,266036296 | 5,173320847 |
| 201779_s_at | RNF13 | AF070558.1 | -3,4733991 | 0,263067528 | 0,426718639 |
| 214149_s_at | ATP6V0E1 | AI252582 | -2,16127305 | 0,26252172 | 5,899708453 |
| 212838_at | DNMBP | AB023227.1 | -2,55011057 | 0,260309747 | 2,718389616 |
| 214437_s_at | SHMT2 | NM_005412.1 | -2,21213753 | 0,259675142 | 5,173320847 |
| 202863_at | SP100 | NM_003113.1 | -3,6222817 | 0,259032563 | 0 |
| 202996_at | POLD4 | NM_021173.1 | -2,36346443 | 0,258225191 | 4,006449217 |
| 203620_s_at | FCHSD2 | NM_014824.1 | -2,40468796 | 0,256784157 | 3,550159167 |
| 205882_x_at | ADD3 | AI818488 | -3,10776583 | 0,256761269 | 0,657936227 |
| 212715_s_at | MICAL3 /// LOC731210 | AB020626.1 | -2,04592261 | 0,256406558 | 7,422396375 |
| 205603_s_at | DIAPH2 | NM_007309.1 | -1,98650634 | 0,255530381 | 8,1182283 |
| 213238_at | ATP10D | AI478147 | -2,39625884 | 0,255180744 | 3,550159167 |
| 213309_at | PLCL2 | AL117515.1 | -3,11954701 | 0,254069156 | 0,657936227 |
| 219820_at | SLC6A16 | NM_014037.1 | -2,31277413 | 0,254029387 | 4,422944569 |
| 216899_s_at | SKAP2 | AC003999 | -2,22215295 | 0,251417882 | 5,173320847 |
| 210260_s_at | TNFAIP8 | BC005352.1 | -2,943215 | 0,250937498 | 1,051771293 |
| 219209_at | IFIH1 | NM_022168.1 | -2,18504128 | 0,24960738 | 5,173320847 |
| 205718_at | ITGB7 | NM_000889.1 | -2,24821953 | 0,249473719 | 5,173320847 |
| 208998_at | UCP2 | U94592.1 | -2,64140125 | 0,24910309 | 2,333617556 |
| 203819_s_at | IGF2BP3 | AU160004 | -2,19480551 | 0,248793723 | 5,173320847 |
| 211085_s_at | STK4 | Z25430.1 | -2,56706604 | 0,248049045 | 2,718389616 |

FIG. 13 (Continued)

Table 5 (Continued)

| | | | | | |
|---|---|---|---|---|---|
| 201301_s_at | ANXA4 | BC000182.1 | -2,25562466 | 0,247914701 | 4,422944569 |
| 202745_at | USP8 | NM_005154.1 | -3,81379736 | 0,246070662 | 0 |
| 203907_s_at | IQSEC1 | NM_014869.1 | -3,22655874 | 0,245247846 | 0,426718639 |
| 204207_s_at | RNGTT | AB012142.1 | -4,19029341 | 0,24425702 | 0 |
| 204633_s_at | RPS6KA5 | AF074393.1 | -2,14030807 | 0,244241454 | 5,899708453 |
| 209765_at | ADAM19 | Y13786.2 | -3,06243314 | 0,243869014 | 0,657936227 |
| 219202_at | RHBDF2 | NM_024599.1 | -3,01468219 | 0,240450548 | 0,875106583 |
| 205590_at | RASGRP1 | NM_005739.2 | -2,68132218 | 0,239674275 | 1,954862874 |
| 210279_at | GPR18 | AF261135.1 | -2,86942341 | 0,237490515 | 1,216217619 |
| 203749_s_at | RARA | AI806984 | -2,34969106 | 0,235131694 | 4,006449217 |
| 220933_s_at | ZCCHC6 | NM_024617.1 | -2,42544749 | 0,234144163 | 3,550159167 |
| 205306_x_at | KMO | AI074145 | -3,30019672 | 0,233159098 | 0,426718639 |
| 220386_s_at | EML4 | NM_019063.1 | -2,83936491 | 0,232916144 | 1,598563708 |
| 214787_at | DENND4A | BE268538 | -2,1581618 | 0,231084696 | 5,899708453 |
| 209060_x_at | NCOA3 | AI438999 | -3,48730329 | 0,228844492 | 0,426718639 |
| 209789_at | CORO2B | BF939649 | -2,58518058 | 0,228378185 | 2,718389616 |
| 205178_s_at | RBBP6 | NM_006910.1 | -3,5393337 | 0,227985596 | 0 |
| 209780_at | PHTF2 | AL136883.1 | -3,33631494 | 0,227228697 | 0,426718639 |
| 214084_x_at | ABR | AW072388 | -2,50881797 | 0,224133448 | 3,02553731 |
| 214791_at | LOC93349 | AK023116.1 | -3,37310881 | 0,223492405 | 0,426718639 |
| 202732_at | PKIG | NM_007066.1 | -2,44374786 | 0,222633448 | 3,550159167 |
| 212112_s_at | STX12 | AI816243 | -2,98749324 | 0,222338992 | 0,875106583 |
| 208195_at | TTN | NM_003319.1 | -2,32003737 | 0,222270147 | 4,006449217 |
| 217168_s_at | HERPUD1 | AF217990.1 | -2,93972343 | 0,21977806 | 1,051771293 |
| 203241_at | UVRAG | NM_003369.1 | -3,36893841 | 0,218287953 | 0,426718639 |
| 203642_s_at | COBLL1 | NM_014900.1 | -2,56613797 | 0,218196258 | 2,718389616 |
| 221602_s_at | FAIM3 | AF057557.1 | -2,42289533 | 0,217823272 | 3,550159167 |
| 222284_at | SIPA1L3 | AI734111 | -2,57457171 | 0,2158812 | 2,718389616 |
| 205027_s_at | MAP3K8 | NM_005204.1 | -2,91447369 | 0,215383673 | 1,051771293 |
| 213106_at | --- | AI769688 | -3,38995906 | 0,214358946 | 0,426718639 |
| 214861_at | JMJD2C | AI341811 | -2,65651544 | 0,212783468 | 2,333617556 |
| 206648_at | ZNF571 | NM_016536.1 | -2,5466764 | 0,212230645 | 2,718389616 |
| 208456_s_at | RRAS2 | NM_012250.1 | -2,33921734 | 0,210856309 | 4,006449217 |
| 218100_s_at | IFT57 | NM_018010.1 | -3,50651727 | 0,210267316 | 0,426718639 |
| 214190_x_at | GGA2 | AI799984 | -2,05422948 | 0,208196472 | 7,422396375 |
| 221059_s_at | COTL1 | NM_021615.1 | -3,69825131 | 0,205847248 | 0 |
| 201998_at | ST6GAL1 | AI743792 | -3,28577621 | 0,205815393 | 0,426718639 |
| 214722_at | NOTCH2NL | AW516297 | -3,19409323 | 0,20557105 | 0,426718639 |
| 213566_at | RNASE6 | NM_005615.1 | -2,48770008 | 0,204276339 | 3,02553731 |
| 219024_at | PLEKHA1 | NM_021622.1 | -2,34320863 | 0,204077164 | 4,006449217 |
| 209829_at | C6orf32 | AB002384.1 | -2,06144427 | 0,202542924 | 7,422396375 |
| 44790_s_at | C13orf18 | AI129310 | -2,38880541 | 0,197915938 | 3,550159167 |
| 215967_s_at | LY9 | AL582804 | -2,45382536 | 0,195274782 | 3,02553731 |

FIG. 13 (Continued)

Table 5 (Continued)

| | | | | | |
|---|---|---|---|---|---|
| 203414_at | MMD | NM_012329.1 | -3,20783716 | 0,193953732 | 0,426718639 |
| 203378_at | PCF11 | AB020631.1 | -4,1280387 | 0,193088137 | 0 |
| 212577_at | SMCHD1 | AA868754 | -3,88924451 | 0,191142371 | 0 |
| 209412_at | TMEM1 | U61500.1 | -2,76809196 | 0,190377493 | 1,75192403 |
| 200982_s_at | ANXA6 | NM_001155.2 | -2,56772745 | 0,188486008 | 2,718389616 |
| 209191_at | TUBB6 | BC002654.1 | -2,44073871 | 0,188337124 | 3,550159167 |
| 203791_at | DMXL1 | NM_005509.2 | -2,4506167 | 0,186353926 | 3,550159167 |
| 207057_at | SLC16A7 | NM_004731.1 | -2,6611648 | 0,185531517 | 2,333617556 |
| 201079_at | SYNGR2 | NM_004710.1 | -3,437189 | 0,184722933 | 0,426718639 |
| 204004_at | PAWR | AI336206 | -2,61404298 | 0,183908551 | 2,333617556 |
| 220768_s_at | CSNK1G3 | NM_004384.1 | -3,54911396 | 0,18366469 | 0 |
| 213142_x_at | LOC54103 | AV700415 | -3,26685646 | 0,182541806 | 0,426718639 |
| 219228_at | ZNF331 | NM_018555.2 | -3,19732943 | 0,181238089 | 0,426718639 |
| 209422_at | PHF20 | AL109965 | -4,19008712 | 0,180084568 | 0 |
| 201689_s_at | TPD52 | BE974098 | -2,42568313 | 0,178959814 | 3,550159167 |
| 219032_x_at | OPN3 | NM_014322.1 | -3,15173055 | 0,178085743 | 0,657936227 |
| 207616_s_at | TANK | NM_004180.1 | -3,68195062 | 0,175224012 | 0 |
| 207777_s_at | SP140 | NM_007237.1 | -3,68807151 | 0,173329275 | 0 |
| 214916_x_at | IFI6 /// SIX6 | BG340548 | -3,5679398 | 0,17232494 | 0 |
| 215716_s_at | ATP2B1 | L14561 | -3,57295223 | 0,172058795 | 0 |
| 212956_at | TBC1D9 | AI348094 | -2,20841767 | 0,17149759 | 5,173320847 |
| 204072_s_at | FRY | NM_023037.1 | -2,73874425 | 0,170741002 | 1,75192403 |
| 219667_s_at | BANK1 | NM_017935.1 | -3,29323002 | 0,166347181 | 0,426718639 |
| 212256_at | GALNT10 | BE906572 | -2,88310666 | 0,163758908 | 1,216217619 |
| 203640_at | MBNL2 | BE328496 | -3,30164672 | 0,162928548 | 0,426718639 |
| 203037_s_at | MTSS1 | NM_014751.1 | -3,37719899 | 0,162405996 | 0,426718639 |
| 204961_s_at | NCF1 | NM_000265.1 | -2,72829317 | 0,157032989 | 1,954862874 |
| 212314_at | KIAA0746 | AB018289.1 | -3,70040781 | 0,155759163 | 0 |
| 210042_s_at | CTSZ | AF073890.1 | -2,72994842 | 0,155704802 | 1,954862874 |
| 202478_at | TRIB2 | NM_021643.1 | -2,55324886 | 0,154641584 | 2,718389616 |
| 207819_s_at | ABCB4 | NM_000443.2 | -2,59311137 | 0,154213928 | 2,718389616 |
| 202080_s_at | TRAK1 | NM_014965.1 | -3,54540383 | 0,153656578 | 0 |
| 214615_at | P2RY10 | NM_014499.1 | -3,0878249 | 0,153244303 | 0,657936227 |
| 205632_s_at | PIP5K1B | NM_003558.1 | -2,70551749 | 0,144506768 | 1,954862874 |
| 202443_x_at | NOTCH2 | AA291203 | -4,4315558 | 0,136677283 | 0 |
| 205801_s_at | RASGRP3 | NM_015376.1 | -3,19826368 | 0,134405846 | 0,426718639 |
| 210889_s_at | FCGR2B | M31933.1 | -3,15584542 | 0,122452015 | 0,657936227 |
| 204192_at | CD37 | NM_001774.1 | -4,02288595 | 0,118122656 | 0 |
| 213515_x_at | HBG1 /// HBG2 | AI133353 | -3,07694996 | 0,110213181 | 0,657936227 |
| 211635_x_at | NTN2L | M24670.1 | -4,16255621 | 0,099988894 | 0 |
| 211639_x_at | C12orf32 | L23518.1 | -3,43465175 | 0,097118283 | 0,426718639 |

FIG. 13 (Continued)

Table 5 (Continued)

| | | | | | |
|---|---|---|---|---|---|
| 218404_at | SNX10 | NM_013322.1 | -3,62769696 | 0,095632598 | 0 |
| 205020_s_at | ARL4A | NM_005738.1 | -3,48942173 | 0,094615376 | 0,426718639 |
| 210538_s_at | BIRC3 | U37546.1 | -4,05459907 | 0,091399305 | 0 |
| 217388_s_at | KYNU | D55639.1 | -3,45161007 | 0,091151507 | 0,426718639 |
| 205901_at | PNOC | NM_006228.2 | -3,86029096 | 0,090660159 | 0 |

| | | | | | |
|---|---|---|---|---|---|
| 202625_at | LYN | AI356412 | -4,85663595 | 0,086097601 | 0 |
| 219574_at | MARCH1 | NM_017923.1 | -3,81756135 | 0,084416318 | 0 |
| 210448_s_at | P2RX5 | U49396.1 | -3,76762654 | 0,078204068 | 0 |
| 217258_x_at | IVD | AF043583.1 | -3,78213956 | 0,074935532 | 0 |
| 205544_s_at | CR2 | NM_001877.1 | -4,24402363 | 0,074832471 | 0 |
| 208536_s_at | BCL2L11 | NM_006538.1 | -4,31126035 | 0,074349278 | 0 |
| 219073_s_at | OSBPL10 | NM_017784.1 | -4,34099568 | 0,065720909 | 0 |
| 221239_s_at | FCRL2 | NM_030764.1 | -3,95137435 | 0,065241567 | 0 |
| 221586_s_at | E2F5 | U15642.1 | -4,11649247 | 0,064768569 | 0 |
| 205997_at | ADAM28 | NM_021778.1 | -3,82288736 | 0,064756098 | 0 |
| 211637_x_at | LOC652128 | L23516.1 | -3,9101367 | 0,0499538 | 0 |
| 206126_at | BLR1 | NM_001716.1 | -4,50201832 | 0,046081141 | 0 |
| 203865_s_at | ADARB1 | NM_015833.1 | -5,4256703 | 0,036227091 | 0 |

(END TABLE 5)

FIG. 14

Table 6

| uniqid | Gene Symbol | Gene ID | Score(d) | Fold Change | q-value(%) |
|---|---|---|---|---|---|
| 212070_at | GPR56 | AL554008 | 5,73936915 | 96,3187643 | 0 |
| 219686_at | STK32B | NM_018401.1 | 5,45473395 | 88,2948568 | 0 |
| 204083_s_at | TPM2 | NM_003289.1 | 7,20051748 | 86,3940066 | 0 |
| 201656_at | ITGA6 | NM_000210.1 | 3,60896361 | 76,5955602 | 0,72150495 |
| 203821_at | HBEGF | NM_001945.1 | 6,38480744 | 67,5119979 | 0 |
| 208890_s_at | PLXNB2 | BC004542.1 | 4,72345808 | 42,4230754 | 0 |
| 211052_s_at | TBCD | BC006364.1 | 5,07807018 | 42,3260017 | 0 |
| 208893_s_at | DUSP6 | BC005047.1 | 3,66862036 | 40,7574196 | 0,57442894 |
| 222303_at | --- | AV700891 | 5,60792636 | 39,4783442 | 0 |
| 218051_s_at | NT5DC2 | NM_022908.1 | 5,93174238 | 37,8810751 | 0 |
| 208886_at | H1F0 | BC000145.1 | 3,23699309 | 34,5468514 | 1,21621762 |
| 213008_at | KIAA1794 | BG403615 | 6,8447558 | 34,2458799 | 0 |
| 220085_at | HELLS | NM_018063.1 | 6,30636271 | 33,6995088 | 0 |
| 212606_at | WDFY3 | AL536319 | 3,91329197 | 33,5953874 | 0,57442894 |
| 203373_at | SOCS2 | NM_003877.1 | 6,08607159 | 32,4053069 | 0 |
| 221349_at | VPREB1 | NM_007128.1 | 2,91959574 | 30,3563628 | 2,33361756 |
| 1405_i_at | CCL5 | M21121 | 3,57230879 | 28,7544829 | 0,72150495 |
| 204011_at | SPRY2 | NM_005842.1 | 4,15190486 | 27,5782347 | 0 |
| 220448_at | KCNK12 | NM_022055.1 | 2,1652656 | 24,4907156 | 7,42239638 |
| 207030_s_at | CSRP2 | NM_001321.1 | 4,17042586 | 23,4156991 | 0 |
| 211430_s_at | F7 /// IFI6 | M87789.1 | 2,80168422 | 22,5358141 | 2,71838962 |
| 212759_s_at | TCF7L2 | AI703074 | 4,23248365 | 20,7147814 | 0 |
| 201329_s_at | ETS2 | NM_005239.1 | 4,64237965 | 19,7262902 | 0 |
| 205290_s_at | BMP2 | NM_001200.1 | 2,4323529 | 18,9202927 | 5,17332085 |
| 212013_at | PXDN | D86983.1 | 4,65130577 | 18,7980002 | 0 |
| 207857_at | LILRA2 | NM_006866.1 | 5,07862865 | 17,8578632 | 0 |
| 218880_at | FOSL2 | N36408 | 3,01996604 | 16,802144 | 1,95486287 |
| 218663_at | NCAPG | NM_022346.1 | 3,20921463 | 16,3723633 | 1,21621762 |
| 212192_at | KCTD12 | AI718937 | 3,14896489 | 15,947273 | 1,59856371 |
| 218988_at | SLC35E3 | NM_018656.1 | 3,00670629 | 15,2126039 | 1,95486287 |
| 205289_at | BMP2 | AA583044 | 2,36768852 | 14,7952279 | 5,17332085 |
| 38487_at | STAB1 | D87433 | 1,94827019 | 14,7561568 | 10,2192819 |
| 202870_s_at | PBX2 | NM_004295.1 | 4,77766674 | 14,6909995 | 0 |
| 201890_at | RRM2 | BE966236 | 5,08053951 | 14,6770198 | 0 |
| 209035_at | MDK | M69148.1 | 2,17855118 | 14,6617443 | 7,42239638 |
| 206548_at | FLJ23556 | NM_024880.1 | 4,00268159 | 14,6201383 | 0 |
| 201830_s_at | NET1 | NM_005863.1 | 3,63698838 | 14,5781514 | 0,72150495 |
| 218589_at | P2RY5 | NM_005767.1 | 3,65892475 | 13,7749139 | 0,57442894 |

FIG. 14 (Continued)

Table 6 (Continued)

| | | | | | |
|---|---|---|---|---|---|
| 215028_at | SEMA6A | AB002438.1 | 1,98715203 | 13,538528 | 9,1192663 |
| 210146_x_at | LILRB2 /// LILRA6 | AF004231.1 | 4,15394307 | 13,5145625 | 0 |
| 202668_at | EFNB2 | BF001670 | 2,25945706 | 13,4693878 | 6,61229075 |
| 214761_at | ZNF423 | AW149417 | 4,35349946 | 12,7991332 | 0 |
| 207697_x_at | LILRB2 | NM_005874.1 | 5,30614535 | 12,4865182 | 0 |
| 210993_s_at | SMAD1 | U54826.1 | 2,23747848 | 12,4658804 | 6,61229075 |
| 221773_at | ELK3 | AW575374 | 3,76115607 | 12,4445739 | 0,57442894 |
| 219918_s_at | ASPM | NM_018123.1 | 3,06127111 | 12,3317644 | 1,75192403 |
| 201565_s_at | ID2 | NM_002166.1 | 3,18462362 | 11,8747096 | 1,21621762 |
| 200762_at | DPYSL2 | NM_001386.1 | 2,94503457 | 10,5528116 | 1,95486287 |
| 202933_s_at | YES1 | NM_005433.1 | 2,88225706 | 10,4693339 | 2,33361756 |
| 219493_at | SHCBP1 | NM_024745.1 | 4,01527625 | 10,243635 | 0 |
| 201012_at | ANXA1 | NM_000700.1 | 3,26463788 | 10,1157453 | 1,05177129 |
| 204790_at | SMAD7 | NM_005904.1 | 3,38259364 | 10,0300803 | 0,87510658 |
| 201324_at | EMP1 | NM_001423.1 | 2,09183108 | 9,89953497 | 8,1182283 |
| 201566_x_at | ID2 /// ID2B | D13891.1 | 3,35091806 | 9,78171334 | 0,87510658 |
| 202708_s_at | HIST2H2BE | NM_003528.1 | 3,25384224 | 9,76724489 | 1,05177129 |
| 204900_x_at | SAP30 | NM_003864.1 | 3,42606119 | 9,54041157 | 0,87510658 |
| 201416_at | SOX4 | BG528420 | 3,70873057 | 9,11073363 | 0,57442894 |
| 220918_at | C21orf96 | NM_025143.1 | 3,9388066 | 9,02561598 | 0,57442894 |
| 202481_at | DHRS3 | NM_004753.1 | 3,65585579 | 8,99574717 | 0,57442894 |
| 202095_s_at | BIRC5 | NM_001168.1 | 2,6865974 | 8,91188901 | 3,02553731 |
| 213056_at | FRMD4B | AU145019 | 3,55236395 | 8,57684328 | 0,72150495 |
| 212812_at | SERINC5 | AI700633 | 2,98007534 | 8,46144211 | 1,95486287 |
| 202555_s_at | MYLK | NM_005965.1 | 2,33253221 | 8,20789037 | 5,89970845 |
| 209210_s_at | PLEKHC1 | Z24725.1 | 1,92575096 | 8,18442522 | 10,2192819 |
| 201681_s_at | DLG5 | AB011155.1 | 2,6392127 | 8,08999937 | 3,55015917 |
| 203325_s_at | COL5A1 | AI130969 | 3,04889159 | 8,02141892 | 1,75192403 |
| 54037_at | HPS4 | AL041451 | 3,25304668 | 7,78874949 | 1,05177129 |
| 222101_s_at | DCHS1 | BF222893 | 2,40955837 | 7,64101917 | 5,17332085 |
| 204759_at | RCBTB2 | NM_001268.1 | 4,08209528 | 7,55128712 | 0 |
| 212124_at | ZMIZ1 | AF070622.1 | 4,75971934 | 7,52865767 | 0 |
| 219978_s_at | NUSAP1 | NM_018454.1 | 3,75341922 | 7,52342848 | 0,57442894 |
| 214623_at | SHFM3P1 | AA845710 | 3,30179762 | 7,24982663 | 1,05177129 |
| 202580_x_at | FOXM1 | NM_021953.1 | 2,41720965 | 7,08774205 | 5,17332085 |
| 212509_s_at | MXRA7 | BF968134 | 2,810997 | 7,07005362 | 2,71838962 |
| 202039_at | TIAF1 /// MYO18A | NM_004740.1 | 3,56665425 | 7,06888385 | 0,72150495 |
| 204805_s_at | H1FX | NM_006026.1 | 3,22521621 | 6,94540272 | 1,21621762 |

FIG. 14 (Continued)

Table 6 (Continued)

| 209122_at | ADFP | BC005127.1 | 2,20026648 | 6,88776787 | 6,61229075 |
|---|---|---|---|---|---|
| 203305_at | F13A1 | NM_000129.2 | 2,31102925 | 6,71743516 | 5,89970845 |
| 213792_s_at | --- | AA485908 | 2,62190386 | 6,65924285 | 3,55015917 |
| 201540_at | FHL1 | NM_001449.1 | 2,47302727 | 6,61596526 | 4,42294457 |
| 209568_s_at | RGL1 | AF186779.1 | 2,90741905 | 6,48966764 | 2,33361756 |
| 201379_s_at | TPD52L2 | NM_003288.1 | 2,62168559 | 6,44200546 | 3,55015917 |
| 38671_at | PLXND1 | AB014520 | 3,76045102 | 6,432274 | 0,57442894 |
| 203335_at | PHYH | NM_006214.1 | 2,36903988 | 6,18735229 | 5,17332085 |
| 212558_at | SPRY1 | BF508662 | 2,7474306 | 6,18381054 | 3,02553731 |
| 206940_s_at | POU4F1 | NM_006237.1 | 2,04788706 | 6,10675164 | 8,1182283 |
| 204825_at | MELK | NM_014791.1 | 3,42986174 | 5,94944876 | 0,87510658 |
| 34726_at | CACNB3 | U07139 | 3,96005735 | 5,90400041 | 0,57442894 |
| 206020_at | SOCS6 | NM_016387.1 | 2,84453607 | 5,85599933 | 2,71838962 |
| 214500_at | H2AFY | AF044286.1 | 2,41804542 | 5,6194695 | 5,17332085 |
| 213827_at | SNX26 | AL137579.1 | 3,58450977 | 5,51531146 | 0,72150495 |
| 202672_s_at | ATF3 | M_001674.1 | 2,32331656 | 5,50389653 | 5,89970845 |
| 218280_x_at | HIST2H2A A3 /// HIST2H2A A4 | NM_003516.1 | 2,74707362 | 5,48058205 | 3,02553731 |
| 207735_at | RNF125 | NM_017831.1 | 2,76960702 | 5,41041302 | 2,71838962 |
| 204822_at | TTK | NM_003318.1 | 3,22461414 | 5,34267501 | 1,21621762 |
| 222217_s_at | SLC27A3 | BC003654.1 | 2,94082248 | 5,33069306 | 1,95486287 |
| 207100_s_at | VAMP1 | NM_016830.1 | 2,70940111 | 5,27670974 | 3,02553731 |
| 221832_s_at | LUZP1 | AV741657 | 3,01501779 | 5,15866048 | 1,95486287 |
| 219218_at | BAHCC1 | NM_024696.1 | 2,07082264 | 5,02622291 | 8,1182283 |
| 221840_at | PTPRE | AA775177 | 2,73351265 | 4,99491523 | 3,02553731 |
| 214290_s_at | HIST2H2A A3 /// HIST2H2A A4 | AI313324 | 2,89224532 | 4,95228628 | 2,33361756 |
| 215836_s_at | PCDHGC3 /// PCDHGB4 | AK026188.1 | 2,20481291 | 4,93977017 | 6,61229075 |
| 214455_at | HIST1H2B G /// HIST1H2B C | NM_003526.1 | 2,66845495 | 4,93570436 | 3,55015917 |
| 218585_s_at | DTL | NM_016448.1 | 2,90349388 | 4,93409948 | 2,33361756 |
| 213539_at | CD3D | NM_000732.1 | 1,93494998 | 4,91850021 | 10,2192819 |
| 211126_s_at | CSRP2 | U46006.1 | 2,61818331 | 4,91490216 | 3,55015917 |
| 202910_s_at | CD97 | NM_001784.1 | 2,05678088 | 4,89902598 | 8,1182283 |

FIG. 14 (Continued)

Table 6 (Continued)

| | | | | | |
|---|---|---|---|---|---|
| 218883_s_at | MLF1IP | NM_024629.1 | 3,19882194 | 4,87455133 | 1,21621762 |
| 209365_s_at | ECM1 | U65932.1 | 1,92859771 | 4,76394761 | 10,2192819 |
| 209398_at | HIST1H1C | BC002649.1 | 2,24126787 | 4,57755517 | 6,61229075 |
| 215398_at | CDC73 | AF038194.1 | 2,89197309 | 4,56838819 | 2,33361756 |
| 221477_s_at | MGC5618 | BF575213 | 2,28740441 | 4,44743417 | 5,89970845 |
| 202087_s_at | CTSL | NM_001912.1 | 2,03829194 | 4,19009704 | 9,1192663 |
| 203853_s_at | GAB2 | NM_012296.1 | 3,22397303 | 4,18587246 | 1,21621762 |
| 202392_s_at | PISD | NM_014338.1 | 3,38035448 | 4,10380166 | 0,87510658 |
| 203355_s_at | PSD3 | NM_015310.1 | 2,02349408 | 4,03629403 | 9,1192663 |
| 202519_at | MLXIP | NM_014938.1 | 3,08322032 | 4,02177067 | 1,75192403 |
| 201389_at | ITGA5 | NM_002205.1 | 2,67524326 | 3,94945063 | 3,55015917 |
| 220137_at | FLJ20674 | NM_019086.1 | 2,41559592 | 3,87338063 | 5,17332085 |
| 204108_at | NFYA | AL031778 | 2,29285376 | 3,85792802 | 5,89970845 |
| 209711_at | SLC35D1 | N80922 | 2,12982758 | 3,74604263 | 7,42239638 |
| 213280_at | GARNL4 | AK000478.1 | 2,14206597 | 3,68074187 | 7,42239638 |
| 207788_s_at | SORBS3 | NM_005775.1 | 2,16919249 | 3,62986473 | 7,42239638 |
| 220728_at | --- | NM_025120.1 | 2,45726638 | 3,59864558 | 4,42294457 |
| 219863_at | HERC5 | NM_016323.1 | 2,88989206 | 3,53856301 | 2,33361756 |

| | | | | | |
|---|---|---|---|---|---|
| 207746_at | POLQ | NM_014125.1 | 2,57858816 | 3,36406776 | 4,00644922 |
| 2028_s_at | DBN1 | NM_004172.1 | 2,84370794 | 3,26936349 | 2,71838962 |
| 204887_s_at | PLK4 | NM_014264.1 | 2,02852628 | 3,25790998 | 9,1192663 |
| 211924_s_at | PLAUR | AY029180.1 | 1,90414554 | 3,18771795 | 10,2192819 |
| 202725_at | POLR2A | NM_000937.1 | 2,02224882 | 3,13828846 | 9,1192663 |
| 211105_s_at | NFATC1 | U80918.1 | -2,0525254 | 0,33253731 | 7,42239638 |
| 217179_x_at | LOC96610 | X79782.1 | -2,3800906 | 0,33234239 | 4,00644922 |
| 209762_x_at | SP110 | AF280094.1 | -2,8364501 | 0,33165769 | 1,59856371 |
| 204638_at | ACP5 | NM_001611.2 | -2,1216822 | 0,32193493 | 6,61229075 |
| 203984_s_at | CASP9 | U60521.1 | -2,2642696 | 0,32024375 | 4,42294457 |
| 202719_s_at | TES | BC001451.1 | -1,9765538 | 0,31091818 | 8,1182283 |
| 210379_s_at | TLK1 | AF162666.1 | -2,1114792 | 0,2870612 | 6,61229075 |
| 212098_at | LOC151162 | AL134724 | -3,2673507 | 0,28694131 | 0,42671864 |
| 201462_at | SCRN1 | NM_014766.1 | -2,1314791 | 0,28693855 | 5,89970845 |
| 205804_s_at | TRAF3IP3 | NM_025228.1 | -2,1538595 | 0,28400287 | 5,89970845 |
| 200965_s_at | ABLIM1 | NM_006720.1 | -2,6216967 | 0,28191686 | 2,33361756 |
| 202391_at | BASP1 | NM_006317.1 | -2,2306875 | 0,28190805 | 5,17332085 |
| 204661_at | CD52 | NM_001803.1 | -2,3251041 | 0,2810729 | 4,00644922 |
| 205659_at | HDAC9 | NM_014707.1 | -2,6228232 | 0,27760187 | 2,33361756 |
| 209307_at | SWAP70 | AB014540.1 | -3,1114961 | 0,27727751 | 0,65793623 |
| 205081_at | CRIP1 /// GALK2 | NM_001311.1 | -1,9047726 | 0,27517669 | 9,1192663 |

FIG. 14 (Continued)

Table 6 (Continued)

| 56256_at | SIDT2 | AA150165 | -3,4033268 | 0,27406626 | 0,42671864 |
|---|---|---|---|---|---|
| 204057_at | IRF8 | AI073984 | -2,6106849 | 0,273766 | 2,71838962 |
| 203394_s_at | HES1 | BE973687 | -2,1023785 | 0,26692596 | 6,61229075 |
| 202864_s_at | CDC20 | AI695173 | -3,0356439 | 0,26606517 | 0,87510658 |
| 221704_s_at | VPS37B | BC005882.1 | -2,2418035 | 0,2660363 | 5,17332085 |
| 201779_s_at | RNF13 | AF070558.1 | -3,4733991 | 0,26306753 | 0,42671864 |
| 214437_s_at | SHMT2 | NM_005412.1 | -2,2121375 | 0,25967514 | 5,17332085 |
| 202863_at | SP100 | NM_003113.1 | -3,6222817 | 0,25903256 | 0 |
| 205882_x_at | ADD3 | AI818488 | -3,1077658 | 0,25676127 | 0,65793623 |
| 205603_s_at | DIAPH2 | NM_007309.1 | -1,9865063 | 0,25553038 | 8,1182283 |
| 213238_at | ATP10D | AI478147 | -2,3962588 | 0,25518074 | 3,55015917 |
| 213309_at | PLCL2 | AL117515.1 | -3,119547 | 0,25406916 | 0,65793623 |
| 216899_s_at | SKAP2 | AC003999 | -2,222153 | 0,25141788 | 5,17332085 |
| 210260_s_at | TNFAIP8 | BC005352.1 | -2,943215 | 0,2509375 | 1,05177129 |
| 208998_at | UCP2 | U94592.1 | -2,6414012 | 0,24910309 | 2,33361756 |
| 201301_s_at | ANXA4 | BC000182.1 | -2,2556247 | 0,2479147 | 4,42294457 |
| 204207_s_at | RNGTT | AB012142.1 | -4,1902934 | 0,24425702 | 0 |
| 209765_at | ADAM19 | Y13786.2 | -3,0624331 | 0,24386901 | 0,65793623 |
| 210279_at | GPR18 | AF261135.1 | -2,8694234 | 0,23749051 | 1,21621762 |
| 203749_s_at | RARA | AI806984 | -2,3496911 | 0,23513169 | 4,00644922 |
| 220933_s_at | ZCCHC6 | NM_024617.1 | -2,4254475 | 0,23414416 | 3,55015917 |
| 205306_x_at | KMO | AI074145 | -3,3001967 | 0,2331591 | 0,42671864 |
| 209789_at | CORO2B | BF939649 | -2,5851806 | 0,22837819 | 2,71838962 |
| 214084_x_at | ABR | AW072388 | -2,508818 | 0,22413345 | 3,02553731 |
| 202732_at | PKIG | NM_007066.1 | -2,4437479 | 0,22263345 | 3,55015917 |
| 208195_at | TTN | NM_003319.1 | -2,3200374 | 0,22227015 | 4,00644922 |
| 217168_s_at | HERPUD1 | AF217990.1 | -2,9397234 | 0,21977806 | 1,05177129 |
| 203642_s_at | COBLL1 | NM_014900.1 | -2,566138 | 0,21819626 | 2,71838962 |
| 221602_s_at | FAIM3 | AF057557.1 | -2,4228953 | 0,21782327 | 3,55015917 |
| 205027_s_at | MAP3K8 | NM_005204.1 | -2,9144737 | 0,21538367 | 1,05177129 |
| 213106_at | --- | AI769688 | -3,3899591 | 0,21435895 | 0,42671864 |
| 208456_s_at | RRAS2 | NM_012250.1 | -2,3392173 | 0,21085631 | 4,00644922 |
| 218100_s_at | IFT57 | NM_018010.1 | -3,5065173 | 0,21026732 | 0,42671864 |
| 221059_s_at | COTL1 | NM_021615.1 | -3,6982513 | 0,20584725 | 0 |
| 201998_at | ST6GAL1 | AI743792 | -3,2857762 | 0,20581539 | 0,42671864 |
| 213566_at | RNASE6 | NM_005615.1 | -2,4877001 | 0,20427634 | 3,02553731 |
| 209829_at | C6orf32 | AB002384.1 | -2,0614443 | 0,20254292 | 7,42239638 |
| 44790_s_at | C13orf18 | AI129310 | -2,3888054 | 0,19791594 | 3,55015917 |
| 215967_s_at | LY9 | AL582804 | -2,4538254 | 0,19527478 | 3,02553731 |
| 203414_at | MMD | NM_012329.1 | -3,2078372 | 0,19395373 | 0,42671864 |
| 203378_at | PCF11 | AB020631.1 | -4,1280387 | 0,19308814 | 0 |

FIG. 14 (Continued)

Table 6 (Continued)

| 209412_at | TMEM1 | U61500.1 | -2,768092 | 0,19037749 | 1,75192403 |
|---|---|---|---|---|---|
| 200982_s_at | ANXA6 | NM_001155.2 | -2,5677274 | 0,18848601 | 2,71838962 |
| 209191_at | TUBB6 | BC002654.1 | -2,4407387 | 0,18833712 | 3,55015917 |
| 203791_at | DMXL1 | NM_005509.2 | -2,4506167 | 0,18635393 | 3,55015917 |
| 201079_at | SYNGR2 | NM_004710.1 | -3,437189 | 0,18472293 | 0,42671864 |
| 204004_at | PAWR | AI336206 | -2,614043 | 0,18390855 | 2,33361756 |
| 213142_x_at | LOC54103 | AV700415 | -3,2668565 | 0,18254181 | 0,42671864 |
| 219228_at | ZNF331 | NM_018555.2 | -3,1973294 | 0,18123809 | 0,42671864 |
| 209422_at | PHF20 | AL109965 | -4,1900871 | 0,18008457 | 0 |
| 201689_s_at | TPD52 | BE974098 | -2,4256831 | 0,17895981 | 3,55015917 |
| 219032_x_at | OPN3 | NM_014322.1 | -3,1517305 | 0,17808574 | 0,65793623 |
| 207616_s_at | TANK | NM_004180.1 | -3,6819506 | 0,17522401 | 0 |
| 207777_s_at | SP140 | NM_007237.1 | -3,6880715 | 0,17332928 | 0 |
| 214916_x_at | IFI6 /// SIX6 | BG340548 | -3,5679398 | 0,17232494 | 0 |
| 212956_at | TBC1D9 | AI348094 | -2,2084177 | 0,17149759 | 5,17332085 |
| 204072_s_at | FRY | NM_023037.1 | -2,7387442 | 0,170741 | 1,75192403 |
| 219667_s_at | BANK1 | NM_017935.1 | -3,29323 | 0,16634718 | 0,42671864 |
| 212256_at | GALNT10 | BE906572 | -2,8831067 | 0,16375891 | 1,21621762 |
| 203640_at | MBNL2 | BE328496 | -3,3016467 | 0,16292855 | 0,42671864 |
| 203037_s_at | MTSS1 | NM_014751.1 | -3,377199 | 0,162406 | 0,42671864 |
| 204961_s_at | NCF1 /// NCF1B /// NCF1C | NM_000265.1 | -2,7282932 | 0,15703299 | 1,95486287 |
| 212314_at | KIAA0746 | AB018289.1 | -3,7004078 | 0,15575916 | 0 |
| 202478_at | TRIB2 | NM_021643.1 | -2,5532489 | 0,15464158 | 2,71838962 |
| 207819_s_at | ABCB4 | NM_000443.2 | -2,5931114 | 0,15421393 | 2,71838962 |
| 202080_s_at | TRAK1 | NM_014965.1 | -3,5454038 | 0,15365658 | 0 |
| 214615_at | P2RY10 | NM_014499.1 | -3,0878249 | 0,1532443 | 0,65793623 |
| 205632_s_at | PIP5K1B | NM_003558.1 | -2,7055175 | 0,14450677 | 1,95486287 |
| 202443_x_at | NOTCH2 | AA291203 | -4,4315558 | 0,13667728 | 0 |
| 210889_s_at | FCGR2B | M31933.1 | -3,1558454 | 0,12245201 | 0,65793623 |

| 204192_at | CD37 | NM_001774.1 | -4,022886 | 0,11812266 | 0 |
|---|---|---|---|---|---|
| 213515_x_at | HBG1 /// HBG2 | AI133353 | -3,07695 | 0,11021318 | 0,65793623 |
| 211635_x_at | NTN2L | M24670.1 | -4,1625562 | 0,09998889 | 0 |
| 218404_at | SNX10 | NM_013322.1 | -3,627697 | 0,0956326 | 0 |
| 210538_s_at | BIRC3 | U37546.1 | -4,0545991 | 0,09139931 | 0 |
| 217388_s_at | KYNU | D55639.1 | -3,4516101 | 0,09115151 | 0,42671864 |
| 202625_at | LYN | AI356412 | -4,856636 | 0,0860976 | 0 |
| 219574_at | MARCH1 | NM_017923.1 | -3,8175614 | 0,08441632 | 0 |
| 205544_s_at | CR2 | NM_001877.1 | -4,2440236 | 0,07483247 | 0 |

FIG. 14 (Continued)

Table 6 (Continued)

| | | | | | |
|---|---|---|---|---|---|
| 219073_s_at | OSBPL10 | NM_017784.1 | -4,3409957 | 0,06572091 | 0 |
| 221239_s_at | FCRL2 | NM_030764.1 | -3,9513744 | 0,06524157 | 0 |
| 221586_s_at | E2F5 | U15642.1 | -4,1164925 | 0,06476857 | 0 |
| 205997_at | ADAM28 | NM_021778.1 | -3,8228874 | 0,0647561 | 0 |
| 211637_x_at | LOC652128 | L23516.1 | -3,9101367 | 0,0499538 | 0 |
| 206126_at | BLR1 | NM_001716.1 | -4,5020183 | 0,04608114 | 0 |

(END TABLE 6)

FIG. 15

Table 7

| uniqid | Gene Symbol | Gene ID | Score(d) | Fold Change | q-value(%) |
|---|---|---|---|---|---|
| 213915_at | NKG7 | NM_005601.1 | 5,9831318 | 124,150007 | 0 |
| 215051_x_at | AIF1 | BF213829 | 3,9867058 | 36,6206186 | 0 |
| 201105_at | LGALS1 | NM_002305.2 | 2,00054868 | 29,0501991 | 9,1192663 |
| 202252_at | RAB13 | NM_002870.1 | 5,02241102 | 21,569539 | 0 |
| 219271_at | GALNT14 | NM_024572.1 | 3,20242057 | 18,0747793 | 1,21621762 |
| 204766_s_at | NUDT1 | NM_002452.1 | 2,25825274 | 15,7050023 | 6,61229075 |
| 201163_s_at | IGFBP7 | NM_001553.1 | 2,57027434 | 14,4537154 | 4,00644922 |
| 213908_at | WHDC1L1 | AI824078 | 3,2498406 | 13,6140826 | 1,05177129 |
| 202806_at | TCEB1 | NM_005488.1 | 2,27189845 | 13,4369036 | 6,61229075 |
| 219654_at | PTPLA | NM_014241.1 | 4,41511417 | 13,2793394 | 0 |
| 218764_at | PRKCH | NM_024064.1 | 4,0121565 | 11,8359631 | 0 |
| 206631_at | PTGER2 | NM_000956.1 | 2,86805456 | 11,7303894 | 2,33361756 |
| 203092_at | TIMM44 | AF026030.1 | 3,59826444 | 11,1866686 | 0,72150495 |
| 210701_at | CFDP1 | D85939.1 | 5,10871895 | 10,5892109 | 0 |
| 214438_at | HLX1 | M60721.1 | 4,29723134 | 10,2208387 | 0 |
| 218694_at | ARMCX1 | NM_016608.1 | 3,47919823 | 10,2024167 | 0,72150495 |
| 206995_x_at | SCARF1 | NM_003693.1 | 3,51128331 | 10,1825809 | 0,72150495 |
| 209604_s_at | GATA3 | BC003070.1 | 2,29768988 | 10,0467831 | 5,89970845 |
| 203764_at | DLG7 | NM_014750.1 | 2,84886849 | 10,0106245 | 2,33361756 |
| 211795_s_at | FYB | AF198052.1 | 1,94418204 | 9,76059791 | 10,2192819 |
| 37145_at | GNLY | M85276 | 2,13495566 | 9,63800919 | 7,42239638 |
| 210613_s_at | SYNGR1 | BC000731.1 | 3,83409284 | 9,21802227 | 0,57442894 |
| 201218_at | CTBP2 /// LOC642909 | N23018 | 2,72625252 | 9,20368384 | 3,02553731 |
| 206233_at | B4GALT6 | AF097159.1 | 2,59584092 | 8,96463246 | 4,00644922 |
| 205349_at | GNA15 | NM_002068.1 | 3,85818055 | 8,81999967 | 0,57442894 |
| 204115_at | GNG11 | NM_004126.1 | 2,04631568 | 8,37560249 | 8,1182283 |
| 219555_s_at | CENPN | NM_018455.1 | 2,30298666 | 8,21688886 | 5,89970845 |
| 221523_s_at | RRAGD | AL138717 | 2,5753422 | 8,19720045 | 4,00644922 |
| 221521_s_at | GINS2 | BC003186.1 | 2,31475545 | 8,03466527 | 5,89970845 |
| 208808_s_at | HMGB2 | BC000903.1 | 4,97372363 | 7,84746678 | 0 |
| 210387_at | HIST1H2BG | BC001131.1 | 2,08764612 | 7,59417725 | 8,1182283 |
| 204529_s_at | TOX | AI961231 | 4,37609578 | 7,44764261 | 0 |
| 200985_s_at | CD59 | NM_000611.1 | 3,17159017 | 7,25938105 | 1,21621762 |
| 206660_at | IGLL1 | NM_020070.1 | 2,40920574 | 7,09681811 | 5,17332085 |
| 202179_at | BLMH | NM_000386.1 | 4,17010673 | 7,02983265 | 0 |
| 209892_at | FUT4 | AF305083.1 | 3,422068 | 6,88499993 | 0,87510658 |
| 220952_s_at | PLEKHA5 | NM_019012.1 | 2,06859274 | 6,60298131 | 8,1182283 |
| 215111_s_at | TSC22D1 | AK027071.1 | 2,39175181 | 6,56072091 | 5,17332085 |

FIG. 15 (Continued)

Table 7 (Continued)

| | | | | | |
|---|---|---|---|---|---|
| 209576_at | GNAI1 | AL049933.1 | 3,46174866 | 6,50887246 | 0,72150495 |
| 217755_at | HN1 | NM_016185.1 | 2,73185705 | 6,42648601 | 3,02553731 |
| 202746_at | ITM2A | AL021786 | 2,15646792 | 6,38763448 | 7,42239638 |
| 213518_at | PRKCI | AI689429 | 3,47730733 | 6,35770691 | 0,72150495 |
| 211535_s_at | FGFR1 | M60485.1 | 2,48373482 | 6,26235371 | 4,42294457 |
| 222036_s_at | SLC12A4 | AI859865 | 4,74179231 | 6,23057183 | 0 |
| 209832_s_at | CDT1 | AF321125. | 3,86882317 | 6,20121962 | 0,57442894 |
| 203675_at | NUCB2 | NM_005013.1 | 2,05209279 | 6,10050034 | 8,1182283 |
| 202503_s_at | KIAA0101 | NM_014736.1 | 4,10776941 | 5,98392529 | 0 |
| 207011_s_at | PTK7 | NM_002821.1 | 3,4188741 | 5,88786939 | 0,87510658 |
| 209267_s_at | SLC39A8 | AB040120.1 | 2,64613889 | 5,88714868 | 3,55015917 |
| 201459_at | RUVBL2 | NM_006666.1 | 1,94947591 | 5,88000025 | 10,2192819 |
| 210835_s_at | CTBP2 | AF222711.1 | 2,8151985 | 5,80960871 | 2,71838962 |
| 219797_at | MGAT4A | NM_012214.1 | 2,50418175 | 5,71561673 | 4,42294457 |
| 201697_s_at | DNMT1 | NM_001379.1 | 4,19675404 | 5,57618282 | 0 |
| 203773_x_at | BLVRA | NM_000712.1 | 2,88638117 | 5,52506057 | 2,33361756 |
| 202371_at | TCEAL4 | NM_024863.1 | 2,70361076 | 5,34681529 | 3,02553731 |
| 218773_s_at | MSRB2 | NM_012228.1 | 2,45943238 | 5,26835604 | 4,42294457 |
| 202241_at | TRIB1 | NM_025195.1 | 2,14032817 | 5,23745289 | 7,42239638 |
| 208636_at | ACTN1 | AI082078 | 2,10756155 | 5,13094084 | 8,1182283 |
| 208805_at | PSMA6 | BC002979.1 | 2,84154857 | 5,07548727 | 2,71838962 |
| 208680_at | PRDX1 | L19184.1 | 2,62848745 | 5,0376225 | 3,55015917 |
| 214086_s_at | PARP2 | AK001980.1 | 2,69663256 | 4,95986608 | 3,02553731 |
| 203362_s_at | MAD2L1 | NM_002358.2 | 2,71776197 | 4,87418225 | 3,02553731 |
| 201825_s_at | SCCPDH | AL572542 | 2,48719333 | 4,79414636 | 4,42294457 |
| 201930_at | MCM6 | NM_005915.2 | 3,29859837 | 4,64298507 | 1,05177129 |
| 214617_at | PRF1 | AI445650 | 2,1730353 | 4,63966182 | 7,42239638 |
| 209464_at | AURKB | AB011446.1 | 3,06782269 | 4,63437467 | 1,75192403 |
| 59697_at | RAB15 | AA582932 | 3,68527588 | 4,63224839 | 0,57442894 |
| 202468_s_at | CTNNAL1 | NM_003798.1 | 2,46757667 | 4,50684179 | 4,42294457 |
| 211474_s_at | SERPINB6 | BC004948.1 | 2,45378786 | 4,3650928 | 5,17332085 |
| 215213_at | NUP54 | AU146949 | 2,3495599 | 4,34277812 | 5,89970845 |
| 209357_at | CITED2 | AF109161.1 | 2,6545016 | 4,339657 | 3,55015917 |
| 200696_s_at | GSN | NM_000177.1 | 2,5297388 | 4,32125774 | 4,42294457 |
| 203184_at | FBN2 | NM_001999.2 | 2,29278048 | 4,30380384 | 5,89970845 |
| 202615_at | GNAQ | BF222895 | 2,92962169 | 4,2393293 | 2,33361756 |
| 209129_at | TRIP6 | AF000974.1 | 1,90643605 | 4,19106407 | 10,2192819 |
| 203633_at | CPT1A | BF001714 | 2,93497756 | 4,15701515 | 1,95486287 |
| 204026_s_at | ZWINT | NM_007057.1 | 2,98800991 | 4,12586218 | 1,95486287 |
| 219938_s_at | PSTPIP2 | NM_024430.1 | 2,03759455 | 4,10303937 | 9,1192663 |
| 218627_at | DRAM | NM_018370.1 | 2,95234412 | 4,06150282 | 1,95486287 |

FIG. 15 (Continued)

Table 7 (Continued)

| | | | | | |
|---|---|---|---|---|---|
| 220855_at | CLTC | NM_014127.1 | 2,46440619 | 4,04594563 | 4,42294457 |
| 202107_s_at | MCM2 | NM_004526.1 | 2,82728704 | 4,01484294 | 2,71838962 |
| 203564_at | FANCG | NM_004629.1 | 3,43587548 | 3,96253796 | 0,87510658 |
| 219089_s_at | ZNF576 | NM_024327.1 | 3,17336732 | 3,93019927 | 1,21621762 |
| 209826_at | EGFL8 | AF020544.1 | 1,95995648 | 3,92492287 | 9,1192663 |
| 201666_at | TIMP1 | NM_003254.1 | 2,40050403 | 3,91404833 | 5,17332085 |
| 221434_s_at | C14orf156 | NM_031210.1 | 2,96086192 | 3,8959324 | 1,95486287 |
| 202212_at | PES1 | NM_014303.1 | 2,67207627 | 3,87503658 | 3,55015917 |
| 205434_s_at | AAK1 /// LOC647217 | AW451954 | 2,63756639 | 3,86624376 | 3,55015917 |
| 201090_x_at | K-ALPHA-1 | NM_006082.1 | 3,17818214 | 3,85767115 | 1,21621762 |
| 212136_at | ATP2B4 | AW517686 | 2,35467369 | 3,84419038 | 5,89970845 |
| 203744_at | HMGB3 | NM_005342.1 | 2,45872099 | 3,84286161 | 4,42294457 |
| 202705_at | CCNB2 | NM_004701.2 | 2,80700478 | 3,77100631 | 2,71838962 |
| 221002_s_at | TSPAN14 | NM_030927.1 | 2,74990778 | 3,72671457 | 3,02553731 |
| 210046_s_at | IDH2 | U52144.1 | 2,849507 | 3,71708372 | 2,33361756 |
| 212990_at | SYNJ1 | AB020717.1 | 2,74161033 | 3,66909081 | 3,02553731 |
| 200853_at | H2AFZ | NM_002106.1 | 2,97255605 | 3,64259645 | 1,95486287 |
| 201970_s_at | NASP | NM_002482.1 | 2,49400922 | 3,63080481 | 4,42294457 |
| 213007_at | KIAA1794 | W74442 | 2,77134079 | 3,62080023 | 2,71838962 |
| 213228_at | PDE8B | AK023913.1 | 2,00578477 | 3,58157617 | 9,1192663 |
| 218966_at | MYO5C | NM_018728.1 | 2,17526839 | 3,55206998 | 7,42239638 |
| 203370_s_at | PDLIM7 | NM_005451.2 | 2,33086091 | 3,53939378 | 5,89970845 |
| 202262_x_at | DDAH2 | NM_013974.1 | 2,57527253 | 3,50816211 | 4,00644922 |
| 209172_s_at | CENPF | U30872.1 | 2,14973947 | 3,4773915 | 7,42239638 |
| 204655_at | CCL5 | NM_002985.1 | 2,33411151 | 3,3891832 | 5,89970845 |
| 209276_s_at | GLRX | AF162769.1 | 3,00879487 | 3,38576556 | 1,95486287 |
| 216841_s_at | SOD2 | X15132.1 | 2,35455945 | 3,38552384 | 5,89970845 |
| 203097_s_at | RAPGEF2 | NM_014247.1 | 2,53174684 | 3,34410981 | 4,00644922 |
| 208740_at | SAP18 | BF593650 | 2,76166335 | 3,33628921 | 3,02553731 |
| 202345_s_at | FABP5 /// LOC728641 | NM_001444.1 | 2,62240114 | 3,32553999 | 3,55015917 |
| 222077_s_at | RACGAP1 | AU153848 | 2,23658641 | 3,29982901 | 6,61229075 |
| 203124_s_at | SLC11A2 | NM_000617.1 | 2,90632873 | 3,29077943 | 2,33361756 |
| 203148_s_at | TRIM14 | NM_014788.1 | 2,111898 | 3,27873209 | 8,1182283 |
| 219105_x_at | ORC6L | NM_014321.1 | 2,85060634 | 3,27761385 | 2,33361756 |
| 203149_at | PVRL2 | NM_002856.1 | 2,11068163 | 3,27582573 | 8,1182283 |
| 203688_at | PKD2 | NM_000297.1 | 2,2017537 | 3,273648 | 6,61229075 |
| 216026_s_at | POLE | AL080203.1 | 2,49587463 | 3,26927843 | 4,42294457 |
| 221012_s_at | TRIM8 | NM_030912.1 | 2,50637861 | 3,24617402 | 4,42294457 |
| 206364_at | KIF14 | NM_014875.1 | 1,97199936 | 3,23760966 | 9,1192663 |

FIG. 15 (Continued)

Table 7 (Continued)

| 214501_s_at | TLR4 /// H2AFY | AF044286.1 | 2,78424392 | 3,23441375 | 2,71838962 |
|---|---|---|---|---|---|
| 203755_at | BUB1B | NM_001211.2 | 2,50295796 | 3,21050121 | 4,42294457 |
| 212239_at | PIK3R1 | AI680192 | 2,1101569 | 3,20316127 | 8,1182283 |
| 201063_at | RCN1 | NM_002901.1 | 3,02397807 | 3,19478308 | 1,75192403 |
| 37425_g_at | CCHCR1 | AB029343 | 2,65275066 | 3,17681154 | 3,55015917 |
| 200677_at | PTTG1IP | NM_004339.2 | 2,29108364 | 3,16661859 | 5,89970845 |
| 204173_at | MYL6B | NM_002475.1 | 2,65469895 | 3,16373438 | 3,55015917 |
| 218553_s_at | KCTD15 | NM_024076.1 | 1,92236383 | 3,14678352 | 10,2192819 |
| 202378_s_at | LEPROT | NM_017526.1 | 2,16155516 | 3,12366379 | 7,42239638 |
| 202823_at | GCC2 | NM_005648.1 | 2,06206621 | 3,11793806 | 8,1182283 |
| 200616_s_at | KIAA0152 | BC000371.1 | 2,86408583 | 3,11738673 | 2,33361756 |
| 208923_at | CYFIP1 | BC005097.1 | 1,90494674 | 3,1147639 | 10,2192819 |
| 200980_s_at | PDHA1 | NM_000284.1 | 2,363 | 3,10108451 | 5,89970845 |
| 201121_s_at | PGRMC1 | NM_006667.2 | 2,8804965 | 3,08449831 | 2,33361756 |
| 201277_s_at | HNRPAB | NM_004499.1 | 2,24650686 | 3,06746195 | 6,61229075 |
| 218350_s_at | GMNN | NM_015895.1 | 2,19716417 | 3,06492592 | 6,61229075 |
| 200765_x_at | CTNNA1 | NM_001903.1 | 2,34886613 | 3,06068751 | 5,89970845 |
| 216565_x_at | LOC391020 | AL121994 | 1,96729008 | 3,04157071 | 9,1192663 |
| 203514_at | MAP3K3 | BF971923 | 2,1094389 | 3,02907614 | 8,1182283 |
| 210142_x_at | FLOT1 | AF117234.1 | 2,05159552 | 3,02505054 | 8,1182283 |
| 214728_x_at | SMARCA4 | AK026573.1 | 2,03609444 | 3,01437839 | 9,1192663 |
| 219253_at | FAM11B | NM_024121.1 | 2,28545127 | 3,00636045 | 5,89970845 |
| 204716_at | CCDC6 | NM_005436.1 | -2,3683726 | 0,33318165 | 4,00644922 |
| 207606_s_at | ARHGAP12 | NM_018287.1 | -2,2164473 | 0,33302114 | 5,17332085 |
| 202395_at | NSF | NM_006178.1 | -2,7194527 | 0,33229609 | 1,95486287 |
| 215284_at | SNX9 | AF070575.1 | -2,0907117 | 0,33183909 | 6,61229075 |
| 208091_s_at | ECOP | NM_030796.1 | -2,8062284 | 0,33046316 | 1,59856371 |
| 220603_s_at | MCTP2 | NM_018349.1 | -2,4348518 | 0,32856571 | 3,55015917 |
| 206833_s_at | ACYP2 | NM_001108.1 | -2,0195064 | 0,32636362 | 7,42239638 |
| 212943_at | KIAA0528 | AB011100.2 | -2,0072437 | 0,32569571 | 8,1182283 |
| 206683_at | ZNF165 | NM_003447.1 | -1,8851706 | 0,32520713 | 10,2192819 |
| 203988_s_at | FUT8 | NM_004480.1 | -2,060773 | 0,32405019 | 7,42239638 |
| 202255_s_at | SIPA1L1 | NM_015556.1 | -1,9229198 | 0,3237302 | 9,1192663 |
| 220132_s_at | CLEC2D | NM_013269.1 | -2,0191868 | 0,32321251 | 7,42239638 |
| 220368_s_at | SMEK1 | NM_017936.1 | -2,4659549 | 0,32001468 | 3,02553731 |
| 218197_s_at | OXR1 | NM_018002.1 | -1,8816768 | 0,31937923 | 10,2192819 |
| 200996_at | ACTR3 | NM_005721.2 | -2,6526588 | 0,319222 | 2,33361756 |
| 205933_at | SETBP1 | NM_015559.1 | -1,9774106 | 0,31914338 | 8,1182283 |
| 203249_at | EZH1 | AB002386.1 | -2,0367594 | 0,31464351 | 7,42239638 |
| 203502_at | BPGM | NM_001724.1 | -2,3964601 | 0,31444353 | 3,55015917 |

FIG. 15 (Continued)

Table 7 (Continued)

| 211546_x_at | SNCA | L36674.1 | -2,4343101 | 0,31286002 | 3,55015917 |
|---|---|---|---|---|---|
| 217879_at | CDC27 | AL566824 | -2,9334993 | 0,3126572 | 1,05177129 |
| 201996_s_at | SPEN | AL524033 | -2,6443358 | 0,31265507 | 2,33361756 |
| 212985_at | --- | BF115739 | -2,0482276 | 0,31244366 | 7,42239638 |
| 218940_at | C14orf138 | NM_024558.1 | -2,5677494 | 0,3124239 | 2,71838962 |
| 213511_s_at | MTMR1 | AI167164 | -3,0358391 | 0,31133374 | 0,87510658 |
| 205316_at | SLC15A2 | BF223679 | -1,9180707 | 0,31094927 | 9,1192663 |
| 215307_at | ZNF529 | AL109722.1 | -1,9477718 | 0,30994696 | 9,1192663 |
| 201151_s_at | MBNL1 | BF512200 | -2,320375 | 0,30738852 | 4,00644922 |
| 214433_s_at | SELENBP1 | NM_003944.1 | -1,8777349 | 0,30602293 | 10,2192819 |
| 214712_at | SULT1A4 | AK023827.1 | -2,0710264 | 0,30554722 | 6,61229075 |
| 213878_at | LOC642732 /// LOC730793 | AI685944 | -2,3584067 | 0,3029247 | 4,00644922 |
| 207098_s_at | MFN1 | NM_017927.1 | -2,2578302 | 0,3014003 | 4,42294457 |
| 206296_x_at | MAP4K1 | NM_007181.1 | -2,0414899 | 0,29935507 | 7,42239638 |
| 218987_at | ATF7IP | NM_018179.1 | -3,3662149 | 0,29927468 | 0,42671864 |
| 203710_at | ITPR1 | NM_002222.1 | -2,5332913 | 0,29583561 | 2,71838962 |
| 202660_at | ITPR2 | AA834576 | -2,0711395 | 0,29532635 | 6,61229075 |
| 209750_at | NR1D2 | N32859 | -2,1252256 | 0,29356731 | 5,89970845 |
| 208753_s_at | NAP1L1 | BC002387.1 | -2,8003866 | 0,2934489 | 1,75192403 |
| 49485_at | PRDM4 | W22625 | -3,2246655 | 0,29257859 | 0,42671864 |
| 213186_at | DZIP3 | BG502305 | -2,016846 | 0,29217763 | 7,42239638 |
| 204156_at | KIAA0999 | AA044154 | -2,1627702 | 0,29205294 | 5,89970845 |
| 218819_at | INTS6 | NM_012141.1 | -2,5074208 | 0,29178784 | 3,02553731 |
| 200916_at | TAGLN2 | NM_003564.1 | -2,4589761 | 0,29153864 | 3,02553731 |
| 204882_at | ARHGAP25 | NM_014882.1 | -2,1234411 | 0,29127752 | 5,89970845 |
| 218319_at | PELI1 | NM_020651.2 | -2,0866003 | 0,28919601 | 6,61229075 |
| 221781_s_at | DNAJC10 | BG168666 | -2,5631186 | 0,28910006 | 2,71838962 |
| 212492_s_at | JMJD2B | AW237172 | -2,8860543 | 0,28702548 | 1,21621762 |
| 215512_at | MARCH6 | AK000970.1 | -2,1654461 | 0,28515652 | 5,89970845 |
| 208178_x_at | TRIO | NM_007118.1 | -2,1335324 | 0,27545022 | 5,89970845 |
| 221778_at | KIAA1718 | BE217882 | -3,3844054 | 0,27365309 | 0,42671864 |
| 37170_at | BMP2K | AB015331 | -2,0566535 | 0,27221015 | 7,42239638 |
| 215415_s_at | LYST | U70064.1 | -2,2370605 | 0,26800857 | 5,17332085 |
| 207124_s_at | GNB5 | NM_006578.1 | -2,2094444 | 0,26664283 | 5,17332085 |
| 214149_s_at | ATP6V0E1 | AI252582 | -2,161273 | 0,26252172 | 5,89970845 |
| 212838_at | DNMBP | AB023227.1 | -2,5501106 | 0,26030975 | 2,71838962 |
| 202996_at | POLD4 | NM_021173.1 | -2,3634644 | 0,25822519 | 4,00644922 |
| 203620_s_at | FCHSD2 | NM_014824.1 | -2,404688 | 0,25678416 | 3,55015917 |
| 212715_s_at | MICAL3 /// LOC731210 | AB020626.1 | -2,0459226 | 0,25640656 | 7,42239638 |

FIG. 15 (Continued)

Table 7 (Continued)

| 219820_at | SLC6A16 | NM_014037.1 | -2,3127741 | 0,25402939 | 4,42294457 |
|---|---|---|---|---|---|
| 219209_at | IFIH1 | NM_022168.1 | -2,1850413 | 0,24960738 | 5,17332085 |
| 205718_at | ITGB7 | NM_000889.1 | -2,2482195 | 0,24947372 | 5,17332085 |
| 203819_s_at | IGF2BP3 | AU160004 | -2,1948055 | 0,24879372 | 5,17332085 |
| 211085_s_at | STK4 | Z25430.1 | -2,567066 | 0,24804905 | 2,71838962 |
| 202745_at | USP8 | NM_005154.1 | -3,8137974 | 0,24607066 | 0 |
| 203907_s_at | IQSEC1 | NM_014869.1 | -3,2265587 | 0,24524785 | 0,42671864 |
| 204633_s_at | RPS6KA5 | AF074393.1 | -2,1403081 | 0,24424145 | 5,89970845 |
| 219202_at | RHBDF2 | NM_024599.1 | -3,0146822 | 0,24045055 | 0,87510658 |
| 205590_at | RASGRP1 | NM_005739.2 | -2,6813222 | 0,23967427 | 1,95486287 |
| 220386_s_at | EML4 | NM_019063.1 | -2,8393649 | 0,23291614 | 1,59856371 |
| 214787_at | DENND4A | BE268538 | -2,1581618 | 0,2310847 | 5,89970845 |
| 209060_x_at | NCOA3 | AI438999 | -3,4873033 | 0,22884449 | 0,42671864 |
| 205178_s_at | RBBP6 | NM_006910.1 | -3,5393337 | 0,2279856 | 0 |
| 209780_at | PHTF2 | AL136883.1 | -3,3363149 | 0,2272287 | 0,42671864 |
| 214791_at | LOC93349 | AK023116.1 | -3,3731088 | 0,22349241 | 0,42671864 |
| 212112_s_at | STX12 | AI816243 | -2,9874932 | 0,22233899 | 0,87510658 |
| 203241_at | UVRAG | NM_003369.1 | -3,3689384 | 0,21828795 | 0,42671864 |
| 222284_at | SIPA1L3 | AI734111 | -2,5745717 | 0,2158812 | 2,71838962 |
| 214861_at | JMJD2C | AI341811 | -2,6565154 | 0,21278347 | 2,33361756 |
| 206648_at | ZNF571 | NM_016536.1 | -2,5466764 | 0,21223065 | 2,71838962 |
| 214190_x_at | GGA2 | AI799984 | -2,0542295 | 0,20819647 | 7,42239638 |
| 214722_at | NOTCH2NL | AW516297 | -3,1940932 | 0,20557105 | 0,42671864 |
| 219024_at | PLEKHA1 | NM_021622.1 | -2,3432086 | 0,20407716 | 4,00644922 |
| 212577_at | SMCHD1 | AA868754 | -3,8892445 | 0,19114237 | 0 |
| 207057_at | SLC16A7 | NM_004731.1 | -2,6611648 | 0,18553152 | 2,33361756 |
| 220768_s_at | CSNK1G3 | NM_004384.1 | -3,549114 | 0,18366469 | 0 |
| 215716_s_at | ATP2B1 | L14561 | -3,5729522 | 0,17205879 | 0 |
| 210042_s_at | CTSZ | AF073890.1 | -2,7299484 | 0,1557048 | 1,95486287 |
| 205801_s_at | RASGRP3 | NM_015376.1 | -3,1982637 | 0,13440585 | 0,42671864 |
| 211639_x_at | C12orf32 | L23518.1 | -3,4346518 | 0,09711828 | 0,42671864 |
| 205020_s_at | ARL4A | NM_005738.1 | -3,4894217 | 0,09461538 | 0,42671864 |
| 205901_at | PNOC | NM_006228.2 | -3,860291 | 0,09066016 | 0 |
| 210448_s_at | P2RX5 | U49396.1 | -3,7676265 | 0,07820407 | 0 |
| 217258_x_at | IVD | AF043583.1 | -3,7821396 | 0,07493553 | 0 |
| 208536_s_at | BCL2L11 | NM_006538.1 | -4,3112603 | 0,07434928 | 0 |
| 203865_s_at | ADARB1 | NM_015833.1 | -5,4256703 | 0,03622709 | 0 |

(END TABLE 7)

FIG. 16

Table 8

| uniqid | Gene Symbol | Gene ID | Score(d) | Fold Change | q-value(%) |
|---|---|---|---|---|---|
| 213915_at | NKG7 | NM_005601.1 | 5,9831318 | 124,150007 | 0 |
| 212070_at | GPR56 | AL554008 | 5,73936915 | 96,3187643 | 0 |
| 219686_at | STK32B | NM_018401.1 | 5,45473395 | 88,2948568 | 0 |
| 204083_s_at | TPM2 | NM_003289.1 | 7,20051748 | 86,3940066 | 0 |
| 203821_at | HBEGF | NM_001945.1 | 6,38480744 | 67,5119979 | 0 |
| 208890_s_at | PLXNB2 | BC004542.1 | 4,72345808 | 42,4230754 | 0 |
| 211052_s_at | TBCD | BC006364.1 | 5,07807018 | 42,3260017 | 0 |
| 222303_at | --- | AV700891 | 5,60792636 | 39,4783442 | 0 |
| 218051_s_at | NT5DC2 | NM_022908.1 | 5,93174238 | 37,8810751 | 0 |
| 215051_x_at | AIF1 | BF213829 | 3,9867058 | 36,6206186 | 0 |
| 213008_at | KIAA1794 | BG403615 | 6,8447558 | 34,2458799 | 0 |
| 220085_at | HELLS | NM_018063.1 | 6,30636271 | 33,6995088 | 0 |
| 203373_at | SOCS2 | NM_003877.1 | 6,08607159 | 32,4053069 | 0 |
| 204011_at | SPRY2 | NM_005842.1 | 4,15190486 | 27,5782347 | 0 |
| 207030_s_at | CSRP2 | NM_001321.1 | 4,17042586 | 23,4156991 | 0 |
| 202252_at | RAB13 | NM_002870.1 | 5,02241102 | 21,569539 | 0 |
| 212759_s_at | TCF7L2 | AI703074 | 4,23248365 | 20,7147814 | 0 |
| 201329_s_at | ETS2 | NM_005239.1 | 4,64237965 | 19,7262902 | 0 |
| 212013_at | PXDN | D86983.1 | 4,65130577 | 18,7980002 | 0 |
| 207857_at | LILRA2 | NM_006866.1 | 5,07862865 | 17,8578632 | 0 |
| 202870_s_at | PBX2 | NM_004295.1 | 4,77766674 | 14,6909995 | 0 |
| 201890_at | RRM2 | BE966236 | 5,08053951 | 14,6770198 | 0 |
| 206548_at | FLJ23556 | NM_024880.1 | 4,00268159 | 14,6201383 | 0 |
| 210146_x_at | LILRB2 /// LILRA6 | AF004231.1 | 4,15394307 | 13,5145625 | 0 |
| 219654_at | PTPLA | NM_014241.1 | 4,41511417 | 13,2793394 | 0 |
| 214761_at | ZNF423 | AW149417 | 4,35349946 | 12,7991332 | 0 |
| 207697_x_at | LILRB2 | NM_005874.1 | 5,30614535 | 12,4865182 | 0 |
| 218764_at | PRKCH | NM_024064.1 | 4,0121565 | 11,8359631 | 0 |
| 210701_at | CFDP1 | D85939.1 | 5,10871895 | 10,5892109 | 0 |
| 219493_at | SHCBP1 | NM_024745.1 | 4,01527625 | 10,243635 | 0 |
| 214438_at | HLX1 | M60721.1 | 4,29723134 | 10,2208387 | 0 |
| 208808_s_at | HMGB2 | BC000903.1 | 4,97372363 | 7,84746678 | 0 |
| 204759_at | RCBTB2 | NM_001268.1 | 4,08209528 | 7,55128712 | 0 |
| 212124_at | ZMIZ1 | AF070622.1 | 4,75971934 | 7,52865767 | 0 |
| 204529_s_at | TOX | AI961231 | 4,37609578 | 7,44764261 | 0 |
| 202179_at | BLMH | NM_000386.1 | 4,17010673 | 7,02983265 | 0 |
| 222036_s_at | SLC12A4 | AI859865 | 4,74179231 | 6,23057183 | 0 |
| 202503_s_at | KIAA0101 | NM_014736.1 | 4,10776941 | 5,98392529 | 0 |
| 201697_s_at | DNMT1 | NM_001379.1 | 4,19675404 | 5,57618282 | 0 |

FIG. 16 (Continued)

Table 8 (Continued)

| | | | | | |
|---|---|---|---|---|---|
| 208893_s_at | DUSP6 | BC005047.1 | 3,66862036 | 40,7574196 | 0,57442894 |
| 212606_at | WDFY3 | AL536319 | 3,91329197 | 33,5953874 | 0,57442894 |
| 218589_at | P2RY5 | NM_005767.1 | 3,65892475 | 13,7749139 | 0,57442894 |
| 221773_at | ELK3 | AW575374 | 3,76115607 | 12,4445739 | 0,57442894 |
| 210613_s_at | SYNGR1 | BC000731.1 | 3,83409284 | 9,21802227 | 0,57442894 |
| 201416_at | SOX4 | BG528420 | 3,70873057 | 9,11073363 | 0,57442894 |
| 220918_at | C21orf96 | NM_025143.1 | 3,9388066 | 9,02561598 | 0,57442894 |
| 202481_at | DHRS3 | NM_004753.1 | 3,65585579 | 8,99574717 | 0,57442894 |
| 205349_at | GNA15 | NM_002068.1 | 3,85818055 | 8,81999967 | 0,57442894 |
| 219978_s_at | NUSAP1 | NM_018454.1 | 3,75341922 | 7,52342848 | 0,57442894 |
| 38671_at | PLXND1 | AB014520 | 3,76045102 | 6,432274 | 0,57442894 |
| 209832_s_at | CDT1 | AF321125. | 3,86882317 | 6,20121962 | 0,57442894 |
| 34726_at | CACNB3 | U07139 | 3,96005735 | 5,90400041 | 0,57442894 |
| 59697_at | RAB15 | AA582932 | 3,68527588 | 4,63224839 | 0,57442894 |
| 201656_at | ITGA6 | NM_000210.1 | 3,60896361 | 76,5955602 | 0,72150495 |
| 1405_i_at | CCL5 | M21121 | 3,57230879 | 28,7544829 | 0,72150495 |
| 201830_s_at | NET1 | NM_005863.1 | 3,63698838 | 14,5781514 | 0,72150495 |
| 203092_at | TIMM44 | AF026030.1 | 3,59826444 | 11,1866686 | 0,72150495 |
| 218694_at | ARMCX1 | NM_016608.1 | 3,47919823 | 10,2024167 | 0,72150495 |
| 206995_x_at | SCARF1 | NM_003693.1 | 3,51128331 | 10,1825809 | 0,72150495 |
| 213056_at | FRMD4B | AU145019 | 3,55236395 | 8,57684328 | 0,72150495 |
| 202039_at | TIAF1 /// MYO18A | NM_004740.1 | 3,56665425 | 7,06888385 | 0,72150495 |
| 209576_at | GNAI1 | AL049933.1 | 3,46174866 | 6,50887246 | 0,72150495 |
| 213518_at | PRKCI | AI689429 | 3,47730733 | 6,35770691 | 0,72150495 |
| 213827_at | SNX26 | AL137579.1 | 3,58450977 | 5,51531146 | 0,72150495 |
| 204790_at | SMAD7 | NM_005904.1 | 3,38259364 | 10,0300803 | 0,87510658 |
| 201566_x_at | ID2 /// ID2B | D13891.1 | 3,35091806 | 9,78171334 | 0,87510658 |
| 204900_x_at | SAP30 | NM_003864.1 | 3,42606119 | 9,54041157 | 0,87510658 |
| 209892_at | FUT4 | AF305083.1 | 3,422068 | 6,88499993 | 0,87510658 |
| 204825_at | MELK | NM_014791.1 | 3,42986174 | 5,94944876 | 0,87510658 |
| 207011_s_at | PTK7 | NM_002821.1 | 3,4188741 | 5,88786939 | 0,87510658 |
| 202392_s_at | PISD | NM_014338.1 | 3,38035448 | 4,10380166 | 0,87510658 |
| 203564_at | FANCG | NM_004629.1 | 3,43587548 | 3,96253796 | 0,87510658 |

(END TABLE 8)

FIG. 17

Table 9

| uniqid | Gene Symbol | Gene ID | Score(d) | Fold Change | q-value(%) |
|---|---|---|---|---|---|
| 204083_s_at | TPM2 | NM_003289.1 | 7,20051748 | 86,3940066 | 0 |
| 213008_at | KIAA1794 | BG403615 | 6,8447558 | 34,2458799 | 0 |
| 203821_at | HBEGF | NM_001945.1 | 6,38480744 | 67,5119979 | 0 |
| 220085_at | HELLS | NM_018063.1 | 6,30636271 | 33,6995088 | 0 |
| 203373_at | SOCS2 | NM_003877.1 | 6,08607159 | 32,4053069 | 0 |
| 218051_s_at | NT5DC2 | NM_022908.1 | 5,93174238 | 37,8810751 | 0 |
| 212070_at | GPR56 | AL554008 | 5,73936915 | 96,3187643 | 0 |
| 222303_at | --- | AV700891 | 5,60792636 | 39,4783442 | 0 |
| 219686_at | STK32B | NM_018401.1 | 5,45473395 | 88,2948568 | 0 |
| 207697_x_at | LILRB2 | NM_005874.1 | 5,30614535 | 12,4865182 | 0 |
| 201890_at | RRM2 | BE966236 | 5,08053951 | 14,6770198 | 0 |
| 207857_at | LILRA2 | NM_006866.1 | 5,07862865 | 17,8578632 | 0 |
| 211052_s_at | TBCD | BC006364.1 | 5,07807018 | 42,3260017 | 0 |
| 202870_s_at | PBX2 | NM_004295.1 | 4,77766674 | 14,6909995 | 0 |
| 212124_at | ZMIZ1 | AF070622.1 | 4,75971934 | 7,52865767 | 0 |
| 208890_s_at | PLXNB2 | BC004542.1 | 4,72345808 | 42,4230754 | 0 |
| 212013_at | PXDN | D86983.1 | 4,65130577 | 18,7980002 | 0 |
| 201329_s_at | ETS2 | NM_005239.1 | 4,64237965 | 19,7262902 | 0 |
| 214761_at | ZNF423 | AW149417 | 4,35349946 | 12,7991332 | 0 |
| 212759_s_at | TCF7L2 | AI703074 | 4,23248365 | 20,7147814 | 0 |
| 207030_s_at | CSRP2 | NM_001321.1 | 4,17042586 | 23,4156991 | 0 |
| 210146_x_at | LILRB2 /// LILRA6 | AF004231.1 | 4,15394307 | 13,5145625 | 0 |
| 204011_at | SPRY2 | NM_005842.1 | 4,15190486 | 27,5782347 | 0 |
| 204759_at | RCBTB2 | NM_001268.1 | 4,08209528 | 7,55128712 | 0 |
| 219493_at | SHCBP1 | NM_024745.1 | 4,01527625 | 10,243635 | 0 |
| 206548_at | FLJ23556 | NM_024880.1 | 4,00268159 | 14,6201383 | 0 |
| 34726_at | CACNB3 | U07139 | 3,96005735 | 5,90400041 | 0,57442894 |
| 220918_at | C21orf96 | NM_025143.1 | 3,9388066 | 9,02561598 | 0,57442894 |
| 212606_at | WDFY3 | AL536319 | 3,91329197 | 33,5953874 | 0,57442894 |
| 221773_at | ELK3 | AW575374 | 3,76115607 | 12,4445739 | 0,57442894 |
| 38671_at | PLXND1 | AB014520 | 3,76045102 | 6,432274 | 0,57442894 |
| 219978_s_at | NUSAP1 | NM_018454.1 | 3,75341922 | 7,52342848 | 0,57442894 |
| 201416_at | SOX4 | BG528420 | 3,70873057 | 9,11073363 | 0,57442894 |
| 208893_s_at | DUSP6 | BC005047.1 | 3,66862036 | 40,7574196 | 0,57442894 |
| 218589_at | P2RY5 | NM_005767.1 | 3,65892475 | 13,7749139 | 0,57442894 |
| 202481_at | DHRS3 | NM_004753.1 | 3,65585579 | 8,99574717 | 0,57442894 |
| 201830_s_at | NET1 | NM_005863.1 | 3,63698838 | 14,5781514 | 0,72150495 |
| 201656_at | ITGA6 | NM_000210.1 | 3,60896361 | 76,5955602 | 0,72150495 |

FIG. 17 (Continued)

Table 9 (Continued)

| | | | | | |
|---|---|---|---|---|---|
| 213827_at | SNX26 | AL137579.1 | 3,58450977 | 5,51531146 | 0,72150495 |
| 1405_i_at | CCL5 | M21121 | 3,57230879 | 28,7544829 | 0,72150495 |
| 202039_at | TIAF1 /// MYO18A | NM_004740.1 | 3,56665425 | 7,06888385 | 0,72150495 |
| 213056_at | FRMD4B | AU145019 | 3,55236395 | 8,57684328 | 0,72150495 |
| 204825_at | MELK | NM_014791.1 | 3,42986174 | 5,94944876 | 0,87510658 |
| 204900_x_at | SAP30 | NM_003864.1 | 3,42606119 | 9,54041157 | 0,87510658 |
| 204790_at | SMAD7 | NM_005904.1 | 3,38259364 | 10,0300803 | 0,87510658 |
| 202392_s_at | PISD | NM_014338.1 | 3,38035448 | 4,10380166 | 0,87510658 |
| 201566_x_at | ID2 /// ID2B | D13891.1 | 3,35091806 | 9,78171334 | 0,87510658 |

(END TABLE 9)

FIG. 18

Table 10

| uniqid | Gene Symbol | Gene ID | Score(d) | Fold Change | q-value(%) |
|---|---|---|---|---|---|
| 213915_at | NKG7 | NM_005601.1 | 5,9831318 | 124,150007 | 0 |
| 210701_at | CFDP1 | D85939.1 | 5,10871895 | 10,5892109 | 0 |
| 202252_at | RAB13 | NM_002870.1 | 5,02241102 | 21,569539 | 0 |
| 208808_s_at | HMGB2 | BC000903.1 | 4,97372363 | 7,84746678 | 0 |
| 222036_s_at | SLC12A4 | AI859865 | 4,74179231 | 6,23057183 | 0 |
| 219654_at | PTPLA | NM_014241.1 | 4,41511417 | 13,2793394 | 0 |
| 204529_s_at | TOX | AI961231 | 4,37609578 | 7,44764261 | 0 |
| 214438_at | HLX1 | M60721.1 | 4,29723134 | 10,2208387 | 0 |
| 201697_s_at | DNMT1 | NM_001379.1 | 4,19675404 | 5,57618282 | 0 |
| 202179_at | BLMH | NM_000386.1 | 4,17010673 | 7,02983265 | 0 |
| 202503_s_at | KIAA0101 | NM_014736.1 | 4,10776941 | 5,98392529 | 0 |
| 218764_at | PRKCH | NM_024064.1 | 4,0121565 | 11,8359631 | 0 |
| 215051_x_at | AIF1 | BF213829 | 3,9867058 | 36,6206186 | 0 |
| 209832_s_at | CDT1 | AF321125. | 3,86882317 | 6,20121962 | 0,57442894 |
| 205349_at | GNA15 | NM_002068.1 | 3,85818055 | 8,81999967 | 0,57442894 |
| 210613_s_at | SYNGR1 | BC000731.1 | 3,83409284 | 9,21802227 | 0,57442894 |
| 59697_at | RAB15 | AA582932 | 3,68527588 | 4,63224839 | 0,57442894 |
| 203092_at | TIMM44 | AF026030.1 | 3,59826444 | 11,1866686 | 0,72150495 |
| 206995_x_at | SCARF1 | NM_003693.1 | 3,51128331 | 10,1825809 | 0,72150495 |
| 218694_at | ARMCX1 | NM_016608.1 | 3,47919823 | 10,2024167 | 0,72150495 |
| 213518_at | PRKCI | AI689429 | 3,47730733 | 6,35770691 | 0,72150495 |
| 209576_at | GNAI1 | AL049933.1 | 3,46174866 | 6,50887246 | 0,72150495 |
| 203564_at | FANCG | NM_004629.1 | 3,43587548 | 3,96253796 | 0,87510658 |
| 209892_at | FUT4 | AF305083.1 | 3,422068 | 6,88499993 | 0,87510658 |
| 207011_s_at | PTK7 | NM_002821.1 | 3,4188741 | 5,88786939 | 0,87510658 |

FIG. 19

Table 11

| uniqid | Gene Symbol | Gene ID | Score(d) | Fold Change | q-value(%) |
|---|---|---|---|---|---|
| 205997_at | ADAM28 | NM_021778.1 | -3,8228874 | 0,064756098 | 0 |
| 203865_s_at | ADARB1 | NM_015833.1 | -5,4256703 | 0,036227091 | 0 |
| 215716_s_at | ATP2B1 | L14561 | -3,5729522 | 0,172058795 | 0 |
| 208536_s_at | BCL2L11 | NM_006538.1 | -4,3112603 | 0,074349278 | 0 |
| 210538_s_at | BIRC3 | U37546.1 | -4,0545991 | 0,091399305 | 0 |
| 206126_at | BLR1 | NM_001716.1 | -4,5020183 | 0,046081141 | 0 |
| 204192_at | CD37 | NM_001774.1 | -4,022886 | 0,118122656 | 0 |
| 221059_s_at | COTL1 | NM_021615.1 | -3,6982513 | 0,205847248 | 0 |
| 205544_s_at | CR2 | NM_001877.1 | -4,2440236 | 0,074832471 | 0 |
| 220768_s_at | CSNK1G3 | NM_004384.1 | -3,549114 | 0,18366469 | 0 |
| 221586_s_at | E2F5 | U15642.1 | -4,1164925 | 0,064768569 | 0 |
| 221239_s_at | FCRL2 | NM_030764.1 | -3,9513744 | 0,065241567 | 0 |
| 214916_x_at | IFI6 /// SIX6 | BG340548 | -3,5679398 | 0,17232494 | 0 |
| 217258_x_at | IVD | AF043583.1 | -3,7821396 | 0,074935532 | 0 |
| 212314_at | KIAA0746 | AB018289.1 | -3,7004078 | 0,155759163 | 0 |
| 211637_x_at | LOC652128 | L23516.1 | -3,9101367 | 0,0499538 | 0 |
| 202625_at | LYN | AI356412 | -4,856636 | 0,086097601 | 0 |
| 219574_at | MARCH1 | NM_017923.1 | -3,8175614 | 0,084416318 | 0 |
| 202443_x_at | NOTCH2 | AA291203 | -4,4315558 | 0,136677283 | 0 |
| 211635_x_at | NTN2L | M24670.1 | -4,1625562 | 0,099988894 | 0 |
| 219073_s_at | OSBPL10 | NM_017784.1 | -4,3409957 | 0,065720909 | 0 |
| 210448_s_at | P2RX5 | U49396.1 | -3,7676265 | 0,078204068 | 0 |
| 203378_at | PCF11 | AB020631.1 | -4,1280387 | 0,193088137 | 0 |
| 209422_at | PHF20 | AL109965 | -4,1900871 | 0,180084568 | 0 |
| 205901_at | PNOC | NM_006228.2 | -3,860291 | 0,090660159 | 0 |
| 205178_s_at | RBBP6 | NM_006910.1 | -3,5393337 | 0,227985596 | 0 |
| 204207_s_at | RNGTT | AB012142.1 | -4,1902934 | 0,24425702 | 0 |
| 212577_at | SMCHD1 | AA868754 | -3,8892445 | 0,191142371 | 0 |
| 218404_at | SNX10 | NM_013322.1 | -3,627697 | 0,095632598 | 0 |
| 202863_at | SP100 | NM_003113.1 | -3,6222817 | 0,259032563 | 0 |
| 207777_s_at | SP140 | NM_007237.1 | -3,6880715 | 0,173329275 | 0 |
| 207616_s_at | TANK | NM_004180.1 | -3,6819506 | 0,175224012 | 0 |
| 202080_s_at | TRAK1 | NM_014965.1 | -3,5454038 | 0,153656578 | 0 |
| 202745_at | USP8 | NM_005154.1 | -3,8137974 | 0,246070662 | 0 |
| 213106_at | --- | AI769688 | -3,3899591 | 0,214358946 | 0,42671864 |
| 205020_s_at | ARL4A | NM_005738.1 | -3,4894217 | 0,094615376 | 0,42671864 |
| 218987_at | ATF7IP | NM_018179.1 | -3,3662149 | 0,299274683 | 0,42671864 |
| 219667_s_at | BANK1 | NM_017935.1 | -3,29323 | 0,166347181 | 0,42671864 |
| 211639_x_at | C12orf32 | L23518.1 | -3,4346518 | 0,097118283 | 0,42671864 |
| 218100_s_at | IFT57 | NM_018010.1 | -3,5065173 | 0,210267316 | 0,42671864 |

FIG. 19 (Continued)

Table 11 (Continued)

| | | | | | |
|---|---|---|---|---|---|
| 203907_s_at | IQSEC1 | NM_014869.1 | -3,2265587 | 0,245247846 | 0,42671864 |
| 221778_at | KIAA1718 | BE217882 | -3,3844054 | 0,273653091 | 0,42671864 |
| 205306_x_at | KMO | AI074145 | -3,3001967 | 0,233159098 | 0,42671864 |
| 217388_s_at | KYNU | D55639.1 | -3,4516101 | 0,091151507 | 0,42671864 |
| 212098_at | LOC151162 | AL134724 | -3,2673507 | 0,286941307 | 0,42671864 |
| 213142_x_at | LOC54103 | AV700415 | -3,2668565 | 0,182541806 | 0,42671864 |
| 214791_at | LOC93349 | AK023116.1 | -3,3731088 | 0,223492405 | 0,42671864 |
| 203640_at | MBNL2 | BE328496 | -3,3016467 | 0,162928548 | 0,42671864 |
| 203414_at | MMD | NM_012329.1 | -3,2078372 | 0,193953732 | 0,42671864 |
| 203037_s_at | MTSS1 | NM_014751.1 | -3,377199 | 0,162405996 | 0,42671864 |
| 209060_x_at | NCOA3 | AI438999 | -3,4873033 | 0,228844492 | 0,42671864 |
| 214722_at | NOTCH2NL | AW516297 | -3,1940932 | 0,20557105 | 0,42671864 |
| 209780_at | PHTF2 | AL136883.1 | -3,3363149 | 0,227228697 | 0,42671864 |
| 49485_at | PRDM4 | W22625 | -3,2246655 | 0,292578593 | 0,42671864 |
| 205801_s_at | RASGRP3 | NM_015376.1 | -3,1982637 | 0,134405846 | 0,42671864 |
| 201779_s_at | RNF13 | AF070558.1 | -3,4733991 | 0,263067528 | 0,42671864 |
| 56256_at | SIDT2 | AA150165 | -3,4033268 | 0,274066257 | 0,42671864 |
| 201998_at | ST6GAL1 | AI743792 | -3,2857762 | 0,205815393 | 0,42671864 |
| 201079_at | SYNGR2 | NM_004710.1 | -3,437189 | 0,184722933 | 0,42671864 |
| 203241_at | UVRAG | NM_003369.1 | -3,3689384 | 0,218287953 | 0,42671864 |
| 219228_at | ZNF331 | NM_018555.2 | -3,1973294 | 0,181238089 | 0,42671864 |
| 209765_at | ADAM19 | Y13786.2 | -3,0624331 | 0,243869014 | 0,65793623 |
| 205882_x_at | ADD3 | AI818488 | -3,1077658 | 0,256761269 | 0,65793623 |
| 210889_s_at | FCGR2B | M31933.1 | -3,1558454 | 0,122452015 | 0,65793623 |
| 213515_x_at | HBG1 /// HBG2 | AI133353 | -3,07695 | 0,110213181 | 0,65793623 |
| 216557_x_at | IFI6 | U92706 | -3,107852 | 0,197220091 | 0,65793623 |
| 219032_x_at | OPN3 | NM_014322.1 | -3,1517305 | 0,178085743 | 0,65793623 |
| 214615_at | P2RY10 | NM_014499.1 | -3,0878249 | 0,153244303 | 0,65793623 |
| 213309_at | PLCL2 | AL117515.1 | -3,119547 | 0,254069156 | 0,65793623 |
| 209307_at | SWAP70 | AB014540.1 | -3,1114961 | 0,277277515 | 0,65793623 |
| 202864_s_at | CDC20 | AI695173 | -3,0356439 | 0,26606517 | 0,87510658 |
| 213511_s_at | MTMR1 | AI167164 | -3,0358391 | 0,311333739 | 0,87510658 |
| 219202_at | RHBDF2 | NM_024599.1 | -3,0146822 | 0,240450548 | 0,87510658 |
| 212112_s_at | STX12 | AI816243 | -2,9874932 | 0,222338992 | 0,87510658 |

(END TABLE 11)

FIG. 20

Table 12

| uniqid | Gene Symbol | Gene ID | Score(d) | Fold Change | q-value(%) |
|---|---|---|---|---|---|
| 206126_at | BLR1 | NM_001716.1 | -4,5020183 | 0,046081141 | 0 |
| 211637_x_at | LOC652128 | L23516.1 | -3,9101367 | 0,0499538 | 0 |
| 205997_at | ADAM28 | NM_021778.1 | -3,8228874 | 0,064756098 | 0 |
| 221586_s_at | E2F5 | U15642.1 | -4,1164925 | 0,064768569 | 0 |
| 221239_s_at | FCRL2 | NM_030764.1 | -3,9513744 | 0,065241567 | 0 |
| 219073_s_at | OSBPL10 | NM_017784.1 | -4,3409957 | 0,065720909 | 0 |
| 205544_s_at | CR2 | NM_001877.1 | -4,2440236 | 0,074832471 | 0 |
| 219574_at | MARCH1 | NM_017923.1 | -3,8175614 | 0,084416318 | 0 |
| 202625_at | LYN | AI356412 | -4,856636 | 0,086097601 | 0 |
| 210538_s_at | BIRC3 | U37546.1 | -4,0545991 | 0,091399305 | 0 |
| 218404_at | SNX10 | NM_013322.1 | -3,627697 | 0,095632598 | 0 |
| 211635_x_at | NTN2L | M24670.1 | -4,1625562 | 0,099988894 | 0 |
| 204192_at | CD37 | NM_001774.1 | -4,022886 | 0,118122656 | 0 |
| 202443_x_at | NOTCH2 | AA291203 | -4,4315558 | 0,136677283 | 0 |
| 202080_s_at | TRAK1 | NM_014965.1 | -3,5454038 | 0,153656578 | 0 |
| 212314_at | KIAA0746 | AB018289.1 | -3,7004078 | 0,155759163 | 0 |
| 214916_x_at | IFI6 /// SIX6 | BG340548 | -3,5679398 | 0,17232494 | 0 |
| 207777_s_at | SP140 | NM_007237.1 | -3,6880715 | 0,173329275 | 0 |
| 207616_s_at | TANK | NM_004180.1 | -3,6819506 | 0,175224012 | 0 |
| 209422_at | PHF20 | AL109965 | -4,1900871 | 0,180084568 | 0 |
| 203378_at | PCF11 | AB020631.1 | -4,1280387 | 0,193088137 | 0 |
| 221059_s_at | COTL1 | NM_021615.1 | -3,6982513 | 0,205847248 | 0 |
| 204207_s_at | RNGTT | AB012142.1 | -4,1902934 | 0,24425702 | 0 |
| 202863_at | SP100 | NM_003113.1 | -3,6222817 | 0,259032563 | 0 |
| 217388_s_at | KYNU | D55639.1 | -3,4516101 | 0,091151507 | 0,42671864 |
| 203037_s_at | MTSS1 | NM_014751.1 | -3,377199 | 0,162405996 | 0,42671864 |
| 203640_at | MBNL2 | BE328496 | -3,3016467 | 0,162928548 | 0,42671864 |
| 219667_s_at | BANK1 | NM_017935.1 | -3,29323 | 0,166347181 | 0,42671864 |
| 219228_at | ZNF331 | NM_018555.2 | -3,1973294 | 0,181238089 | 0,42671864 |
| 213142_x_at | LOC54103 | AV700415 | -3,2668565 | 0,182541806 | 0,42671864 |
| 201079_at | SYNGR2 | NM_004710.1 | -3,437189 | 0,184722933 | 0,42671864 |
| 203414_at | MMD | NM_012329.1 | -3,2078372 | 0,193953732 | 0,42671864 |
| 201998_at | ST6GAL1 | AI743792 | -3,2857762 | 0,205815393 | 0,42671864 |
| 218100_s_at | IFT57 | NM_018010.1 | -3,5065173 | 0,210267316 | 0,42671864 |
| 213106_at | --- | AI769688 | -3,3899591 | 0,214358946 | 0,42671864 |
| 205306_x_at | KMO | AI074145 | -3,3001967 | 0,233159098 | 0,42671864 |
| 201779_s_at | RNF13 | AF070558.1 | -3,4733991 | 0,263067528 | 0,42671864 |
| 56256_at | SIDT2 | AA150165 | -3,4033268 | 0,274066257 | 0,42671864 |
| 212098_at | LOC151162 | AL134724 | -3,2673507 | 0,286941307 | 0,42671864 |
| 213515_x_at | HBG1 /// HBG2 | AI133353 | -3,07695 | 0,110213181 | 0,65793623 |

FIG. 20 (Continued)

Table 12 (Continued)

| 210889_s_at | FCGR2B | M31933.1 | -3,1558454 | 0,122452015 | 0,65793623 |
|---|---|---|---|---|---|
| 214615_at | P2RY10 | NM_014499.1 | -3,0878249 | 0,153244303 | 0,65793623 |
| 219032_x_at | OPN3 | NM_014322.1 | -3,1517305 | 0,178085743 | 0,65793623 |
| 209765_at | ADAM19 | Y13786.2 | -3,0624331 | 0,243869014 | 0,65793623 |
| 213309_at | PLCL2 | AL117515.1 | -3,119547 | 0,254069156 | 0,65793623 |
| 205882_x_at | ADD3 | AI818488 | -3,1077658 | 0,256761269 | 0,65793623 |
| 209307_at | SWAP70 | AB014540.1 | -3,1114961 | 0,277277515 | 0,65793623 |
| 202864_s_at | CDC20 | AI695173 | -3,0356439 | 0,26606517 | 0,87510658 |

(END TABLE 12)

FIG. 21

Table 13

| uniqid | Gene Symbol | Gene ID | Score(d) | Fold Change | q-value(%) |
|---|---|---|---|---|---|
| 205178_s_at | RBBP6 | NM_006910.1 | -3,5393337 | 0,227985596 | 0 |
| 220768_s_at | CSNK1G3 | NM_004384.1 | -3,549114 | 0,18366469 | 0 |
| 215716_s_at | ATP2B1 | L14561 | -3,5729522 | 0,172058795 | 0 |
| 210448_s_at | P2RX5 | U49396.1 | -3,7676265 | 0,078204068 | 0 |
| 217258_x_at | IVD | AF043583.1 | -3,7821396 | 0,074935532 | 0 |
| 202745_at | USP8 | NM_005154.1 | -3,8137974 | 0,246070662 | 0 |
| 205901_at | PNOC | NM_006228.2 | -3,860291 | 0,090660159 | 0 |
| 212577_at | SMCHD1 | AA868754 | -3,8892445 | 0,191142371 | 0 |
| 208536_s_at | BCL2L11 | NM_006538.1 | -4,3112603 | 0,074349278 | 0 |
| 203865_s_at | ADARB1 | NM_015833.1 | -5,4256703 | 0,036227091 | 0 |
| 214722_at | NOTCH2NL | AW516297 | -3,1940932 | 0,20557105 | 0,42671864 |
| 205801_s_at | RASGRP3 | NM_015376.1 | -3,1982637 | 0,134405846 | 0,42671864 |
| 49485_at | PRDM4 | W22625 | -3,2246655 | 0,292578593 | 0,42671864 |
| 203907_s_at | IQSEC1 | NM_014869.1 | -3,2265587 | 0,245247846 | 0,42671864 |
| 209780_at | PHTF2 | AL136883.1 | -3,3363149 | 0,227228697 | 0,42671864 |
| 218987_at | ATF7IP | NM_018179.1 | -3,3662149 | 0,299274683 | 0,42671864 |
| 203241_at | UVRAG | NM_003369.1 | -3,3689384 | 0,218287953 | 0,42671864 |
| 214791_at | LOC93349 | AK023116.1 | -3,3731088 | 0,223492405 | 0,42671864 |
| 221778_at | KIAA1718 | BE217882 | -3,3844054 | 0,273653091 | 0,42671864 |
| 211639_x_at | C12orf32 | L23518.1 | -3,4346518 | 0,097118283 | 0,42671864 |
| 209060_x_at | NCOA3 | AI438999 | -3,4873033 | 0,228844492 | 0,42671864 |
| 205020_s_at | ARL4A | NM_005738.1 | -3,4894217 | 0,094615376 | 0,42671864 |
| 212112_s_at | STX12 | AI816243 | -2,9874932 | 0,222338992 | 0,87510658 |
| 219202_at | RHBDF2 | NM_024599.1 | -3,0146822 | 0,240450548 | 0,87510658 |
| 213511_s_at | MTMR1 | AI167164 | -3,0358391 | 0,311333739 | 0,87510658 |

FIG. 22

Table 14

| uniqid | Gene Symbol | Gene ID | ALL score | FEB score | Centroid distance |
|---|---|---|---|---|---|
| 219686_at | STK32B | NM_018401.1 | 0,3039 | -1,5195 | 1,2156 |
| 211052_s_at | TBCD | BC006364.1 | 0,1653 | -0,8266 | 0,6613 |
| 203373_at | SOCS2 | NM_003877.1 | 0,1634 | -0,817 | 0,6536 |
| 204083_s_at | TPM2 | NM_003289.1 | 0,1532 | -0,7661 | 0,6129 |
| 214192_at | NUP88 | Y08613.1 | -0,1487 | 0,7437 | 0,595 |
| 213008_at | FANCI | BG403615 | 0,1421 | -0,7106 | 0,5685 |
| 202252_at | RAB13 | NM_002870.1 | 0,1295 | -0,6477 | 0,5182 |
| 203821_at | HBEGF | NM_001945.1 | 0,1292 | -0,6462 | 0,517 |
| 212070_at | GPR56 | AL554008 | 0,1083 | -0,5416 | 0,4333 |
| 203865_s_at | ADARB1 | NM_015833.1 | -0,1049 | 0,5244 | 0,4195 |
| 218051_s_at | NT5DC2 | NM_022908.1 | 0,1042 | -0,5208 | 0,4166 |
| 220085_at | HELLS | NM_018063.1 | 0,0987 | -0,4933 | 0,3946 |
| 207030_s_at | CSRP2 | NM_001321.1 | 0,0952 | -0,4762 | 0,381 |
| 221349_at | VPREB1 | NM_007128.1 | 0,0922 | -0,4608 | 0,3686 |
| 222303_at | --- | AV700891 | 0,0855 | -0,4275 | 0,342 |
| 206126_at | BLR1 | NM_001716.1 | -0,0842 | 0,4212 | 0,337 |
| 210356_x_at | MS4A1 | BC002807.1 | -0,0813 | 0,4066 | 0,3253 |
| 217418_x_at | MS4A1 | X12530.1 | -0,073 | 0,3652 | 0,2922 |
| 208893_s_at | DUSP6 | BC005047.1 | 0,0652 | -0,3259 | 0,2607 |
| 216984_x_at | CKAP2 | D84143.1 | -0,0472 | 0,2358 | 0,1886 |
| 220570_at | RETN | NM_020415.2 | 0,0421 | -0,2103 | 0,1682 |
| 201890_at | RRM2 | BE966236 | 0,0419 | -0,2094 | 0,1675 |
| 219271_at | GALNT14 | NM_024572.1 | 0,0413 | -0,2066 | 0,1653 |
| 204118_at | CD48 | NM_001778.1 | -0,0394 | 0,1971 | 0,1577 |
| 212606_at | WDFY3 | AL536319 | 0,0362 | -0,1812 | 0,145 |
| 210448_s_at | P2RX5 | U49396.1 | -0,0336 | 0,1678 | 0,1342 |
| 208808_s_at | HMGB2 | BC000903.1 | 0,0323 | -0,1615 | 0,1292 |
| 202625_at | LYN | AI356412 | -0,0319 | 0,1594 | 0,1275 |
| 219452_at | DPEP2 | NM_022355.1 | -0,0313 | 0,1567 | 0,1254 |
| 202870_s_at | CDC20 | NM_004295.1 | 0,0255 | -0,1275 | 0,102 |
| 208536_s_at | BCL2L11 | NM_006538.1 | -0,0213 | 0,1064 | 0,0851 |
| 212577_at | SMCHD1 | AA868754 | -0,0184 | 0,092 | 0,0736 |
| 213095_x_at | AIF1 | AF299327.1 | 0,0178 | -0,0892 | 0,0714 |
| 217875_s_at | TMEPAI | NM_020182.1 | -0,0143 | 0,0714 | 0,0571 |
| 211010_s_at | NCR3 | AF031138.1 | -0,0134 | 0,067 | 0,0536 |
| 212013_at | PXDN | D86983.1 | 0,0112 | -0,0562 | 0,045 |
| 212124_at | ZMIZ1 | AF070622.1 | 0,0103 | -0,0513 | 0,041 |
| 219654_at | PTPLA | NM_014241.1 | 0,0096 | -0,048 | 0,0384 |
| 207697_x_at | LILRB2 | NM_005874.1 | 0,0087 | -0,0437 | 0,035 |

FIG. 22 (Continued)

Table 14 (Continued)

| 205997_at | ADAM28 | NM_021778.1 | -0,0071 | 0,0355 | 0,0284 |
|---|---|---|---|---|---|
| 201841_s_at | HSPB1 | NM_001540.2 | 0,0036 | -0,018 | 0,0144 |
| 207857_at | LILRA2 | NM_006866.1 | 0,002 | -0,0101 | 0,0081 |

(END TABLE 14)

FIG. 23

Table 15

| uniqid | Gene Symbol | Gene ID | ALL score | FEB score | Centroid distance |
|---|---|---|---|---|---|
| 219686_at | STK32B | NM_018401.1 | 0,3039 | -1,5195 | 1,2156 |
| 211052_s_at | TBCD | BC006364.1 | 0,1653 | -0,8266 | 0,6613 |
| 204083_s_at | TPM2 | NM_003289.1 | 0,1532 | -0,7661 | 0,6129 |
| 203821_at | HBEGF | NM_001945.1 | 0,1292 | -0,6462 | 0,517 |
| 207030_s_at | CSRP2 | NM_001321.1 | 0,0952 | -0,4762 | 0,381 |
| 221349_at | VPREB1 | NM_007128.1 | 0,0922 | -0,4608 | 0,3686 |
| 208893_s_at | DUSP6 | BC005047.1 | 0,0652 | -0,3259 | 0,2607 |
| 210448_s_at | P2RX5 | U49396.1 | -0,0336 | 0,1678 | 0,1342 |
| 219452_at | DPEP2 | NM_022355.1 | -0,0313 | 0,1567 | 0,1254 |

FIG. 24

Table 16

| uniqid | Gene Symbol | Gene ID | ALL score | FEB score | Centroid distance |
|---|---|---|---|---|---|
| 203373_at | SOCS2 | NM_003877.1 | 0,1634 | -0,817 | 0,6536 |
| 214192_at | NUP88 | Y08613.1 | -0,1487 | 0,7437 | 0,595 |
| 213008_at | FANCI | BG403615 | 0,1421 | -0,7106 | 0,5685 |
| 202252_at | RAB13 | NM_002870.1 | 0,1295 | -0,6477 | 0,5182 |
| 212070_at | GPR56 | AL554008 | 0,1083 | -0,5416 | 0,4333 |
| 203865_s_at | ADARB1 | NM_015833.1 | -0,1049 | 0,5244 | 0,4195 |
| 218051_s_at | NT5DC2 | NM_022908.1 | 0,1042 | -0,5208 | 0,4166 |
| 220085_at | HELLS | NM_018063.1 | 0,0987 | -0,4933 | 0,3946 |
| 222303_at | --- | AV700891 | 0,0855 | -0,4275 | 0,342 |
| 206126_at | BLR1 | NM_001716.1 | -0,0842 | 0,4212 | 0,337 |
| 210356_x_at | MS4A1 | BC002807.1 | -0,0813 | 0,4066 | 0,3253 |
| 217418_x_at | MS4A1 | X12530.1 | -0,073 | 0,3652 | 0,2922 |
| 216984_x_at | CKAP2 | D84143.1 | -0,0472 | 0,2358 | 0,1886 |
| 220570_at | RETN | NM_020415.2 | 0,0421 | -0,2103 | 0,1682 |
| 201890_at | RRM2 | BE966236 | 0,0419 | -0,2094 | 0,1675 |
| 219271_at | GALNT14 | NM_024572.1 | 0,0413 | -0,2066 | 0,1653 |
| 204118_at | CD48 | NM_001778.1 | -0,0394 | 0,1971 | 0,1577 |
| 212606_at | WDFY3 | AL536319 | 0,0362 | -0,1812 | 0,145 |
| 208808_s_at | HMGB2 | BC000903.1 | 0,0323 | -0,1615 | 0,1292 |
| 202625_at | LYN | AI356412 | -0,0319 | 0,1594 | 0,1275 |
| 202870_s_at | CDC20 | NM_004295.1 | 0,0255 | -0,1275 | 0,102 |
| 208536_s_at | BCL2L11 | NM_006538.1 | -0,0213 | 0,1064 | 0,0851 |
| 212577_at | SMCHD1 | AA868754 | -0,0184 | 0,092 | 0,0736 |
| 213095_x_at | AIF1 | AF299327.1 | 0,0178 | -0,0892 | 0,0714 |
| 217875_s_at | TMEPAI | NM_020182.1 | -0,0143 | 0,0714 | 0,0571 |
| 211010_s_at | NCR3 | AF031138.1 | -0,0134 | 0,067 | 0,0536 |
| 212013_at | PXDN | D86983.1 | 0,0112 | -0,0562 | 0,045 |
| 212124_at | ZMIZ1 | AF070622.1 | 0,0103 | -0,0513 | 0,041 |
| 219654_at | PTPLA | NM_014241.1 | 0,0096 | -0,048 | 0,0384 |
| 207697_x_at | LILRB2 | NM_005874.1 | 0,0087 | -0,0437 | 0,035 |
| 205997_at | ADAM28 | NM_021778.1 | -0,0071 | 0,0355 | 0,0284 |
| 201841_s_at | HSPB1 | NM_001540.2 | 0,0036 | -0,018 | 0,0144 |
| 207857_at | LILRA2 | NM_006866.1 | 0,002 | -0,0101 | 0,0081 |

FIG. 25

Table 17A – Up-Regulated Genes from Table 14

| uniqid | Gene Symbol | Gene ID | ALL score | FEB score | Centroid distance |
|---|---|---|---|---|---|
| 207857_at | LILRA2 | NM_006866.1 | 0,002 | -0,0101 | 0,0081 |
| 201841_s_at | HSPB1 | NM_001540.2 | 0,0036 | -0,018 | 0,0144 |
| 207697_x_at | LILRB2 | NM_005874.1 | 0,0087 | -0,0437 | 0,035 |
| 219654_at | PTPLA | NM_014241.1 | 0,0096 | -0,048 | 0,0384 |
| 212124_at | ZMIZ1 | AF070622.1 | 0,0103 | -0,0513 | 0,041 |
| 212013_at | PXDN | D86983.1 | 0,0112 | -0,0562 | 0,045 |
| 213095_x_at | AIF1 | AF299327.1 | 0,0178 | -0,0892 | 0,0714 |
| 202870_s_at | CDC20 | NM_004295.1 | 0,0255 | -0,1275 | 0,102 |
| 208808_s_at | HMGB2 | BC000903.1 | 0,0323 | -0,1615 | 0,1292 |
| 212606_at | WDFY3 | AL536319 | 0,0362 | -0,1812 | 0,145 |
| 219271_at | GALNT14 | NM_024572.1 | 0,0413 | -0,2066 | 0,1653 |
| 201890_at | RRM2 | BE966236 | 0,0419 | -0,2094 | 0,1675 |
| 220570_at | RETN | NM_020415.2 | 0,0421 | -0,2103 | 0,1682 |
| 208893_s_at | DUSP6 | BC005047.1 | 0,0652 | -0,3259 | 0,2607 |
| 222303_at | --- | AV700891 | 0,0855 | -0,4275 | 0,342 |
| 221349_at | VPREB1 | NM_007128.1 | 0,0922 | -0,4608 | 0,3686 |
| 207030_s_at | CSRP2 | NM_001321.1 | 0,0952 | -0,4762 | 0,381 |
| 220085_at | HELLS | NM_018063.1 | 0,0987 | -0,4933 | 0,3946 |
| 218051_s_at | NT5DC2 | NM_022908.1 | 0,1042 | -0,5208 | 0,4166 |
| 212070_at | GPR56 | AL554008 | 0,1083 | -0,5416 | 0,4333 |
| 203821_at | HBEGF | NM_001945.1 | 0,1292 | -0,6462 | 0,517 |
| 202252_at | RAB13 | NM_002870.1 | 0,1295 | -0,6477 | 0,5182 |
| 213008_at | FANCI | BG403615 | 0,1421 | -0,7106 | 0,5685 |
| 204083_s_at | TPM2 | NM_003289.1 | 0,1532 | -0,7661 | 0,6129 |
| 203373_at | SOCS2 | NM_003877.1 | 0,1634 | -0,817 | 0,6536 |
| 211052_s_at | TBCD | BC006364.1 | 0,1653 | -0,8266 | 0,6613 |
| 219686_at | STK32B | NM_018401.1 | 0,3039 | -1,5195 | 1,2156 |

FIG. 26

Table 17B – Down- Regulated Genes from Table 14

| uniqid | Gene Symbol | Gene ID | ALL score | FEB score | Centroid distance |
|---|---|---|---|---|---|
| 214192_at | NUP88 | Y08613.1 | -0,1487 | 0,7437 | 0,595 |
| 203865_s_at | ADARB1 | NM_015833.1 | -0,1049 | 0,5244 | 0,4195 |
| 206126_at | BLR1 | NM_001716.1 | -0,0842 | 0,4212 | 0,337 |
| 210356_x_at | MS4A1 | BC002807.1 | -0,0813 | 0,4066 | 0,3253 |
| 217418_x_at | MS4A1 | X12530.1 | -0,073 | 0,3652 | 0,2922 |
| 216984_x_at | CKAP2 | D84143.1 | -0,0472 | 0,2358 | 0,1886 |
| 204118_at | CD48 | NM_001778.1 | -0,0394 | 0,1971 | 0,1577 |
| 210448_s_at | P2RX5 | U49396.1 | -0,0336 | 0,1678 | 0,1342 |
| 202625_at | LYN | AI356412 | -0,0319 | 0,1594 | 0,1275 |
| 219452_at | DPEP2 | NM_022355.1 | -0,0313 | 0,1567 | 0,1254 |
| 208536_s_at | BCL2L11 | NM_006538.1 | -0,0213 | 0,1064 | 0,0851 |
| 212577_at | SMCHD1 | AA868754 | -0,0184 | 0,092 | 0,0736 |
| 217875_s_at | TMEPAI | NM_020182.1 | -0,0143 | 0,0714 | 0,0571 |
| 211010_s_at | NCR3 | AF031138.1 | -0,0134 | 0,067 | 0,0536 |
| 205997_at | ADAM28 | NM_021778.1 | -0,0071 | 0,0355 | 0,0284 |

METHODS FOR DIAGNOSIS OF COMMON ACUTE LYMPHOBLASTIC LEUKEMIA BY DETERMINING THE LEVEL OF GENE EXPRESSION

This application corresponds to the national phase of International Application No. PCT/EP07/007297, filed Aug. 17, 2007, which, in turn, claims priority to European Patent Application No. 06.017264.0, filed Aug. 18, 2006, the contents of both of which are incorporated by reference herein in their entirety.

The present invention refers to a method and test kits for diagnosing pediatric common acute leukemia by distinguishing between normal and common acute lymphoblastic leukemic (cALL) cells, wherein the method comprises the step of determining the gene expression of specific genes (markers) referring to this disease and the step of determining whether these genes are up-regulated or down-regulated.

Acute lymphoblastic leukemia (ALL) is the most frequent leukemia in childhood. Common ALL (cALL) is the most prevailing subtype of ALL (Pui et al., N Engl J. Med. 1998; 339: 605-615). Clinical diagnosis of cALL still relies widely on morphology, although genetic abnormalities resulting from chromosomal translocations are used for diagnostic purposes. However, only in 60% of children with ALL, genetic abnormalities are detected with present technologies (Mrozek et al, Blood Rev 2004; 18(2):115-36). DNA microarray analysis has been utilized to better characterize genetic events underlying leukemogenesis.

An object of the present invention is to provide a rapid and simple assay for molecular identification of cALL cells for all patients. ALL of childhood is curable, but severe late effects are frequently reported, including brain tumors, cognitive deficits, osteonecrosis and infertility (see for example Neglia et al., N Engl J Med 1991; 325(19):1330-6; or Mattano et al., J Clin Oncol 2000; 18(18):3262-72). The knowledge of characteristic gene expression profiles as provided by the present invention will furthermore help to develop therapies appropriate for certain subgroups with dismal prognosis; e.g. glucocorticoid poor responders.

Previous studies on functional genomics so far only analyzed expression differences between defined subgroups of leukemia, e.g. ALL and acute myeloid leukemia (AML) or subgroups within ALL itself (Golub et al., Science 1999; 286(5439):531-7; Armstrong et al., Nat Genet 2001; 30(1): 41-7; Yeoh et al., Cancer Cell 2002; 1(3):133-43; Ross et al., Blood. 2004; 104(12):3679-87. Fine et al., Blood 2004; 103 (3):1043-1049).

One problem addressed by the present invention is to perform a more comprehensive analysis of the malignant phenotype of cALL. In order to learn more about the development of cALL at the transcriptome level and to investigate the malignant phenotype, the gene expression profiles of leukemia cells were compared with normal control cells of similar differentiation stage. Utilizing high-density DNA microarrays the differential expression of pediatric cALL blasts with sorted normal early pre B cells derived from umbilical cord blood of healthy, termed newborns was analyzed. Comparison of disease versus normal gene expression profiles identified differentially expressed genes, which have not been described previously and which can be used to diagnose cALL in patients by analyzing samples with the method according to the present invention.

The analysis of the malignant phenotype of cALL was undertaken by comparison of cALL cells to a putative normal control. Based on the developmental stage of pediatric cALL in B-lymphopoiesis comprehensively characterized by concordant expression of CD10 and CD19, CD10+CD19+ cALL cells were compared to normal fetal early pre B (FEB) cells expressing CD10 and CD19, obtained from cord blood of healthy newborns by immuno-magnetic cell sorting.

Unsupervised agglomerative hierarchical cluster analysis clearly supported the close relationship in gene expression of normal fetal early pre B cells to cALL by clustering fetal early pre B cells as an own group but tightly connected within cALL samples. Furthermore the basic pattern of gene expression in the data set was retrieved by unsupervised principal component analysis (PCA) and clearly indicated that the gene profile of both groups of samples was distinct enough to identify differentially expressed genes based on the probe selection.

The data set was then analyzed for differentially expressed genes by significance analysis of microarrays (SAM) with a delta value of 0.5 resulting in a false discovery rate of 6.3%, and a fold change for differentially expressed genes between cALL and FEB of $\geq 2$ (up-regulated genes) and $\leq 0.5$ (down-regulated genes) almost 2400 genes qualified for these criteria (Examples 1-3).

Reducing the numbers further to the most significant genes based on present and absent calls (requiring up-regulated genes to be expressed in more than 8 of 25 cALL probes and down regulated genes to be expressed in more than 5 of 6 FEB probes), still more than 1300 genes describe a cALL signature that provides a comprehensive view of the malignant phenotype. Gene ontology (GO) based annotation analysis revealed that for immune response related genes, the majority of them were down-regulated, whereas genes that play a role in apoptosis or cell cycle and proliferation were mostly up-regulated.

As mentioned above, surface antigen expression of CD19 and CD10 correlates with early pre-B cells stage of B lymphocyte differentiation. Further detection of CD20+/−, CD22+, CD24+/−, CD34+/−, CD79a+, DNTT+/−, HLA-DR+ and cytoplasmatic IgM+ in flow cytometry of leukemic blasts is utilized in diagnosis of cALL. RNA expression profiles confirmed this pattern. Immunophenotyping data in pediatric cALL patients' verify low or absent expression of CD45 and an increased resp. high expression of CD10, DNTT, and CD24 (Ratei et al., Ann Hematol 1998; 77(3): 107-14; and Inaba et al., Eur J Haematol 2000; 64(1):66-7).

When we compared our differentially expressed genes to other publications (Fine et al., Blood 2004; 103(3):1043-1049; Ross et al., 2004; 104(12):3679-87) more than 1500 of 2397 genes were not represented in previous analyses. Thus our cALL signature is only minimally represented in those other pediatric cALL gene chip studies. Significant genes previously not identified in cALL are listed in Table 1. Most significant genes of Table 1 based on even harder statistic criteria (stronger T-statistic value) are listed in Table 2 and 3.

Class prediction analysis also indicated that a number of genes within our data set are even more preferred because of their high predictive value for the malignant phenotype. To accurately determine the malignant phenotype at least 14 genes are required. Determination of the phenotype with 40 different genes results in accuracy $\geq 99.9\%$ based on a threshold value for the training error of 3.5, thirty-two of which have not been correlated with cALL before (Table 4). These genes have been identified with the help of the PAM (prediction analysis of shrunken centroids of gene expression software package) (PAM; Tibshirani R, Hastie T, Narasimhan B, Chu G. Diagnosis of multiple cancer types by shrunken centroids of gene expression. Proc Natl Acad Sci USA. 2002 May 14; 99(10):6567-72).

A kinase STK32B in addition to DNTT had the highest predictive value for the malignant phenotype and was previously not found to be associated with cALL. Moreover, SPRY2 found to be up-regulated in the present study in cALL but also in two additional T-ALL and pre B-ALL samples (FIG. 4B) in RT-PCR was shown to attenuate EGF (epidermal growth factor)-receptor ubiquitylation and endocytosis and thereby enhancing Ras/ERK mediated signaling (Wong et al., Embo J 2002; 21(18):4796-808) raising the possibility that its over-expression in cALL may enhance receptor tyrosine kinase signalling.

One gene (DTR) suggested to be involved in evasion of tumor cells from chemotherapeutic agent-induced apoptosis, was found to be 26-fold up-regulated in cALL. Similar results were obtained for Sprouty2 (SPRY2), encoding a protein with a carboxy-terminal cysteine-rich domain essential for the inhibitory activity on receptor tyrosine kinase activity and a leukocyte immunoglobulin-like receptor family protein (LILRA2), which belongs to a family of immunoreceptors expressed predominantly on monocytes and B cells and at lower levels on dendritic cells and natural killer (NK) cells. SPRY2 was found 10-fold up-regulated in leukemia samples with a calculated q-value (giving the lowest False Discovery Rate at which the gene is called significant (J. D. Storey. A direct approach to false discovery rates. J Roy Stat Soc., Ser.B, 64:479-498)) of 0.16% and LILRA2 had a FC=5.8. For all four genes up-regulation was confirmed in independent cALL probes by RT-PCR.

Similarly, genes differentially regulated in cALL are not influenced by viral infection as EBV transformed B cells (LCLs) show no dysregulation of investigated genes STK32B, LILRA2 and CD37 (FIG. 5).

With respect to the present invention, further examples (Examples 5-6) were carried out using even higher purified B cells. The purification of the B cells is described in Example 5. Using the same method as described in Examples 1-3, the data set was then analyzed for differentially expressed genes by significance analysis of microarrays (SAM) with a false discovery rate of 10.2%, and a fold change for differentially expressed genes between cALL and FEB of $\geq 2$ (up-regulated genes) and $\leq 0.5$ (down-regulated genes) almost 1500 genes qualified for these criteria.

Reducing the numbers further to the most significant genes based on present and absent calls (requiring up-regulated genes to be expressed in more than 8 of 25 cALL probes and down regulated genes to be expressed in 3 of 3 batches of FEB probes), still more than 1000 genes describe a cALL signature that provides a comprehensive view of the malignant phenotype. 367 genes of these were up-regulated with a fold change $\geq 3$, whereas 338 were downregulated. Gene ontology (GO) based annotation analysis revealed that for immune response related genes, the majority of them were down-regulated, whereas genes that play a role in apoptosis or cell cycle and proliferation were mostly up-regulated.

The genes which are suitable for diagnosing cALL and which have been identified in Examples 1-3 are summarized in Tables 1-4. Table 1 comprises all suitable genes from Examples 1-3. Preferred genes which are most significantly up-regulated in cells of patients suffering from that disease are listed in Table 2. Preferred genes which are most significantly down-regulated in cells from patients suffering from this disease are listed in Table 3. Even more preferred genes with the most predictive values are listed in Table 4.

The genes which are suitable for diagnosing cALL and which have been identified in Examples 5 and 6 are summarized in Tables 5-16. Table 5 comprises all suitable genes from Examples 5-6. The genes in Table 6 represent genes common to both examples (1-3 and 5-6). The genes in Table 7 represent those genes, which have been found in addition to the genes as identified in Examples 1-3. The genes in Tables 8-10 represent even more significant up-regulated genes of Table 5 based on even harder statistic criteria (lower false discovery rate), wherein the genes in Table 8 represent the most significant up-regulated genes (lowest false discovery rate), the genes in Table 9 represent the most significant genes common in both examples (1-3 and 5-6) and the genes in Table 10 represent the most significant up-regulated genes identified in addition to those in examples 1-3. The genes in Tables 11-13 represent even more significant down-regulated genes of Table 5 based on even harder statistic criteria (lower false discovery rate), wherein the genes in Table 11 represent the most significant down-regulated genes (lowest false discovery rate), the genes in Table 12 represent the most significant genes common in both examples (1-3 and 5-6) and the genes in Table 13 represent the most significant down-regulated genes identified in addition to those in examples 1-3. The genes in Table 14 represent even more preferred genes with the most predictive values identified in examples 5 and 6. The genes in Table 15 represent the most predictive genes of Table 14 common in examples 1-3 and 5-6. The genes in Table 16 represent newly identified most predictive genes in examples 5-6.

The present invention therefore provides a new method for the diagnosis of pediatric common acute lymphoblastic leukemic (cALL) cells. This method is based on the identification of genes, which are related to this disease. The gene expression of the genes related to pediatric common acute lymphoblastic leukemia according to the present invention is either up-regulated or down-regulated in cells from patients suffering from this disease compared to healthy cells. By determining the level of gene expression through measuring of the amounts of DNA, RNA or gene expression products in cells from a human sample and comparing the gene expression from the sample cells with the gene expression in healthy cells, it is possible to identify patients suffering from this disease.

The present invention therefore provides a method for diagnosing pediatric common acute lymphoblastic leukemia (cALL) by distinguishing between normal and common acute lymphoblastic leukemic (cALL) cells, wherein the method comprises the steps of (a) determining the gene expression of genes referring to the pediatric common acute lymphoblastic leukemia in cells from a human test sample and a control sample derived from a healthy individual, wherein the gene expression of at least 14, further preferred of at least 20, even further preferred of at least 30, further preferred of at least 40, further preferred of at least 50, and most preferred of at least 80 genes selected from Tables 1-4 or the gene expression of at least 14, further preferred of at least 20, even further preferred of at least 30, further preferred of at least 40, further preferred of at least 50, and most preferred of at least 80 genes selected from Tables 5-16 is determined, and (b) determining whether the genes are up-regulated or down-regulated in the test sample compared to the control sample.

It is understood in the context of the present invention that one specific gene is only selected once, i.e. one specific gene cannot be selected from different tables.

In a preferred embodiment, the method for diagnosing pediatric common acute lymphoblastic leukemia (cALL) by distinguishing between normal and common acute lymphoblastic leukemic (cALL) cells comprises the steps of
(a) determining the gene expression of genes referring to the pediatric common acute lymphoblastic leukemia in cells from a human test sample and a control sample derived from a healthy individual, wherein the gene expression of at least 14, further preferred of at least 20, even further preferred of at least 30, further preferred of at least 40, further preferred of at least 45 genes selected from Tables 1-16, further preferred selected from Tables 5-16, further preferred selected from Tables 6-16, further preferred selected from Tables 8-16, further preferred selected from Tables 14-16, further preferred selected from Table 5, even further preferred selected from Table 7, is determined, and
(b) determining whether the genes are up-regulated or down-regulated in the test sample compared to the control sample.

In an especially preferred embodiment, the method comprises determining the gene expression of at least 14, further preferred of at least 20, even further preferred of at least 30, further preferred of all genes from Table 14. Even further preferred is to determine all genes from Table 14.

In another preferred embodiment of the invention, the step of determining the gene expression comprises determining the gene expression of at least 7, further preferred of at least 10, further preferred of at least 14, further preferred of at least 20, even further preferred of at least 30, further preferred of at least 40, further preferred of at least 50, and most preferred of at least 80 up-regulated genes selected from Table 1 or at least 7, further preferred of at least 10, further preferred of at least 14, further preferred of at least 20, even further preferred of at least 30, further preferred of at least 40, further preferred of at least 50, and most preferred of at least 80 up-regulated genes selected from Table 5, and of at least 7, further preferred of at least 10, further preferred of at least 14, further preferred of at least 20, even further preferred of at least 30, further preferred of at least 40, further preferred of at least 50, and most preferred of at least 80 down-regulated genes selected from Table 1 or of at least 7, further preferred of at least 10, further preferred of at least 14, further preferred of at least 20, even further preferred of at least 30, further preferred of at least 40, further preferred of at least 50, and most preferred of at least 80 down-regulated genes selected from Table 5, provided that each gene can be selected once only, is determined.

It is further understood in the context of the present invention that a selection of up-regulated genes from Tables 1-4 is preferably combined with selecting the down-regulated genes also from Tables 1-4. A selection of up-regulated genes from Tables 5-16 is then preferably combined with selecting the down-regulated genes from Tables 5-16.

In a further preferred embodiment, the gene expression of at least 10, further preferred of at least 14, further preferred of at least 20, even further preferred of at least 30 up-regulated genes independently selected from Table 2 or at least 10, further preferred of at least 14, further preferred of at least 20, even further preferred of at least 30 up-regulated genes independently selected from Table 8 and at least 10, further preferred of at least 14, further preferred of at least 20, even further preferred of at least 30 down-regulated genes independently selected from Table 3 or at least 10, further preferred of at least 14, further preferred of at least 20, even further preferred of at least 30 down-regulated genes independently selected from Table 11, provided that each gene can be selected once only, is determined.

In another preferred embodiment, the gene expression of at least 10 up-regulated genes independently selected from Table 1, Table 2 and Table 4 or at least 10 up-regulated genes independently selected from Table 5, Table 8 and Table 14, and at least 10 down-regulated genes independently selected from Table 1, Table 3 and Table 4 or at least 10 down-regulated genes independently selected from Table 5, Table 11 and Table 14, provided that each gene can be selected once only, is determined.

In a further preferred embodiment, at least one gene to be determined is selected from Table 4 or at least one gene to be determined is selected from Table 14.

It is additionally preferred that in all embodiments described above, at least one gene, further preferred at least 7 genes, further preferred at least 14 genes are selected from Table 4 and/or from Table 14, further preferred from Table 14.

The present invention furthermore relates to a kit for distinguishing between normal and pediatric common acute lymphoblastic leukemic (cALL) cells by quantitative determination of mRNA, which comprises a solid support on which at least 14, further preferred at least 20, even further preferred at least 30, further preferred at least 40, further preferred at least 50, and most preferred at least 80 different isolated polynucleotides are immobilized, wherein said isolated polynucleotides have the sequence or a part of the sequence
(i) of the mRNA corresponding to one of the genes selected from Table 1, further preferred selected from Table 2 or Table 3,
(ii) of the mRNA corresponding to one of the genes selected from Table 5, further preferred selected from Table 8 or Table 11,
(iii) complementary to any of the sequences under (i) or (ii), or
(iv) which is an allelic variant of any of the sequences under (i), (ii) or (iii),
and wherein the total amount of different genes on the solid support is additionally preferably less than 33000 genes.

In a preferred embodiment of the kit, the solid support comprises at least 20 different isolated polynucleotides immobilized on said solid support, and said 20 different isolated polynucleotides have sequences complementary to the sequences of genes independently selected from Table 1 and/or Table 5, preferably from Table 2 and Table 3 and/or Table 8 and Table 11.

In another embodiment of the present invention, the kit comprises a solid support with at least 40 different isolated polynucleotides immobilized on said solid support, and said 40 different isolated polynucleotides have sequences complementary to the sequences of the corresponding genes in Tables 1 and/or Table 5, further preferred Table 5. It is even more preferred that the kit comprises at least 30 different isolated polynucleotides immobilized on said solid support, and said 30 different isolated polynucleotides have sequences complementary to the sequences of the corresponding genes in Table 1 and/or Table 5, further preferred Table 5.

The present invention also relates to the use of a compound for the manufacture of a medicament for the treatment of pediatric common acute lymphoblastic leukemic (cALL), wherein the compound increases or decreases the expression of at 14 of the genes independently selected from Table 2, Table 3, Table 8 or Table 11.

In one embodiment of the present invention the method for diagnosing pediatric common acute lymphoblastic leukemia (cALL) by distinguishing between normal and common acute lymphoblastic leukemic (cALL) cells comprises the steps of
(a) determining the gene expression of genes referring to the pediatric common acute lymphoblastic leukemia in cells from a human test sample and a control sample derived from a healthy individual, wherein the gene expression of at least one gene selected from Table 1, Table 2, Table 3 or Table 4 is determined, further preferred from Table 2, Table 3 or Table 4, even further preferred from Table 4, and (b) determining whether the genes are up-regulated or down-regulated in the test sample compared to the control sample.

In a preferred embodiment of the invention, the gene expression is determined by measuring the mRNAs or gene expression products corresponding to the genes referring to the pediatric common acute lymphoblastic leukemia in a quantitative manner.

In another embodiment, the step of determining the gene expression comprises determining the mRNAs or gene expression products corresponding to at least 7, further preferred at least 10, up-regulated genes selected from Table 1, Table 2 and Table 4, further preferred from Table 2 and Table 4, and at least 7, further preferred at least 10, down-regulated genes selected from Table 1, Table 3 and Table 4, further preferred from Table 3 and Table 4.

It is preferred that the gene expression of at least 10, further preferred at least 15, up-regulated genes from Table 1, Table 2 and Table 4, further preferred from Table 2 and Table 4, and at least 10, further preferred at least 15, down-regulated genes selected from Table 1, Table 3 and Table 4, further preferred from Table 3 and Table 4 is determined.

It is even more preferred that the gene expression of at least 7 up-regulated genes from Table 4 and at least 7 down-regulated genes selected from Table 4 is determined.

It is especially preferred to determine the gene expression of all genes from Table 4.

It is preferred that the test sample and the control sample comprise purified CD10+CD19+B-cells.

In another preferred embodiment of the invention, the step of determining whether the genes are up-regulated or down-regulated in the test sample compared to the control sample comprises to determine the fold change values of the genes in the test sample.

It is preferred that a gene is defined as up-regulated if its fold change value is at least 2 and down-regulated if its fold change value is smaller than or equal to 0.5.

It is further preferred that a gene is defined as up-regulated if its fold change value is at least 3 and down-regulated if its fold change value is smaller or equal to 0.33.

It is further preferred that the median false discovery rate (FDR) of the method for determining and analyzing the gene expression is smaller than 10%, more preferred smaller than 7% and even more preferred smaller than 4%.

In a further preferred embodiment of the invention, determining the gene expression comprises to determine the expression of STK32B.

In another preferred embodiment of the invention, determining the gene expression comprises to determine the expression of at least one gene selected from Table 4.

Furthermore it is preferred that the step of determining the gene expression comprises the use of hybridization technology and/or polymerase chain reactions (PCR).

In one embodiment of the present invention the PCR method comprises:

a) contacting the mixture of mRNAs or cDNAs from said sample with amplification reagents comprising pairs of primers, wherein said pairs of primers substantially correspond or are substantially complementary to the gene sequences of the genes to be determined.

b) carrying out an amplification reaction c) measuring the generation of amplification products; and d) determining the quantity of mRNA in said sample from the results obtained in step c).

It is preferred that said amplification reaction is a real-time-PCR (polymerase chain reaction).

In another embodiment, the hybridization technology comprises measuring the gene expression by hybridizing the mRNAs or cDNAs of the samples with complementary nucleotide probes immobilized on a solid support.

The present invention furthermore relates to a method for identifying compounds which modulate the expression of any of the genes referring to the pediatric common acute lymphoblastic leukemia as defined in the preceeding embodiments, comprising:

(a) contacting a candidate compound with leukemic B-cells which express said genes and (b) determining the effect of said candidate compound on the expression of said genes.

In a preferred embodiment of the invention the candidate compound is selected from the group consisting of si-RNA, anti-sense-RNA or other interfering nucleic acids, antibodies, aptamers and small molecules.

It is preferred that the step of determining the effect of a compound on the gene expression according to this method, comprises comparing said expression with the expression of said genes in purified CD10+CD19+B-cells which were not contacted with the candidate compound.

The present invention also relates to a kit for distinguishing between normal and pediatric common acute lymphoblastic leukemic (cALL) cells by quantitative determination of mRNA according to the method as described above.

In a preferred embodiment, the kit comprises a solid support on which at least one isolated polynucleotide is immobilized, wherein said isolated polynucleotide has the sequence or a part of the sequence (i) of the mRNA corresponding to one of the genes selected from Table 2 or Table 3, preferably from Table 4, (ii) complementary to any of the sequences under (i)

(iii) which is an allelic variant of any of the sequences under (i) or (ii).

In another embodiment of the present invention, the kit comprises a solid support with at least 20, further preferred at least 40, different isolated polynucleotides immobilized on said solid support, and said 20, further preferred at least 40, different isolated polynucleotides have sequences complementary to the sequences of the corresponding genes in Table 2 and Table 3. It is even more preferred that the kit comprises at least 14, further preferred at least 30, different isolated polynucleotides immobilized on said solid support, and said 14, further preferred at least 30, different isolated polynucleotides have sequences complementary to the sequences of the corresponding genes in Table 4.

The present invention further relates to the use of a compound for the manufacture of a medicament for the treatment of pediatric common acute lymphoblastic leukemic (cALL), wherein the compound increases or decreases the expression of at least one of the genes selected from Table 2 or Table 3, more preferably selected from Table 4.

The present invention also relates to the use of a compound for the manufacture of a medicament for the treatment of pediatric common acute lymphoblastic leukemic (cALL), wherein the compound increases or decreases the expression of at least one of the genes selected from Table 1 or Table 5, more preferably selected from Table 2, Table 3, Table 8 or Table 11, even more preferred selected from Table 8 or Table 11.

Therefore the present invention refers to a method and means for diagnosis of the pediatric common acute lymphoblastic leukemia (cALL). In order to determine whether a patient is suffering from this disease or not, a biological sample has to be taken. This biological sample can be any sample derived from or containing body liquid or tissue material such as e.g. samples of blood or bone marrow drawn from patients at diagnosis. It is preferred that the sample comprises B-cells.

Usually, the sample has been processed to be in a condition suitable for the method of determining the gene expression. The processing may include dilution, concentration, homogenization, extraction, precipitation, fixation, washing and/or permeabilization, etc. The processing may also include reverse transcription according to methods well known in the field.

The method for diagnosing pediatric common acute lymphoblastic leukemia comprises the step of determining the gene expression of genes referring to the pediatric common acute lymphoblastic leukemia in the cells from the human sample. The phrase "determining the gene expression" as used herein preferably means "determining the expression level". The expression or expression level correlates with the amount of polynucleotide or expression product thereof in the sample.

The gene expression can be determined by qualitatively or quantitatively measuring the function, protein level, mRNA level or the gene copy number referring to these genes. It is preferred to determine the gene expression quantitatively. The mRNA level determination can furthermore comprise to measure the amount of the corresponding cDNA, whereas the synthesis of cDNA can be performed applying common techniques. It is preferred to use cDNA in the method according to the present invention. The gene expression products or the total cellular RNA are isolated from these samples by techniques well known in the field (compare example 2 and 4). For example the single-step guanidinium-thiocyanate-phenol-chloroform method described in Chomczynski and Sacchi (Anal. Biochem. 1987; 162:156-159) can be used. The LiCl/urea method described in Auffray and Rougeon (Eur. J. Biochem. 1980; 107:303) can also be used.

The method according to the present invention comprises the quantitative determination of the gene expression of the above defined up-regulated and down-regulated genes. Additionally, it is preferred that the gene expression of at least 14, further preferred of at least 20, genes from Tables 1, 2, 3 and 4 which can be up-regulated or down-regulated in cells referring to cALL is determined in every sample. It is further preferred to determine the expression of at least seven, further preferred of at least 10, of the genes from the group of up-regulated genes from Tables 1-4 or Tables 5-14 and of at least seven, further preferred of at least 10, further preferred of at least 20, gene from the group of the down-regulated genes from Tables 1-4 or Tables 5-14. It is especially preferred to determine the expression of at least ten, further preferred of at least 15, genes from the group of up-regulated genes from Tables 1-4 or Tables 5-14 and of at least ten, further preferred of at least 15, genes from the group of the down-regulated genes from Tables 1-4 or Tables 5-14. In a preferred embodiment of the invention other known gene markers for cAll or even other diseases can be determined in combination with the gene markers of the present invention.

In another preferred embodiment, the expression of at least seven, further preferred of at least 10, of the genes from the group of up-regulated genes from Table 6 and at least seven, further preferred of at least 10, further preferred of at least 20, genes from the group of the down-regulated genes from Table 5, further preferred from Table 6.

The quantitative determination of the expression of the above described genes can be performed by measuring the amount of RNA, mRNA, genomic DNA (obtained by cloning or produced synthetically) or cDNA corresponding to said genes. The DNA may be double- or single-stranded. Single-stranded DNA may be the coding strand, also known as the sense strand, or it may be the noncoding strand, also referred to as the antisense strand. The quantitative determination of the gene expression can be performed by using the hybridization technology or a polymerase chain reaction or a mixture or a combination of these techniques, but is not limited to these methods. Some of these methods are exemplary described in more detail below. Furthermore the gene expression can be determined by measuring the amount of gene expression products (polypeptides) referring to these genes by common methods.

Assaying the gene copy number of the genes of the present invention can be performed by any known technique such as, for example, by visualizing extrachromosomal double minutes (dmin) or integrated homogeneously staining regions (hsrs) (Gebhart et al., Breast Cancer Res. Treat. 1986; 8:125; or Dutrillaux et al., Cancer Genet. Cytogenet. 1990; 49:203). Other techniques such as comparative genomic hybridization (CGH) single nucleotide polymorphism (SNP) and a strategy based on chromosome microdisection and fluorescence in situ hybridization can also be used to search for regions of increased DNA copy number in tumor cells (Guan et al., Nature Genet. 1994; 8:155).

The hybridization technology comprises contacting RNA, (such as mRNA) or DNA (such as cDNA) with a nucleotide probe. It is preferred that the nucleotide probes are immobilized on a solid support. The nucleotide sequence to be determined (target) hybridizes to the nucleotide probe, whereas a double-strand is formed. In order to measure the amount of hybridization products, common methods can be applied, such as spectroscopic techniques using fluorescent dyes.

The polynucleotide probes of the present invention, which can be freely dissolved or can be immobilized have a sequence according to the genes as described above or are complementary to these genes. A person skilled in the art is well aware that also characteristic fragments of these sequences are suitable for the detection of the targets. Furthermore probes may have a sequence which is a variant of the sequences of the genes of the present invention. The variant may be a sequence having one or more additions, substitutions, and/or deletions of one or more nucleotides such as an allelic variant or single nucleotide polymorphism of the sequences of the marker genes. It is preferred that the probes are at least 80% identical to the target gene sequences, whereas the probe can also have the complementary sequence. Further preferred is that the probes are at least 85%, more preferred 90% and even more preferred 97% identical or complementary to the sequences as indicated in Table 2-4 or Tables 5-14.

The fluorescent dyes to be used for the spectroscopical quantification can be directly attached to the nucleotide probe, but can also be present in solution without any covalent-bond to the nucleotide. The use of oligonucleotide probes comprising at least one intercalator pseudonucleotide is disclosed in US 2006/0014144 and is incorporated by reference. The intercalation of the fluorescent dye into the double-stranded hybrid results in specific fluorescent properties, which can be measured by using common methods. Suitable assay formats for detecting hybrids formed between probes and target nucleic acid sequences in a sample are known in the art and include the immobilized target assay formats, such as the dot-blot format, and immobilized probe assay formats, such as the reverse dot-blot assay. Dot blot and reverse dot blot assay formats are described in U.S. Pat. Nos. 5,310,893; 5,451,512; and 5,468,613. The northern blot method among others is e.g. disclosed in U.S. Pat. No. 5,981,218 and furthermore in Harada et. al (Cell 1990; 63:303-312), whereas all methods therein are incorporated by reference.

However, any known standard hybridization technique can be used according to the invention. One preferred example, using immobilized nucleotide probes is the microarray technology. The microarray technology, which is also known as DNA chip technology, gene chip technology and solid-phase nucleic acid array technology, is well known to the skilled person and is based on, but not limited to, obtaining an array of identified nucleic acid probes on a fixed support, labelling target molecules with reporter-molecules (e.g., radioactive, chemiluminescent or fluorescent tags), hybridizing target nucleic acids to the probes, and evaluating target-probe hybridization. A probe with a nucleic acid sequence that perfectly matches the target sequence will, in general, result in detection of a stronger reporter-molecule signal than with probes with less perfect matches. Many components and techniques utilized in nucleic acid microarray technology are presented in "*The Chipping Forecast*", Nature Genetics, volume 21, January 1999.

According to the present invention, microarray supports may include but are not limited to glass, silica, aluminosilicates, borosilicates, plastics, metal oxide, nitrocellulose or nylon. The use of a glass support is preferred. According to the invention, probes are selected from the group of polynucleotides including, but not limited to DNA, genomic DNA, cDNA and oligonucleotides; and maybe natural or synthetic. Oligonucleotide probes preferably are 20-25-mer oligonucleotides and DNA/cDNA probes preferably are 500-5000 bases in length, although other lengths may be used. Appropriate probe length may be determined by the skilled person by known procedures. Probes may be purified to remove contaminants using standard methods known to those of ordinary skill in the art such as gel filtration or precipitation. Accordingly, the polynucleotide immobilized to the solid support is preferably an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

In one embodiment, probes are synthesized directly on the support in a predetermined grid pattern using methods such as light-directed chemical syntheses, photochemical deprotection or delivery of nucleotide precursors to the support and subsequent probe production. In embodiments of the invention one or more control polynucleotides are attached to the support. Control polynucleotides may include but are not limited to cDNA of genes such as housekeeping genes or fragments thereof.

The solid support comprises at least one polynucleotide immobilized on or attached to its surface, wherein said polynucleotide hybridizes with a polynucleotide as described supra, preferably under stringent conditions. Suitable hybridization conditions are for example described in the manufacturer's instructions of "DIG Easy HYB Granules" (Roche Diagnostics GmbH, Germany, Cat. No. 1796895). These instructions are incorporated herein by reference. The hybridization conditions described in the following protocol may be used:

1. Hybridizations are carried out using DIG Easy Hyb buffer (Roche Diagnostics, Cat. No. 1796895).
2. Ten microliters of hybridization solution with probe is placed on the microarray and a cover slip carefully applied.
3. The slide is replaced in a hybridization chamber and incubated for 16 hours incubation at 42° C.
4. The cover slips are removed in a container with 2×SSC+0.1% SDS and the microarrays are washed for 15 minutes in 2×SSC+0.1% SDS at 42° C. followed by a 5 minutes wash in 0.1×SSC+0.1% SDS at 25° C. followed by two short washes in 0.1×SSC and 0.01×SSC at 25° C., respectively.
5. The microarrays are dried by centrifugation and can be stored at 4° C.

The detection of the fluorescence of the samples can be performed by any techniques known in the art and can also be performed analog to the methods as described for the PCR below. The quantitative determination of the target sequences is also well known in the art.

In one embodiment, preferred probes are sets of ten or more of the nucleic acid molecules as defined. In a specific embodiment, at least twenty different isolated polynucleotides are immobilized on said solid support. Preferably said different isolated polynucleotides correspond or are complementary to genes in Table 2-4.

In another embodiment, at least ten or at least 15, further preferred at least 20, further preferred at least 30, or at least 40 different isolated polynucleotides corresponding to or being complementary to the up-regulated and down-regulated genes as specified above are immobilized on said solid support, whereas preferably the solid support can additionally contain polynucleotides which do not refer to the above specified genes. The nucleotide sequences of the genes are defined in Tables 2-4 and 8-16. Preferably, the solid support comprises at least 40, further preferred at least 60, further preferred at least 80, genes selected from Tables 1-16, further preferred selected from Tables 2-16, further preferred selected from Tables 8-16. It is additionally preferred that the number of different genes (genes from Tables 1-16 and any other genes) on the solid support is less than 33000, further preferred less than 30000, further preferred less than 25000, further preferred less than 22000, further preferred less than 20000, further preferred less than 17000, further preferred less than 15000, further preferred less than 13000, further preferred less than 10000, further preferred less than 8000, further preferred less than 5000, further preferred less than 4000, further preferred less than 3000, further preferred less than 2000, further preferred less than 1000, further preferred less than 500, further preferred less than 400, further preferred less than 300, further preferred less than 200.

In another embodiment, the method comprises utilizing an antibody directed against a polypeptide encoded by the genes described above. The antibody may be polyclonal or monoclonal, with monoclonal antibodies being preferred. The antibody is preferably immunospecific for anyone of the polypeptides encoded by the above genes. The antibodies can be used to detect a polypeptide by any standard immunoassay technique including a ELISA, flow cytometry, immunohistochemistry, immunoblotting, (western blotting), immunoprecipitation, BIACORE technology and the like, as will be appreciated by one of ordinary skill in the art.

Another possibility to perform the determination of the gene expression is the polymerase chain reaction (PCR). The PCR method can be used to amplify the above indicated RNA/mRNA or DNA/cDNA samples and allows to quantitatively back-calculate the quantity and the concentration of the amount of specific polynucleotide (target) in the sample. The PCR method is well known in the art and for example disclosed in WO 99/28500 or Sambrook et al. (Molecular Cloning—A Laboratory Manual, Cold Spring Harbor Laboratory, Cold Spring Harbor, N.Y. 1989) or Nucleic Acid Hybridization (Hames and Higgins eds., 1984) or Current Protocols in Human Genetics (Dracopoli et al., eds, 1984 with quarterly updates, John Wiley & Sons, Inc.), all of which are incorporated herein by reference.

The PCR method utilizes a pair of oligonucleotides (primers), each hybridizing to one strand of a double-stranded DNA/RNA target. The target corresponds to the specific DNA/RNA, which has to be determined in a quantitative manner. The primers flank the region that will be amplified. The PCR method comprises contacting the primers and target sequence or mixture of target sequences and optional polynucleotide probes and performing the amplification steps.

The primer will contain a "hybridizing region" exactly or substantially complementary or corresponding to a nucleotide sequence (target sequence) from one gene which is related to the common acute lymphoblastic leukemia. The amplification is carried out using the primer, whereas the primer extension is performed under sufficiently stringent hybridization conditions, which allow the selective amplification of specific target sequences. Preferably the primer is from 15 to 35 nucleotides in length. A primer can either consist entirely of the hybridizing region or can contain additional features which allow for detection, immobilization, or manipulation of the amplified product, but which do not alter the basic property of the primer (acting as a point of initiation of DNA synthesis).

The primers can furthermore comprise covalently-bound fluorescent dyes, which confer specific fluorescence properties to the hybrid consisting of the primer and the target-sequence. An example for this method is the LUX®-primer technique (GEN et al., J Virol Methods 2004; 22:57-61) utilizing specific fluorescent dyes, which change their fluorescence properties because of the structural changes occurring due to the formation of the double-stranded DNA/RNA.

But it is also possible to use fluorescent dyes which are not covalently-bound to the primer, but can interact with the double-stranded DNA/RNA to change the fluorescence properties. Fluorescent dyes which can be used are for example SYBR-green or Ethidiumbromid (U.S. Pat. No. 6,346,386 or Zipper et al., Nucl. Acid Res. 2004; 32:103).

If amplification products have to be determined by fluorescence and a mixture of target sequences is amplified at the same time in the same reaction mixture, the different targets have to be specifically and separately detected. This can be done by using primers comprising fluorescent dyes, whereas the different primers can be detected at different wavelength, due to different fluorescent properties. Different fluorescence properties can be achieved with different dyes or additional covalently attached dyes which alter the fluorescence properties by changing the electronic properties. But also any other method can be used to influence the fluorescence properties.

The detection of the fluorescence of the samples can be performed by any techniques known in the art. For example UV/Vis spectrophotometers can be used to determine the intensity of the signals at different wavelengths.

Another possibility is to use polynucleotide probes in addition to the pairs of primers. These probes contain a "hybridizing region" which is exactly or substantially complementary to the target sequence and specifically hybridizes to one amplified target sequence. Furthermore these probes comprise fluorescent dyes. Again the fluorescence properties of these probes are different and allow the detection of each target separately. This method has for example been reported by Wong et al (BioTechniques 2005; 39:75-85) and EP0678581. Also other techniques can be used such as: Taq Man, Molecular Beacon, ARMS, Scorpions, FRET (DE19755642 and Tyagi et al., Nat. Biotechnol. 2000; 18:1191-1196) etc. These methods are well known in the art and can be adapted and performed by a person skilled in the art. Of course, the PCR methods which can be used according to the present invention are not limited to these examples.

For the polynucleotide probes suitable for the PCR method the same applies as for the probes as specified for the hybridization technique above.

A person skilled in the field is able to synthesize suitable primers according to common techniques, based on the polynucleotide-sequences of the genes as identified above. It is understood that the primers can be suitable to amplify the complete corresponding or complementary nucleotide sequence of the marker genes or can be suitable to amplify only a part of this sequence, whereas the primers are selected to be suitable to specifically amplify and identify one marker gene. Accordingly pairs of primers have to be selected for every marker gene which has to be determined.

The hybridized primer acts as a substrate for a thermostable DNA polymerase (most commonly derived from *Thermus Aquaticus* and called Taq polymerase) that synthesizes a complementary strand via a sequential addition of Deoxyribonucleotides. The process includes repetitive cycles of three steps, denaturation of double-stranded DNA, annealing of the primers and extension of the DNA fragments, which are accomplished by cycle temperature changes in the reaction. The number of repetitive cycles varies usually from 25 to 50 in PCR tests used for diagnostic purposes. If the starting material is RNA/mRNA, a further step with a reverse transcriptase (RT) enzyme can be performed before amplification. This technique is then referred to as RT-PCR, which is e.g. described by Makino et al. (Technique 1990; 2:295-301) or WO 97/06256.

Quantitation of a sample containing an unknown number of target sequences typically is carried out with reference to a "standard curve" generated from a series of amplifications of samples containing the target sequence in a range of known amounts. The standard curve is used to calculate an input copy number from the signal generated during an amplification. Thus, the unknown target sequence copy number in the sample of interest is estimated using the standard curve by calculating the copy number that previously was determined to yield a signal equal to that observed. The concentration of the target sequence in the sample then is calculated from the input copy number and the sample size, which is determined prior to reaction.

Quantitative estimates can be sensitive to variability in either the input sample size or in the reaction efficiency. The effect of inter-reaction viability of the input sample size on the calculated target concentration can be eliminated by using a control gene. A control gene provides an independent measure of the amount of RNA in the sample. The calculated concentration of target mRNA is adjusted based on the independent measure of sample size.

It is especially preferred to use a real-time PCR, whereas the accumulation of the PCR products is monitored continuously during the PCR run. There are several instruments available for real-time PCR, in which the accumulation of the product is monitored by measuring the fluorescence in each cycle, and these methods can be used according to the invention. The measured fluorescence is plotted against the cycle number. The cycle number, in which the exponential amplification (threshold cycle CT) is first detected over background, has an inverse linear relationship to the amount of target in the initial reaction. Absolute quantitation of the amount of target in the initial sample can be accomplished by measuring its CT value and using the external standard curve to determine the target sequence. By using the real time PCR it is possible to determine quantitatively the amount of mRNA in a sample. If the concentration of a mRNA species in a sample is low, additional cycles are required in order to detect a signal compared to a higher concentration of the mRNA species.

The real-time PCR can also be combined with the microarray technique which allows to quantitatively and simultaneously determine a plurality of nucleic acids. This method is disclosed in US 2006/0088844 and incorporated by reference.

In a special embodiment, pairs of primers are selected, which are suitable to each amplify a specific nucleotide sequence which can be found in more than one marker gene, whereas in this case every pair of primers amplifies parts of the DNA/RNA sequences corresponding to more than one marker gene. In other words, during the gene expression determination more than one gene is subject to the same pair of primers and can be amplified by this primer pair. The amount of DNA/RNA measured for this subgroup of genes corresponds to the total amount of gene expression for this subgroup by addition of the single levels of gene expression of every member of the subgroup. This allows to compare this gene expression value of the subgroup with the control sample derived from a healthy individual. In this case it is not possible to give the gene expression value for the single members of this subgroup, but only the total value.

After the amount of polynucleotide referring to the genes according to the invention has been determined, a comparison has to be made with the values observed in healthy cells. Amplification-based quantitation methods using an internal standard are described in U.S. Pat. Nos. 5,219,727 and 5,476,774, incorporated herein by reference. In these methods the internal standard is added to the reaction in a known copy number and co-amplified along with the RNA/DNA target.

It is furthermore possible to use a probe-less method, referred to herein as a kinetic-PCR method, for measuring the increase in amplified nucleic acid by monitoring the increase in the total amount of double-stranded DNA in the reaction mixture. This method is described in Higucci et al, (Bio/Technology 1992; 10:413-417; Bio/Technology 1993; 11:1026-1030) and U.S. Pat. No. 5,994,056, EP 487,218 and EP 512,334, each incorporated herein by reference. The detection of double stranded target DNA can be performed by using fluorescent dyes as described above.

It is also possible to measure the level of gene expression by determining the amounts of gene expression products in the samples. For example antibody-based methods are useful for detecting the gene expression and include immunoassays, such as the enzyme linked immunosorbent assay (ELISA) and the radio immunoassay (RIA). For example, a monoclonal antibody can be used both as an immunoabsorbent and as an enzyme-labelled probe to detect and quantify the proteins, corresponding to the genes which are related to the common acute lymphoblastic leukemia. These methods can be performed according to standard procedures, whereas also any other method known in the art can be used to measure the amount of gene expression products in the samples. For example such an ELISA for detecting a tumor antigen is described in Iacobelli et al. (Breast cancer research and treatment 1988; 11:19-30).

For determining whether or not a sample refers to a patient suffering from the common acute leukemia, the gene expression level of the different marker genes has to be compared to the expression level in reference samples derived from healthy individuals. As will be appreciated in the art, once a standard expression level is known, it can be used repeatedly as a standard for comparison. Furthermore samples obtained from individuals suffering from the common acute lymphoblastic leukemia can be used for comparison. In this case, if the test sample and the sample for comparison have been obtained from individuals suffering from this disease, a relative prognosis between these individuals can be provided.

The quantification of the gene expression in the sample for comparison can be performed using the same method as for the test sample or any other method which is known in the art. It is preferred that the same method is used for the test sample and the samples for comparison. The fold change value is calculated as the quotient of probe versus control samples. If the gene is up-regulated, a fold change value $\geq$two is regarded as significant. If the gene is down-regulated, a fold change value $\leq 0.5$ is regarded as significant.

The comparison between the test sample and the control samples allows to identify the differencially expressed genes. The analysis of the expression patterns in these samples reveal which specific genes are up-regulated or down-regulated or normally expressed in the sample. The analysis leads to an arbitrary expression value based on specific hybridization intensity for the genes referring to the common acute lymphoblastic leukemia, wherein the fold change value indicates if a gene is down-regulated or up-regulated or normally expressed. A gene is identified as up-regulated, if the fold change (FC) is greater than 2, preferably greater than 3. A gene is identified as down-regulated if the fold change (FC) is smaller than 0.5, preferably smaller than 0.33. In addition it is preferred to determine the median false discovery rate (FDR) of the method for determining and analyzing the gene expression, whereas it is preferred that the method displays a median false discovery rate of smaller than 10%, more preferred smaller than 7% and even more preferred smaller than 4%.

In order to diagnose a sample as referring to the acute lymphoblastic leukemia, the number of genes which are up-regulated or down-regulated have to be compared to the number of total genes referring to cALL which have been measured. In order to make a reliable diagnosis, it is preferred that at least 40% of these genes are identified as up- or down-regulated. It is even more preferred that at least 60% and further preferred at least 80% of these genes are up- or down-regulated. For example if at least 83% of 40 genes are up-regulated or down-regulated the estimated accuracy is $\geq 98\%$ (using genes from examples 1-3). It is preferred to perform the diagnosis of a sample by using the PAM method. If at least 90% of 42 genes are up-regulated or down-regulated the estimated accuracy is $\geq 92\%$ (using genes from examples 5-6). It is preferred to perform the diagnosis of a sample by using the PAM method.

Tables 1-16 indicate if the genes are up- or down-regulated. If a sample comprises up-regulated genes, which should be down-regulated according to the Tables 1-16 (or comprises down-regulated genes, which should be up-regulated respectively), these genes do not indicate cALL.

Another aspect of this invention is a method for identifying compounds which modulate the expression of the genes referring to the common acute lymphoblastic leukemia. This method comprises contacting compounds with B-cells, obtained from patients suffering from the common acute lymphoblastic leukemia. A comparison between the gene expression in the presence of these compounds and without these compounds allows to identify compounds which can be used to modulate the expression of these genes. The candidate compound may be selected if the expression of said genes in the cells which were contacted with the candidate compound is lower than in the cells which were not contacted with the candidate compound. In such case, the compound is capable of suppressing the expression of the genes referring to the disease. One may further compare the viability of the cells which were contacted with the candidate compound and the viability of cells which were not contacted with the candidate compound.

For example the antisense-, siRNA, antibodies, aptamers, anticalins and other small molecules referring to the genes and their products which are correlated with the common acute lymphoblastic leukemia according to the invention can be used to modulate the gene expression.

The compounds which can modulate the gene expression, especially the antisense RNA, can be used for the treatment of the pediatric common acute lymphoblastic leukemia (cALL). The therapy comprises administering the active compounds or antisense RNA by common pharmaceutically methods.

Another aspect of the present invention is to provide a method for monitoring the progress of the pediatric common acute lymphoblastic leukemia in a patient. By determining the gene expression levels at different points of time in the therapy, it is possible to draw conclusions, whether a therapy shows an effect and the sample displays a level of gene expression which is smaller than at the beginning of a therapy.

The present invention furthermore provides a kit for carrying out the method for diagnosis of cALL according to the present invention. The kit comprises reagents suitable for determining the gene expression levels of the genes of Tables 1-4 and/or Tables 5-16, further preferred of Tables 2-4 and/or 8-16.

Additionally the kit comprises primers suitable for the detection of the individual genes. It is preferred that one pair of primers is suitable to determine more than one gene, further preferred more than three genes. The kit also comprises the reagents necessary for carrying out the PCR reaction and quantitative measuring the amounts of target sequences. The kit further comprises the Taq polymerase. Additionally the kit comprises suitable nucleotide probes for selective quantitative determination of the different gene levels in the sample.

BRIEF DESCRIPTION OF THE FIGURES

(FIG. 1A) These probe sets clustered the controls in a group separate from cALL patient samples. (FIG. 1B) Unsupervised principal component analysis (PCA) of the same data set clearly separated cord blood probes from tumor samples indicating that the expression pattern of normal early pre B cells is distinct from cALL tumor samples FIGS. 2A and FIG. 2B. cALL signature. A signature of 2397 differentially expressed genes, distinguishing cALL and normal control cells, is sufficient for correct classification. With this data set of differentially expressed genes, both, (FIG. 2A) complete linkage hierarchical cluster algorithms and (FIG. 2B) principal component analysis, utilizing the first three principal components, generate correct classification of the investigated samples.

(FIG. 4A) Genechip array expression profiles of selected genes are shown. (FIG. 4B) These were compared to newly prepared bone marrow of leukemic patients and newly prepared fetal B cells. cDNA was analysed by RT-PCR after calibration with β-actin primers.

(FIG. 6A) These probe sets clustered the controls in a group separate from cALL patient samples. (FIG. 6B) Unsupervised principal component analysis (PCA) of the same data set clearly separated cord blood probes from tumor samples indicating that the expression pattern of normal early pre B cells is distinct from cALL tumor samples.

(FIG. 8B) The FEB and cALL classifier show a similar number of non-zero genes although the score of individual genes seems to be higher in FEB.

FIG. 9. Table 1. Displays genes with their uniquid number, gene symbol, gene ID number, as well as T-statistic value (score(d)), fold change value and q-value (giving the lowest False Discovery Rate at which the gene is called significant (J. D. Storey. A direct approach to false discovery rates. J Roy Stat Soc., Ser. B, 64:479-498)) based on SAM analysis identified in examples 1-3.

FIG. 10. Table 2. Represents a selection of most significantly up-regulated genes from Table 1.

FIG. 11. Table 3. Represents a selection of most significantly down-regulated genes from Table 1.

FIG. 12. Table 4. Represents a selection of up-regulated and down-regulated genes with the highest predictive value for the diagnosis of cALL based on PAM analysis resulting in a correct classification of diagnostic probes ≧98%. The genes are displayed like in Table 1.

FIG. 13. Table 5. Displays genes with their uniquid number, gene symbol, gene ID number, as well as T-statistic value (score(d)), fold change value and q-value (giving the lowest False Discovery Rate at which the gene is called significant (J. D. Storey. A direct approach to false discovery rates. J Roy Stat Soc., Ser. B, 64:479-498)) based on SAM analysis identified in Examples 5-6.

FIG. 14. Table 6. Represents the genes common in Table 1 and 5.

FIG. 15. Table 7. Represents the genes of Table 5 unique to SAM analysis of genes identified in Examples 5-6.

FIG. 16. Table 8. Represents a selection of most significantly up-regulated genes from Table 5.

FIG. 17. Table 9. Represents the genes common in Table 2 and 8.

FIG. 18. Table 10. Represents the genes of Table 8 unique to SAM analysis of genes identified in Examples 5-6.

FIG. 19. Table 11. Represents a selection of most significantly down-regulated genes from Table 5.

FIG. 20. Table 12. Represents the genes common in Table 3 and 11.

FIG. 21 Table 13. Represents the genes of Table 11 unique to SAM analysis of genes identified in Examples 5-6.

FIG. 22. Table 14. Represents a selection of up-regulated and down-regulated genes with the highest predictive value for the diagnosis of cALL based on PAM analysis of genes identified in Example 5-6 resulting in a correct classification of diagnostic probes ≧92%. The genes are displayed like in Table 1.

FIG. 23. Table 15. Represents the genes common to Table 4 and 14.

FIG. 24. Table 16. Represents the genes of Table 14 unique to PAM analysis of genes identified in Examples 5-6.

FIG. 25. Tables 17A Represents the up-regulated genes of Table 14.

FIG. 26. Table 17B Represets the down-regulated genes of Table 14.

EXAMPLE 1 a) Patients' Samples

Figure 1A:
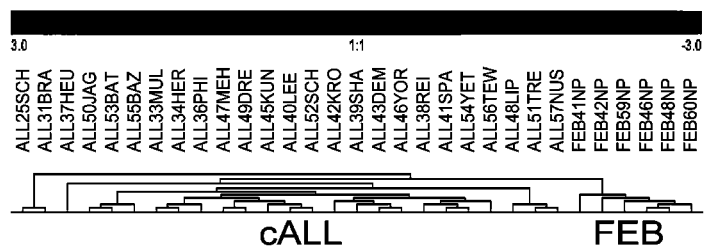
FIGS. 1A and FIG. 1B. Unsupervised clustering and PCA of leukemic and normal control samples. Unsupervised complete linkage hierarchical clustering was carried out with log2 transformed and median centered data (see Examples 1-3) by use of the genesis software package, details for which be found at the web pane maintained by the Institute for Genomics and Bioinformatics, Graz University of Technology (Graz, Austria) and in the article by Sturn A, Quackenbush J, and Traianoski Z. "Genesis: Cluster analysis of microarray data". *Bioinformatics*, Jan. 2002, vol. 18(1): 207-8. U133A probe sets were subsequently filtered for a standard deviation $\geq 1.2$ resulting in 9139 genes that passed these criteria.

Samples of cryopreserved bone marrow derived lymphoblasts from children with cALL were obtained after IRB (internal review board) approval and with informed consent at the time of initial diagnosis prior to any therapy. Patients' samples used for microarray analysis and clinical data have been received from the international ALL-BFM study (Leukemia 2000; 14(12):2205-22). The median age of the patients was 6.1 years (range 0.6-15.2 years); the male to female ratio was 0.93. Mean lymphoblast percentage in all samples analyzed was greater than 90%. Five patients exhibited the TEL/AML1 translocation t(12; 21)(p13; q22). Only one patient showed a translocation involving the MLL gene at chromosome 11q23. Samples analysed by RT-PCR were drawn from bone marrow of leukemia patients with varying blast content after informed consent and IRB approval of the local ethics committee in the Children's Hospital Medical Center, Munich University of Technology.

b) Control Samples

Control lymphocytes have been separated from umbilical cord blood of healthy and termed newborns taken directly after birth with IRB approval and informed consent. The cord blood was drawn in the University Hospital for Obstetrics and Reproduction Medicine at the Martin-Luther-University, Halle-Wittenberg, Germany. From 8 umbilical cords 42-90 ml (mean 62 ml) blood containing $6.9-20.0 \times 10^7$ cells (mean $11.3 \times 10^7$) was obtained for further separation of B cells.

EXAMPLE 2 a) Separation of B Cells from Normal Cord Blood

Following density gradient centrifugation using Ficoll Hypaque (Amersham Pharmacia Biotech; Freiburg, Germany) lymphocytes were purified by use of a "B Cell Isolation Kit" (Miltenyi Biotech; Bergisch Gladbach, Germany) according to the manufacturer's recommendation. All non-B cells were magnetically labeled with antibodies against CD2 (CD=cluster designation) and CD4 (T-cells and NK (natural killer) cells), CD11b (granulocytes and monocytes), CD16 and CD36 (monocytes and platelets), and IgE-antibodies (mast cells and basophile granulocytes), whereas B cells remained untouched. B cell purity and yield were determined prior to and after separation using flow cytometry (FACScan; Becton Dickinson Bioscience, Heidelberg, Germany). Initial mean B cell percentage of total living lymphocytes in cord blood samples was 9.0±4.1% (CD19+) and 3.4±2.1% for early B cells (CD19+/CD10+). Mean B cell percentage after separation was 81.9±10.6% (CD19+) and 27.4±6.4% for early B cells (CD19+/CD10+).

b) Leukemic Cell Lines

Three leukemic cell lines (NALM-6, 697, MHH-CALL-2) of pediatric human B cell precursor leukemias (diagnosed as cALL), obtained from the German Collection of Microorganisms and Cell Cultures (DSMZ; Braunschweig, Germany), were cultivated in medium containing 80% RPMI 1640 and 20% FCS with additional 1% penicillin/streptomycin in humidified atmosphere at 37° C. and 5% $CO_2$.

c) RNA Preparation

Total RNA was prepared from cryopreserved leukemic cells or from freshly separated healthy B cells with acid phenol/chloroform extraction (TRIzol, Invitrogen; Karlsruhe, Germany) followed by purification with RNeasy Mini Kit (Qiagen; Hilden, Germany) according to the manufacturer's instructions and was quantified spectrophotometrically. The quality of the purified RNA was assessed by visualization of 18S and 28S RNA bands after electrophoresis through agarose gels and staining with ethidium bromide.

EXAMPLE 3 a) Microarray Expression Analysis

A total of 10 µg RNA from each sample was used to prepare biotinylated target cRNA as previously described (Staege et al., Klin Padiatr 2003;215(3):135-9.; Staege et al., Cancer Res 2004;64(22):8213-21.; Hofmann H-S et al., Clin Cancer Res 2005;11(3):1086-92.) A detailed protocol is available through the web pane maintained by Affymetrix (Santa Clara, USA). Samples were hybridized to HG-U133A microarrays and analyzed using Affymetrix software "Microarray Suite 5.0" and "Data Mining Tool 3.0" (Affymetrix; Santa Clara, USA). For normalization all microarrays have been scaled to the same target intensity of 500 (default setting) using a trimmed mean signal of all probe sets. Subsequent analysis was carried out with signal intensities that were log2 transformed for equal representation of over- and under-expressed genes and then median centered to remove biases based on single expression values. Unsupervised hierarchical clustering (Eisen et al., Proc Natl Acad Sci U S A 1998;95(25): 14863-8) and principal component analysis were accomplished by use of the "Genesis" software package (Stum et al. Bioinformatics 2002;18(1):207-8.). For identification of differentially expressed genes we used significance analysis of microarrays (SAM) (Tusher et al., Proc Natl Acad Sci U S A 2001;98(9):5116-21.). To identify genes that may be utilized to further classify the malignant state of cALL, we employed prediction analysis of microarrays (PAM) (Tibshirani et al., Proc Nail Acad Sci U S A 2002;99(10):6567-72.).

b) Semiquantitative RT-PCR

Total RNA was reverse transcribed using the Superscript First-Strand Synthesis System with oligo-dT primers (Invitrogen; Karlsruhe, Germany) according to the manufacturer's instructions. Polymerase chain reaction (PCR) was performed using AmpliTaq DNA Polymerase (Applied Biosystems; Darmstadt, Germany). Before amplification of specific genes cDNA was calibrated by use of β-actin primers 5'-GGCATCGTGATGGACTCCG-3' (forward) (SEQ ID NO: 1) and 5'-GCTGGAAGGTGGACAGCGA-3' (reverse) (SEQ ID NO: 2). Amplification for detection was carried out with the following primers:, DTR (diphtheria toxin receptor (heparin-binding epidermal growth factor-like growth factor)) -forward 5'-TGGGGCTTCTCATGTTTAGG-3'(SEQ ID NO: 3), DTR-reverse 5'-ACTGGGGACGAAG-GAGTCTT-3'(SEQ ID NO: 4); LILRA2 (leukocyte immunoglobulin-like receptor, subfamily A (with TM domain), member 2)-forward 5' -CCCTGGACATCCTGATCACA-3'(SEQ ID NO: 5, LILRA2-reverse 5'-GGAATTCAGCCTGGT-TCTGC-3' (SEQ ID NO: 6); SPRY2 (sprouty, drosophila, homolog of, 2) -forward 5'-ATCTGCCAGGAAAAGG-GACT-3'(SEQ ID NO: 7), SPRY2-reverse 5'-GGTCACTC-CAGCAGGCTTAG-3'(SEQ ID NO: 8), and STK32B (serine/threonine kinase 32B) -forward 5'-GCAGCACT-GTTTGGAGACTG-3'(SEO ID NO: 9), STK32B-reverse 5'-TGAGGAGGTTGTGTTGCAC-3'(SEQ ID NO: 10).

Results from Examples 1-3 a) Differentially Expressed Genes

Expression of cell surface markers CD19 and CD10 in cALL correlates with early pre B cells stage of lymphocyte differentiation. Umbilical cord blood contains more early pre B cells than other sources. Up to 14% of the lymphocytes in umbilical cord blood are CD19 expressing B cells and 0.5-1.5% are early pre B cells expressing CD19 and CD10 surface antigens (22-24). Thus, cord blood derived, fetal CD19+ CD10+ double positive early pre B cells may constitute appropriate controls for comparative gene expression analyses of normal versus leukemic early pre B cells. Cells were purified as described in Material and Methods for further analysis. In total, 29 cALL and 8 control samples of sorted B cells have been profiled for gene expression. Mean lymphoblast percentage in patients' samples was 91%, suspending the need for further enrichment of leukemic blasts. Chip analysis detected an average of 31.4±4.9% of present genes expressed in the samples. Differences in scaling factor were less than fivefold for 31 arrays.

Figure 1B:
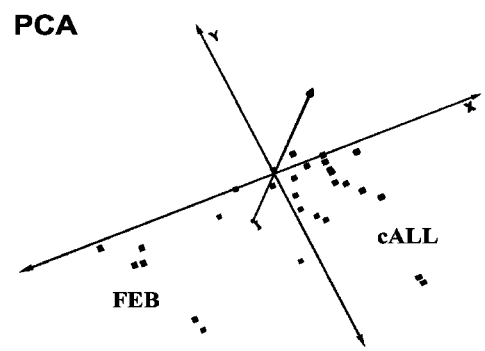

Unsupervised hierarchical clustering was carried out with log 2 transformed and median centered data (see Materials and Methods). U133A probe sets were subsequently filtered for a standard deviation ≧1.2 resulting in 9139 genes that passed these criteria. These genes clustered the controls in a group separate from cALL patient samples. Similarly, unsupervised principal component analysis (PCA) of this data set clearly separated cord blood from leukemia samples, indicating that the expression pattern of normal early pre B cells is clearly distinct from the expression pattern of cALL (FIG. 1). However, cluster data also indicate that normal early pre B cells have an apparent relationship to cALL samples. To identify differentially expressed genes between cALL and control samples based on their pattern of variation in signal intensity we used SAM (Tusher et al., Proc Natl Acad Sci USA 2001; 98(9):5116-21).

Figure 2A:
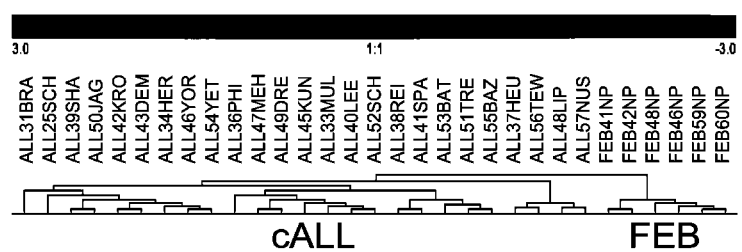
Figure 2B:
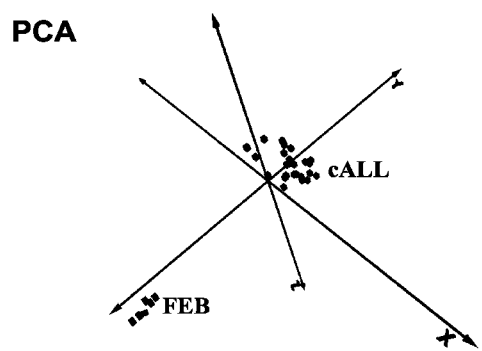

This analysis identified 2397 genes, of which 1450 were up-regulated and 947 down-regulated, with a fold change (FC)≧2 and a median false discovery rate (FDR)≦6.3%. Further selection based on present and absent calls (prerequisite: down-regulated genes present in 5/6 controls, up-regulated genes present in 9/25 leukemia samples) reduced the number down to 723 up- and 617 down-regulated genes, respectively. Subsequent analysis of this "cALL signature" of differentially expressed genes recognized 342 genes with significant up-regulation FC≧3 in leukemic cells (maximum fold change 257). On the other hand 293 genes representing RNAs with significant down-regulation FC≧3 in comparison to control cells (maximum fold change 129) were detected. This particular expression profile enables discrimination of leukemic from control samples and is specific for cALL. Hierarchical cluster algorithms and principal component analysis (FIG. 2) generate correct classification of the samples with this data set.

This is the first study, which compares normal fetal early pre B (FEB) cells to cALL cells. In contrast, various previous studies compared different types of leukemia or subtypes within cALL. The data set of the present invention was compared to that of a previous study by Ross et al. (Ross M E, Zhou X, Song G, et al. Classification of pediatric acute lymphoblastic leukemia by gene expression profiling. Blood. 2004; 104(12):3679-87.) which used the identical chip platform of Affymetrix U133 microarray chips facilitating evaluation: Only 126 of over 2397 probe sets differentially expressed in our cALL signature were also differentially expressed between different cALL samples of Ross et al. Similarly, when we compared data sets based on gene ontology (GO, http://www.geneontology.org) annotation with those of Fine et al. (Blood 2004; 103(3):1043-1049), keeping in mind that some of them are not yet annotated, only 21.7% of our genes were shared with their published data set.

One reason for this little overlap might be that both data sets are perhaps differently skewed by subgroups of cALL, defined e.g. by translocations. In our data set 5 cases with TEL/AML1 translocation and one with MLL/x translocation were present. To analyze skewing by subgroups in further detail, we identified differentially expressed genes in our TEL/AML1 data set by SAM (Tusher et al., Proc Natl Acad Sci USA 2001; 98(9):5116-21). To this end, the 5 TEL/AML1 samples were directly compared to fetal B cell controls, 931 genes were selected with a FC=2 and FDR≧3.49%. From these genes, genes already detected after cALL vs. fetal B cell comparison were subtracted. Subtraction resulted in 283 genes that were differentially expressed in TEL/AML1 samples.

When we compared these genes with those identified for samples with TEL/AML1 translocation by Ross et al. (Ross et al., Blood. 2004; 104(12):3679-87), the overlap was only 24 genes. Similarly, only 21.4% of annotated genes found differentially expressed by Fine et al. (Blood 2004; 103(3): 1043-1049.) were re-identified in our differentially expressed genes. This argues against the possibility that the observed differences are mainly due to differences in tumor samples and supports our assumption that the difference is due to the different approach and we thus identified a unique data set by comparing cALL to normal fetal B cells.

b) Malignant Phenotype

Differentially expressed genes, in addition, contain functional genomic information about the molecular pathogenesis of cALL. To identify a molecular signature for specific disease mechanisms, differentially expressed genes were subdivided into functionally related groups, according to the leukemic blast cells= B cellular origin and to different aspects of a malignant phenotype. Grouping of genes followed GO gene descriptions. Groups of genes prominently up-regulated in pediatric cALL included those for cell cycle, cell growth and apoptosis, whereas those for immune responses were significantly down-regulated.

Overall 18 of a total 54 genes differentially expressed and associated with immune function according to GO, were found to be up-regulated with a maximum fold change of 29.6 for VPREB1 (pre-B-lymphocyte gene 1) expressed at early stages of B cell differentiation and found to be present in adult and pediatric cALL (Bauer et al., Blood 1991; 78(6):1581-8, and Lemmers et al., Leukemia 2000; 14(12):2103-11.) and BLR1, also known as CXCR5 chemokine receptor as a down-regulated gene with a fold change of 29.6. Out of 83 genes differentially expressed and involved in cell growth and DNA replication 48 genes were up-regulated in cALL.

For example bone morphogenetic protein (BMP2) and transcription factor ETS2 (v-ets avian erythroblastosis virus e26 oncogene homolog) (FC 14.8 and 13.1, respectively) were found to be most prominently up-regulated in cALL, whereas transcription factor E2F5 (FC 0.094) and tyrosine kinase LYN (v-yes-1 Yamaguchi sarcoma viral related oncogene homolog) (FC 0.149), previously found to be associated with myeloid leukemias (Roginskaya et al., Leukemia 1999; 13(6):855-61), were significantly down-regulated. BMP2 belongs to the transforming growth factor-beta (TGF-β) superfamily and has also been identified by Fine et al. (Blood 2004; 103(3):1043-1049.) as differentially expressed in cALL.

Interestingly, of the 38 genes differentially expressed (with 21 genes up-regulated) and involved in apoptosis, the transcription factor fos-like antigen 2 (FOSL2) also known as FRA2 (fos-related antigen 2), previously not associated with leukemia, was most prominently up-regulated (FC 17.1), whereas the baculoviral IAP repeat-containing protein (BIRC3) overexpressed in chronic lymphocytic leukemia (Nakagawa et al., Leuk Res 2004; 28(5):487-94.) was significantly down-regulated (FC 0.063).

c) Expression Profiling Correctly Predicts the Malignant Phenotype

Differential gene expression between leukemia samples and normal controls may include patterns of variation in expression that can be used for classification of samples. To do this we used prediction analysis of microarrays (PAM) (Tibshirani et al., Proc Natl Acad Sci USA 2002; 99(10): 6567-72.) that identifies samples based on shrunken centroids of gene expression. This is accomplished via the identification of a small set of genes that define a distinctive molecular signature for discrete classes of samples. A set consisting of 15 cALL samples and four fetal B cell samples was used to train the classifier.

Figure 3A:
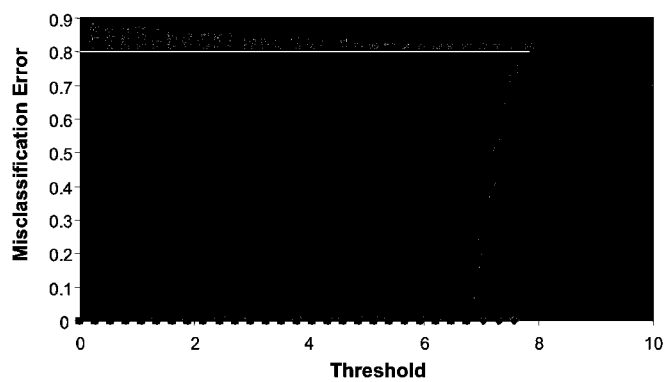
FIGS. 3A, FIG. 3B, and FIG. 3C. Classification of samples based on prediction analysis of microarrays. A probe set consisting of 15 cALL samples and 4 fetal B cell samples was used to train the classifier. After cross validation the accuracy of the classifier was tested over a range of thresholds (FIG. 3A). Over a broad range of thresholds the tumor and control samples were to 100% correctly classified up to threshold values of 5 (FIG. 3B). Our test set comprised samples that were not included in the training set and, in addition, included tumor probes and control probes already investigated by SAM as well as pediatric cALL lines (NALM-6, CALL-2, 697) and a so far not analysed tumor sample that was clinically identified as a CD10 positive non-Hodgkin's lymphoma (NHL HTC). With a classifier of 14 genes (threshold value 4.5) all test probes were correctly classified (FIG. 3C). The FEB and cALL classifier show a similar number of non-zero genes although the score of individual genes seems to be higher in FEB.

After cross validation, the accuracy of the classifier was tested over a range of thresholds. The classifier is consists of significant genes identified based on their expression pattern within leukemia or normal FEB able to distinguish both groups. We observed that over a broad range of thresholds the leukemia and control samples were to 100% correctly classified (FIG. 3A). A given threshold defines the number of genes or so called shrunken centroids to be included in the test. We tested our classifier at distinct thresholds and found that up to values of 5 (6 genes) our classifier was accurate. Our test set comprised samples that were not included in the training set and included leukemia probes and control samples already investigated by SAM as well as cALL lines (NALM-6, CALL-2, 697) and a so far not analyzed sample that was clinically identified as a CD10 positive non-Hodgkin's lymphoma.

Figure 3B:
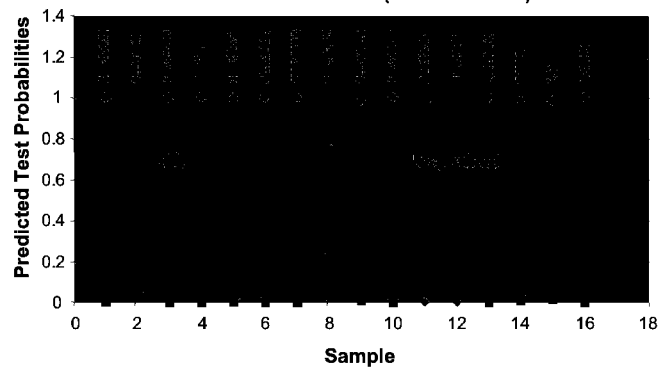
Figure 3C:
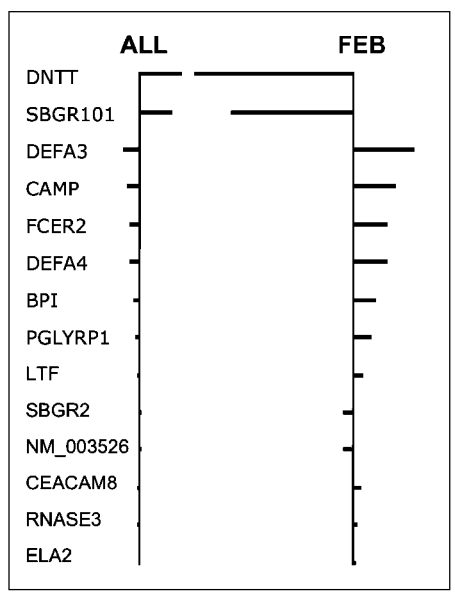
Figure 4A:
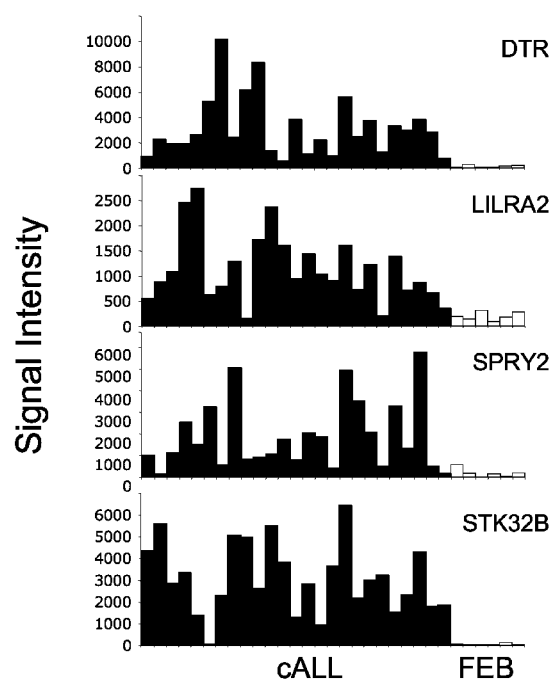
FIGS. 4A and FIG. 4B. Target validation of selected gene profiles by RT-PCR.
Figure 4B:
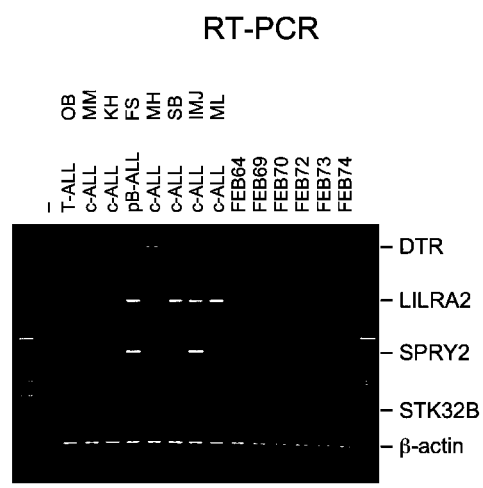
Figure 5:
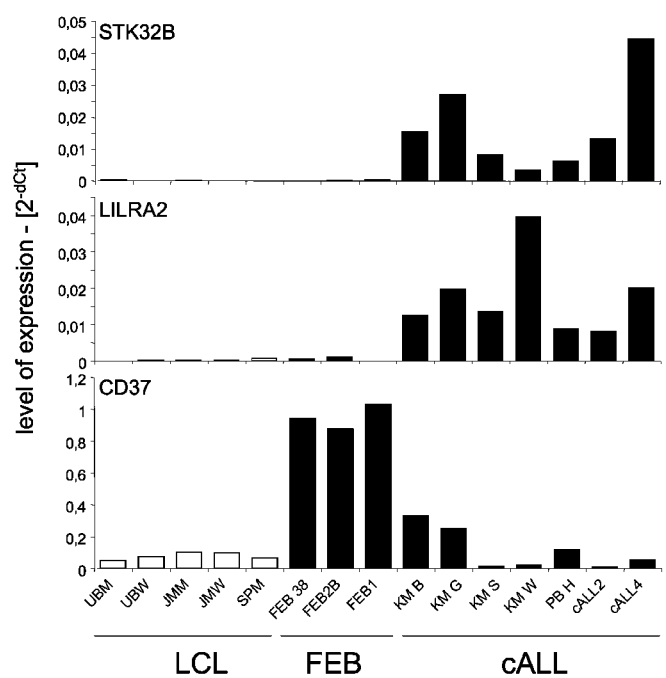
FIG. 5. Diagnostic genes are leukemia specific. Differential expression of selected genes were analysed for expression in leukemia samples (cALL) in comparison to fetal B cells (FEB) and EBV transformed B cells (LCL).

All test samples were correctly classified (FIG. 3B), even the described cell lines for which a variable expression pattern, due to cell culture conditions, is known. However, we already knew from hierarchical cluster analysis of a close relationship in gene expression patterns between cALL lines and primary samples (data not shown). The fetal early pre B (FEB) cell and cALL classifier show a similar number of non-zero genes (FIG. 3C) although the score of individual genes seems to be higher in FEB cells. One gene that had the highest cALL score besides terminal deoxynucleotidyltransferase (DNTT) was previously not associated with cALL. The list of genes that comprise this classifier is contained within table 4.

EXAMPLE 4

Method for cALL-diagnosis of Samples from Patients a) Sample Preparation and b) RNA Isolation are According Methods in Example 2 c) Quantitative Analysis of Test Sample and Control Sample

A total of 10 μg RNA from each sample is used to prepare biotinylated target cRNA as previously described (Staege et al., Klin Padiatr 2003;215(3):135-9. Staege et al., Cancer Res 2004;64(22):8213-21. Hofmann et al., Clin Cancer Res 2005; 11(3):1086-92). A detailed protocol is available through the web page maintained by Affymetrix (Santa Clara, USA). Samples are hybridized either to HG-U133A microarrays and derivatives or custom designed arrays manufactured based on the genes illustrated in table 2-4. Hybridized microarrays are normalized and subsequent analysis is carried out with signal intensities that are log2 transformed for equal representation of over- and under-expressed genes and then median centered to remove biases based on single expression values. Unsupervised hierarchical clustering (Eisen et al., Proc Natl Acad Sci USA 1998;95(25):14863-8) and principal component analysis is accomplished by use of the "Genesis" software package (Stunt et al. Bioinformatics 2002;18(1):207-8).

Additional details may be found at the web page maintained by the Institute for Genomics and Bioinformatics, Graz University of Technology (Graz, Austria) and in the article by Sturn A, Quackenbush J, and Traianoski Z. "Genesis: Cluster analysis of microarray data". *Bioinformatics*, Jan. 2002, vol. 18(1): 207-8. For the identification of differentially expressed genes significance analysis of microarrays (SAM) is used (Tusher et al., Proc Natl Acad Sci USA 2001;98(9):5116 21) and the false discovery rate of measured expression values by focussing on expression values of genes in Table 1 is determined. To classify sample probes according to their expression profile in malignant or healthy prediction analysis of microarrays (PAM) is employed (Tibshirani et al., Proc Natl Acad Sci U S A 2002;99(10):6567-72 ) and utilize genes identified in Table 4 for class prediction are utilized.

d) Comparison of the Gene Expression Profiles and Evaluation is performed according to methods described in example 3, preferentially analysis of selected genes by real time PCR is carried out.

EXAMPLE 5 a) Separation of B Cells from Normal Cord Blood Using CD19 and CD10 Purification Following density gradient centrifugation using Ficoll Hypaque (Amersham Pharmacia Biotech; Freiburg, Germany) B-lymphocytes were purified by use of CD19+ magnetic beads Dynal Biotech/Invitrogen (Karlsruhe, Germany) according to the manufacturer's recommendation. Labeled B-cells were detached from magnetic particles with CD19 DetechaBeads, subsequently labelled with CD10-PE and further purified by use of anti-PE microbeads (Miltenyi Biotech; Bergisch Gladbach, Germany). B cell purity and yield were determined prior to and after separation using flow cytometry (FACScan; Becton Dickinson Bioscience, Heidelberg, Germany). Initial mean B cell percentage of total living lymphocytes in cord blood samples was 9.0±4.1% (CD19+) and 3.4±2.1% for early B cells (CD19+/CD10+). Mean B cell percentage after separation was 85.9±10.6% (CD19+) and 88.9±6.8% for early B cells (CD19+/CD10+).

b) Leukemic Cell Lines

The leukemic cell lines and EBV immortalized LCL were prepared as in Example 2b.

c) RNA Preparation

The RNA preparation was performed as in Example 2c.

EXAMPLE 6 a) Microarray Expression Analysis

The microarray expression analysis was carried out as in Example 3a.

b) Semiquantitative RT-PCR

Reverse transcription and RT PCR were carried out as outlined in Example 3b. Amplification for detection for additional genes was carried out with the following primers: HMGB2 (high mobility group box 2) -forward 5'-CGGACTCTTCCGTCAATTTC-3' (SEO ID NO: 15), HMGB2-reverse 5'-TATCACCTUGGGAGGAACG-3'(SEQ ID NO: 16); LILRB2-forward 5'-GGTCTTCCCTGAAGCATCTC-3'(SEO ID NO: 11), LILRB2-reverse 5'-CCCTGACAACT-GAGGGTGAC-3'(SEQ ID NO: 12); PLXNB2 (PLEXIN B2)-forward 5'-AGAGAGGCAGCGTGAAAGAG-3'(SEQ ID NO: 13), PLXNB2-reverse 5'-GCGGTAAGCTGT-TCGTCTTC-3'(SEO ID NO: 14);

c) Real-time RT-PCR

Reverse transcription was carried out as outlined in Example 3b. Primer sets for real-time PCR were used from Qiagen (Hilden, Germany) for CD37 (Hs_CD37__1_SG), HMGB2 (Hs_HMGB2__1_SG) and STK32B (Hs_STK32B__1_SG).

Results from Examples 5-6 a) Differentially Expressed Genes

The results from Examples 5-6 confirm the results of Examples 1-3. In total, 29 cALL and 11 control samples of sorted B cells, including 3 batch-samples of highly purified CD10+CD19+ B cells representing 16 individual probes, have been profiled for gene expression in Examples 5-6. Mean lymphoblast percentage in patients' samples was 91%, suspending the need for further enrichment of leukemic blasts. Chip analysis detected an average of 31.4±4.9% of present genes expressed in the samples. Differences in scaling factor were less than fivefold for 34 arrays.

Figure 6A:
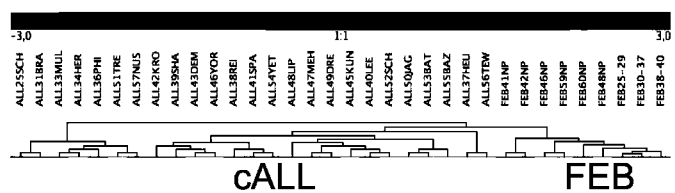
FIGS. 6A and FIG. 6B. Unsupervised clustering and PCA of leukemic and normal control samples. Unsupervised complete linkage hierarchical clustering was carried out with log2 transformed and median centered data (see Examples 5-6) by use of the genesis software package, details for which be found at the web nate maintained by the Institute for Genomics and Bioinformatics, Graz University of Technology (Graz, Austria) and in the article by Sturn A, Ouackenbush J, and Traianoski Z. "Genesis: Cluster analysis of microarray data". *Bioinformatics*, Jan. 2002, vol. 18(1): 207-8. U133A probe sets were subsequently filtered for a standard deviation $\geq 1.1$ resulting in 10729 genes that passed these criteria.
Figure 6B:
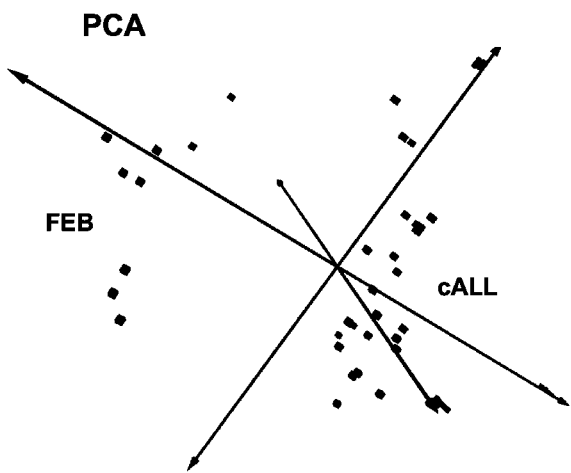
Figure 7A:
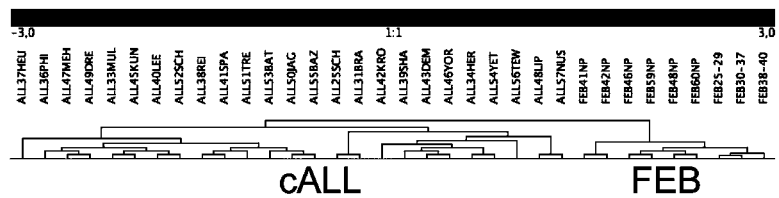
FIGS. 7A and FIG. 7B. cALL signature. A signature of 1593 differentially expressed genes, distinguishing cALL and normal control cells, is sufficient for correct classification. With this data set of differentially expressed genes, both, (FIG. 7A) complete linkage hierarchical cluster algorithms and (FIG. 7B) principal component analysis, utilizing the first three principal components, generate correct classification of the investigated samples.
Figure 7B:
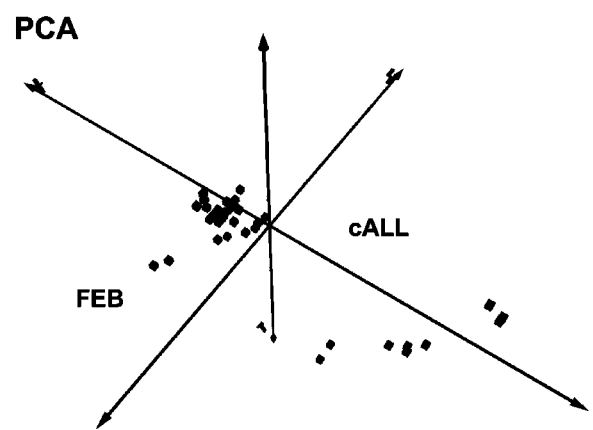

Unsupervised hierarchical clustering was carried out with log 2 transformed and median centered data (see Materials and Methods). U133A probe sets were subsequently filtered for a standard deviation ≧1.1 resulting in 10729 genes that passed these criteria. These genes clustered the controls in a group separate from cALL patient samples. Similarly, unsupervised principal component analysis (PCA) of this data set clearly separated cord blood from leukemia samples, indicating that the expression pattern of normal early pre B cells is clearly distinct from the expression pattern of cALL (FIG. 6). However, cluster data also indicate that normal early pre B cells have an apparent relationship to cALL samples. To identify differentially expressed genes between cALL and control samples based on their pattern of variation in signal intensity we used SAM (Tusher et al., Proc Natl Acad Sci USA 2001; 98(9):5116-21).

This analysis comparing leukemic probes with the highly purified CD10+CD19+ B cells identified 1593 genes, of which 899 were up-regulated and 694 down-regulated, with a fold change (FC)≧2 and a median false discovery rate (FDR) ≦10.2%. Further selection based on present and absent calls (prerequisite: down-regulated genes present in 3/3 batch controls, up-regulated genes present in 9/25 leukemia samples) reduced the number down to 487 up- and 572 down-regulated genes, respectively. Subsequent analysis of this "cALL signature" of differentially expressed genes recognized 367 genes with significant up-regulation FC≧3 in leukemic cells (maximum fold change 124). On the other hand 338 genes representing RNAs with significant down-regulation FC≧3 in comparison to control cells (maximum fold change 28) were detected. This particular expression profile enables discrimination of leukemic from control samples and is specific for cALL. Hierarchical cluster algorithms and principal component analysis (FIG. 2) generate correct classification of the samples with this data set.

b) Expression Profiling Correctly Predicts the Malignant Phenotype

Differential gene expression between leukemia samples and normal controls may include patterns of variation in expression that can be used for classification of samples. To do this we used prediction analysis of microarrays (PAM) (Tibshirani et al., Proc Natl Acad Sci USA 2002; 99(10): 6567-72.) that identifies samples based on shrunken centroids of gene expression. This is accomplished via the identification of a small set of genes that define a distinctive molecular signature for discrete classes of samples. A set consisting of 15 cALL samples and three fetal B cell batches comprising 16 different highly purified samples was used to train the classifier.

After cross validation, the accuracy of the classifier was tested over a range of thresholds. The classifier is consists of significant genes identified based on their expression pattern within leukemia or normal FEB able to distinguish both groups. We observed that over a broad range of thresholds the leukemia and control samples were to 100% correctly classified. A given threshold defines the number of genes or so called shrunken centroids to be included in the test. We tested our classifier at distinct thresholds and found that up to values of 4 (20 genes) our classifier was accurate. Our test set comprised samples that were not included in the training set and included leukemia probes and control samples already investigated by SAM as well as cALL lines (NALM-6, CALL-2, 697) and a so far not analyzed sample that was clinically identified as a CD10 positive non-Hodgkin's lymphoma.

Figure 8A:
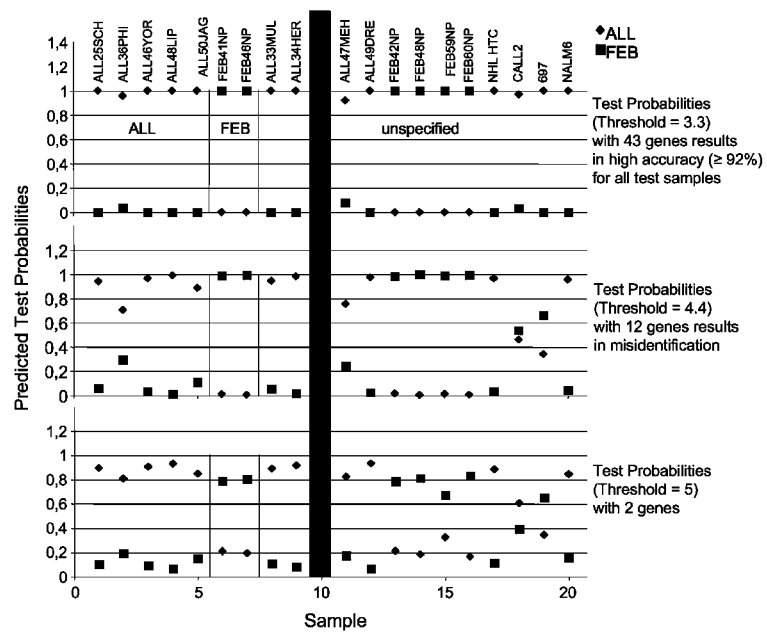
FIGS. 8A and FIG. 8B. Classification of samples based on prediction analysis of microarrays. A probe set consisting of 15 cALL samples and 3 highly purified fetal B cell samples (representing 16 individual probes) was used to train the classifier. After cross validation the accuracy of the classifier was tested over a range of thresholds (FIG. 8A). Over a broad range of thresholds the tumor and control samples were to 92% correctly classified up to threshold values of 3.3 (test probability should approximate 1). Our test set comprised samples that were not included in the training set and, in addition, included tumor probes and control probes already investigated by SAM as well as pediatric cALL lines (NALM-6, CALL-2, 697) and a so far not analysed tumor sample that was clinically identified as a CD10 positive non-Hodgkin's lymphoma (NHL HTC). With a classifier of 43 genes (threshold value 3.3) all test probes were correctly classified. Test set prediction with only 12 genes results in misidentification (FIG. 8A, middle panel).
Figure 8B:
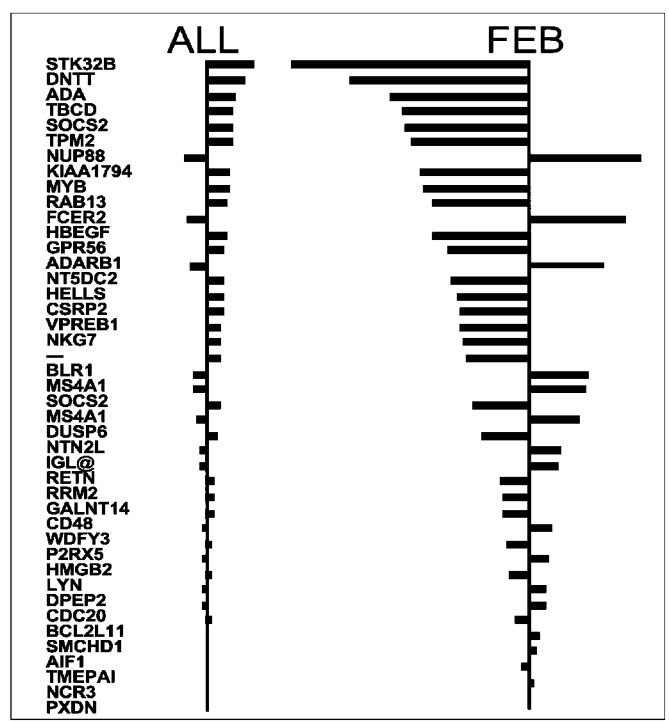

All test samples were correctly classified (FIG. 8A) with 43 individual genes that offer the highest predictive value, even the described cell lines for which a variable expression pattern, due to cell culture conditions, is known. However, we already knew from hierarchical cluster analysis of a close relationship in gene expression patterns between cALL lines and primary samples (data not shown). The fetal early pre B (FEB) cell and cALL classifier show a similar number of non-zero genes (FIG. 8A) although the score of individual genes seems to be higher in FEB cells. Test set prediction with only 12 genes results in misidentification (FIG. 8A, middle panel). The list of genes that comprise the accurate classifier (FIG. 8B) is contained within table 14.

The invention claimed is:

1. A method for diagnosing common acute lymphoblastic leukemia (cALL) in a subject by distinguishing between normal and common acute lymphoblastic leukemic (cALL) cells, wherein the method comprises the steps of:
   (a) providing a test sample comprising CD+19 B cells from blood, bone marrow or bone marrow-derived lymphoblasts obtained from said subject;
   (b) providing an array consisting of 30 to 200 polynucleotide probes complementary to a set of test genes, wherein at least 30 of said probes are complementary to cALL specific target genes set forth in Tables 17A and 17B;
   (c) using the array of step (b) to calculate the quantity of mRNA corresponding to said test genes and thus determine the expression of the test genes in said test sample,
   (d) comparing the expression of said test genes in said test sample to the expression of said genes in a control sample consisting essentially of purified B cells derived from a healthy individual;
   (e) characterizing a cALL specific target gene as dysregulated in the test sample as compared to the control sample if either (a) said target gene is set forth in Table 17A and its expression increases by a factor of 2 or more, or (b) said target gene is set forth in Table 17B and its expression decreases by a factor of 2 or more; and
   (f) diagnosing said subject with cALL if at least 60% of said cALL specific target genes are identified as dysregulated.

2. The method according to claim 1, wherein the test sample and the control sample include CD10+CD19+B-cells.

3. The method according to claim 1, wherein said cALL specific target genes include at least 7 up-regulated genes selected from the genes set forth in Table 17A and at least 7 down-regulated genes selected from the genes set forth in Table 17B, provided that each gene can be selected once only.

4. The method according to claim 1, wherein said cALL specific target genes include at least 10 up-regulated genes selected from the genes set forth in Table 17A and at least 10 down-regulated genes selected from the genes set forth in Table 17B, provided that each gene can be selected once only.

5. The method according to claim 1, wherein said cALL specific target genes include at least one gene selected from the genes set forth in Table 15.

6. The method according to claim 1, wherein said cALL specific target genes include all the genes set forth in Table 15.

7. The method according to claim 1, wherein said cALL specific target genes include at least one gene selected from the genes set forth in Table 16.

8. The method according to claim 1, wherein said cALL specific target genes include all the genes set forth in Table 16.

9. The method according to claim 1, wherein said cALL specific target genes include at least 40 genes selected from the genes set forth in FIG. 8B.

10. The method according to claim 1, wherein said cALL specific target genes include all the genes set forth in FIG. 8B.

11. The method according to claim 1, wherein the step (c) of determining the gene expression comprises the use of hybridization technology and/or polymerase chain reactions (PCR).

12. The method according to claim 1, wherein the hybridization technology utilized comprises the step of hybridizing the mRNAs or cDNAs of the samples with complementary nucleotide probes immobilized on a solid support.

13. The method according to claim 1, wherein the PCR method utilized comprises real-time-PCR.

14. The method according to claim 1, wherein the PCR method utilized comprises the steps of:
   a) contacting a mixture of mRNAs or codas obtained from said test and control samples with amplification reagents comprising pairs of primers, wherein said pairs of primers substantially correspond or are substantially complementary to the gene sequences of the genes to be determined;
   b) carrying out an amplification reaction;
   c) measuring the generation of amplification products; and
   d) determining the quantity of mRNA in said samples from the results obtained in step c).

15. The method according to claim 1, wherein a target gene is defined as dysregulated in the test sample as compared to the control sample if either (a) said gene is set forth in Table 17A and its expression increases by a factor of 3 or more 3, or (b) said gene is set forth in Table 17B and its expression decreases by a factor of 3 or more .

16. The method according to claim 1, wherein said subject is diagnosed with common acute lymphoblastic leukemia if at least 80% of said cALL specific target genes are identified as dysregulated.

17. The method according to claim 1, wherein the subject is a child.

* * * * *

UNITED STATES PATENT AND TRADEMARK OFFICE
CERTIFICATE OF CORRECTION

PATENT NO. : 8,530,155 B2
APPLICATION NO. : 12/377863
DATED : September 10, 2013
INVENTOR(S) : Stefan Burdach et al.

It is certified that error appears in the above-identified patent and that said Letters Patent is hereby corrected as shown below:

In the Specification

At column 17, line 50, please replace the word "pane" with the word --page--.

At column 18, line 37, please replace the word "nate" with the word --page--.

At column 19, line 66, please replace the word "Represets" with the word --Represents--.

At column 21, line 12, please replace the word "pane" with the word --page--.

At column 21, line 32, please replace the word "Nail" with the word --Natl--.

Signed and Sealed this
Third Day of December, 2013

Margaret A. Focarino
*Commissioner for Patents of the United States Patent and Trademark Office*

SEQUENCE LISTING

<160> NUMBER OF SEQ ID NOS: 16

<210> SEQ ID NO 1
<211> LENGTH: 19
<212> TYPE: DNA
<213> ORGANISM: Artificial
<220> FEATURE:
<223> OTHER INFORMATION: beta-actin forward-primer

<400> SEQUENCE: 1
ggcatcgtga tggactccg                    19

<210> SEQ ID NO 2
<211> LENGTH: 19
<212> TYPE: DNA
<213> ORGANISM: Artificial
<220> FEATURE:
<223> OTHER INFORMATION: beta-actin reverse-primer

<400> SEQUENCE: 2
gctggaaggt ggacagcga                    19

<210> SEQ ID NO 3
<211> LENGTH: 20
<212> TYPE: DNA
<213> ORGANISM: Artificial
<220> FEATURE:
<223> OTHER INFORMATION: DTR forward-primer

<400> SEQUENCE: 3
tggggcttct catgtttagg                   20

<210> SEQ ID NO 4
<211> LENGTH: 20
<212> TYPE: DNA
<213> ORGANISM: Artificial
<220> FEATURE:
<223> OTHER INFORMATION: DTR reverse-primer

<400> SEQUENCE: 4
actggggacg aaggagtctt                   20

<210> SEQ ID NO 5
<211> LENGTH: 20
<212> TYPE: DNA
<213> ORGANISM: Artificial
<220> FEATURE:
<223> OTHER INFORMATION: LILRA2 forward-primer

<400> SEQUENCE: 5

-continued ccctggacat cctgatcaca                                          20

<210> SEQ ID NO 6
<211> LENGTH: 20
<212> TYPE: DNA
<213> ORGANISM: Artificial
<220> FEATURE:
<223> OTHER INFORMATION: LILRA2 reverse-primer

<400> SEQUENCE: 6
ggaattcagc ctggttctgc                                          20

<210> SEQ ID NO 7
<211> LENGTH: 20
<212> TYPE: DNA
<213> ORGANISM: Artificial
<220> FEATURE:
<223> OTHER INFORMATION: SPRY2 forward-primer

<400> SEQUENCE: 7
atctgccagg aaaagggact                                          20

<210> SEQ ID NO 8
<211> LENGTH: 20
<212> TYPE: DNA
<213> ORGANISM: Artificial
<220> FEATURE:
<223> OTHER INFORMATION: SPRY2 reverse-primer

<400> SEQUENCE: 8
ggtcactcca gcaggcttag                                          20

<210> SEQ ID NO 9
<211> LENGTH: 20
<212> TYPE: DNA
<213> ORGANISM: Artificial
<220> FEATURE:
<223> OTHER INFORMATION: STK32B forward-primer

<400> SEQUENCE: 9
gcagcactgt ttggagactg                                          20

<210> SEQ ID NO 10
<211> LENGTH: 19
<212> TYPE: DNA
<213> ORGANISM: Artificial
<220> FEATURE:
<223> OTHER INFORMATION: STK32B reverse-primer

<400> SEQUENCE: 10
tgaggaggtt gtgttgcac                                           19

<210> SEQ ID NO 11
<211> LENGTH: 20
<212> TYPE: DNA
<213> ORGANISM: Artificial
<220> FEATURE:
<223> OTHER INFORMATION: LILRB2-forward

<400> SEQUENCE: 11
ggtcttccct gaagcatctc                                          20

<210> SEQ ID NO 12
<211> LENGTH: 20
<212> TYPE: DNA
<213> ORGANISM: Artificial
<220> FEATURE:

```
<223> OTHER INFORMATION: LILRB2-reverse

<400> SEQUENCE: 12
ccctgacaac tgagggtgac                                          20

<210> SEQ ID NO 13
<211> LENGTH: 20
<212> TYPE: DNA
<213> ORGANISM: Artificial
<220> FEATURE:
<223> OTHER INFORMATION: PLXNB2-forward

<400> SEQUENCE: 13
agagaggcag cgtgaaagag                                          20

<210> SEQ ID NO 14
<211> LENGTH: 20
<212> TYPE: DNA
<213> ORGANISM: Artificial
<220> FEATURE:
<223> OTHER INFORMATION: PLXNB2-reverse

<400> SEQUENCE: 14
gcggtaagct gttcgtcttc                                          20

<210> SEQ ID NO 15
<211> LENGTH: 20
<212> TYPE: DNA
<213> ORGANISM: Artificial
<220> FEATURE:
<223> OTHER INFORMATION: HMGB2-forward

<400> SEQUENCE: 15
cggactcttc cgtcaatttc                                          20

<210> SEQ ID NO 16
<211> LENGTH: 20
<212> TYPE: DNA
<213> ORGANISM: Artificial
<220> FEATURE:
<223> OTHER INFORMATION: HMGB2-reverse

<400> SEQUENCE: 16 tatcacctt gggaggaacg                                           20
```